United States Patent
Genung et al.

(10) Patent No.: US 12,319,679 B2
(45) Date of Patent: Jun. 3, 2025

(54) MORPHOLINYL, PIPERAZINYL, OXAZEPANYL AND DIAZEPANYL O-GLYCOPROTEIN-2-ACETAMIDO-2-DEOXY-3-D-GLUCOPYRANOSIDASE INHIBITORS

(71) Applicant: BIOGEN MA INC., Cambridge, MA (US)

(72) Inventors: Nathan Genung, Charlestown, MA (US); Kevin M. Guckian, Northborough, MA (US); Jeffrey Vessels, Marlborough, MA (US); Lei Zhang, Westford, MA (US); Ryan Gianatassio, Everett, MA (US); Edward Yin Shiang Lin, Ashland, MA (US); Zhili Xin, Lexington, MA (US)

(73) Assignee: BIOGEN MA INC., Cambridge, MA (US)

( * ) Notice: Subject to any disclaimer, the term of this patent is extended or adjusted under 35 U.S.C. 154(b) by 975 days.

(21) Appl. No.: 17/311,232

(22) PCT Filed: Dec. 4, 2019

(86) PCT No.: PCT/US2019/064514
§ 371 (c)(1),
(2) Date: Jun. 4, 2021

(87) PCT Pub. No.: WO2020/117961
PCT Pub. Date: Jun. 11, 2020

(65) Prior Publication Data
US 2022/0017506 A1    Jan. 20, 2022

Related U.S. Application Data

(60) Provisional application No. 62/775,558, filed on Dec. 5, 2018.

(51) Int. Cl.
*C07D 417/12* (2006.01)
*C07D 417/14* (2006.01)

(52) U.S. Cl.
CPC ......... *C07D 417/12* (2013.01); *C07D 417/14* (2013.01)

(58) Field of Classification Search
CPC .............................. C07D 417/12; C07D 417/14
USPC ...................................................... 514/211.15
See application file for complete search history.

(56) References Cited

FOREIGN PATENT DOCUMENTS

| WO | WO-2014159234 A1 * | 10/2014 | ........... A61K 31/426 |
|----|--------------------|---------|------------------------|
| WO | 2018/109198 A1     | 6/2018  |                        |
| WO | 2018/109202 A1     | 6/2018  |                        |
| WO | 2018/140299 A1     | 8/2018  |                        |
| WO | 2018/154133 A1     | 8/2018  |                        |

OTHER PUBLICATIONS

Invitation to Pay Additional Fees for Application No. PCT/US2019/064514, dated Feb. 11, 2020, 8 pages.
International Search Report for Application No. PCT/US2019/064514, dated Apr. 2, 2020, 12 pages.

* cited by examiner

*Primary Examiner* — Kahsay Habte
(74) *Attorney, Agent, or Firm* — McCarter & English, LLP; Xin Zhang; Zhongyu Wang

(57) ABSTRACT

Described herein are compounds represented by formula (I), or a pharmaceutically acceptable salt thereof, pharmaceutical compositions comprising the same and methods of preparing and using the same. The variables Ar, X, $R^1$, $R^3$, $R^4$, $Y^1$, $Y^2$, m, n, and p are as defined herein.

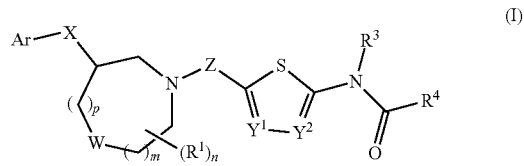

18 Claims, No Drawings

MORPHOLINYL, PIPERAZINYL, OXAZEPANYL AND DIAZEPANYL O-GLYCOPROTEIN-2-ACETAMIDO-2-DEOXY-3-D-GLUCOPYRANOSIDASE INHIBITORS

RELATED APPLICATION

This application is a 35 U.S.C. § 371 national stage filing of International Application No. PCT/US2019/064514, filed on Dec. 4, 2019, which in turn claims the benefit of the filing date, under 35 U.S.C. § 119(e), of U.S. Provisional Application No. 62/775,558, filed on Dec. 5, 2018. The entire contents of the aforementioned applications of which are incorporated herein by reference.

BACKGROUND

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This monosaccharide is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-glycoprotein-2-acetamido-2-deoxy-3-D-glucopyranosidase or O-GlcNAcase or OGA, removes this post-translational modification to liberate proteins, making the O-GlcNAc-modification a dynamic cycle occurring several times during the lifetime of a protein.

O-GlcNAc-modified proteins regulate a wide range of vital cellular functions including, e.g., transcription, proteasomal degradation and cellular signaling. O-GlcNAc is also found on many structural proteins, including the cytoskeletal protein "tau" which is responsible for stabilizing a key cellular network of microtubules that is essential for distributing proteins and nutrients within neurons. Importantly, tau has been clearly implicated in the etiology of several diseases including tauopathies, Alzheimer's disease, Parkinson's disease, dementia and cancer.

It is well established that Alzheimer's disease and a number of related tauopathies including Progressive Supranuclear Palsy (PSP) and amyotrophic lateral sclerosis (ALS) are characterized, in part, by the development of neurofibrillary tangles (NFTs). These NFTs are aggregates of paired helical filaments (PHFs) and are composed of an abnormal form of tau. In AD patients, tau becomes hyperphosphorylated, thereby disrupting its normal function, forming PHFs and ultimately aggregating to form NFTs.

Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups.

It has recently emerged that increases in phosphorylation levels result in decreased O-GlcNAc levels and conversely, increased O-GlcNAc levels correlate with decreased phosphorylation levels. It has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase, which prevents hyperphosphorylation of tau by preventing removal of O-GlcNac from tau, should compensate for the age-related impairment of glucose metabolism within the brains of health individuals as well as patients suffering from Alzheimer's disease or related neurodegenerative diseases.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

In view of foregoing technical challenge, and given the potential for regulation of O-GlcNAcase for treatment of AD, tauopathies and other neurological diseases, there remains a need for development of potent and selective O-GlcNAcase inhibitors.

SUMMARY

Described herein are compounds that are useful treating various diseases, disorders and medical conditions, including but not limited to those associated with proteins that are modified by O-GlcNAcase.

A first embodiment of a compound of the present invention is represented by the following structural formula:

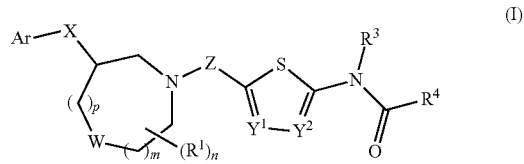

(I)

or a pharmaceutically acceptable salt thereof, wherein:

Ar is an optionally substituted 5- to 10-membered aryl or an optionally substituted 5- to 10-membered heteroaryl, wherein Ar is not a 9-membered bicyclic heteroaryl having 1 to 4 nitrogen atoms when the sum of m and p is 1;

W is O or $NR^d$;

X is $-CR^2R^2$, $-(CR^2R^2)_2$, $-(CR^2R^2)O-$ or $-O(CR^2R^2)$;

$Y^1$ and $Y^2$ are each $CR^c$ or N, wherein at least one of $Y^1$ or $Y^2$ is N;

Z is $CR^2R^2$, $-C(=O)$, $-(CR^2R^2)_2$, or $-CH_2C(=O)$;

$R^c$ is —H, halo, $-C_1$-$C_4$ alkyl, or $-C_1$-$C_4$ haloalkyl;

$R^d$ is —H, $C_1$-$C_4$ alkyl, $C_1$-$C_4$ haloalkyl, or $-C(=O)C_1$-$C_4$ alkyl;

m is 1 or 2;

p is 0 or 1, provided that the sum of m and p is not 3;

n is 0 or an integer from 1 to 9;

when n is other than 0, $R^1$, for each occurrence, is independently halo, $-C_1$-$C_4$ alkyl, $-C_1$-$C_4$ haloalkyl, or $-C_1$-$C_4$ alkoxy;

$R^2$, for each occurrence, is independently —H, halo, $-C_1$-$C_4$ alkyl, $-C_1$-$C_4$ haloalkyl, $-C_3$-$C_{10}$ cycloalkyl, or $-C_3$-$C_{10}$ halocycloalkyl;

or alternatively two $R^2$ together with the carbon atom to which they are attached form a $-C_3$-$C_{10}$ cycloalkyl;

$R^3$ is —H or $-C_1$-$C_4$ alkyl; and $R^4$ is —H, $-C_1$-$C_4$ alkyl, $-C_1$-$C_4$ haloalkyl, or $-C_3$-$C_6$ cycloalkyl;

or alternatively $R^3$ and $R^4$ taken together with their intervening atoms form an optionally substituted 5- to 7-membered heterocyclyl.

Provided is a pharmaceutical composition comprising at least one compound described herein, or a pharmaceutically acceptable salt thereof, and at least one pharmaceutically acceptable excipient.

Also provided is a method of treating a subject with a disease or condition selected from a neurodegenerative disease, a tauopathy, diabetes, cancer and stress, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of inhibiting O-GlcNAcase in a subject in need thereof, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of treating a disease or condition characterized by hyperphosphorylation of tau in the brain, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient. In one embodiment, the disease or condition characterized by hyperphosphorylation of tau in the brain is Alzheimer's disease.

DETAILED DESCRIPTION

Described herein are compounds that are useful treating various diseases, disorders and medical conditions, including but not limited to those associated with proteins that are modified by O-GlcNAcase.

In a first embodiment, a compound of the present invention is represented by the following structural formula (I):

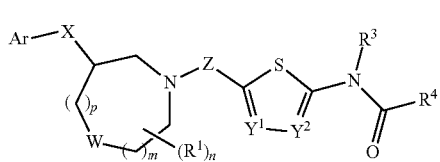

(I)

or a pharmaceutically acceptable salt thereof, wherein the variables are as defined above in the summary for a compound represented by formula (IA) or a pharmaceutically acceptable salt thereof.

In a second embodiment, a compound of the present invention is represented by one of the following structural formulas (IIA), (IIB), (IIB') or (ITC):

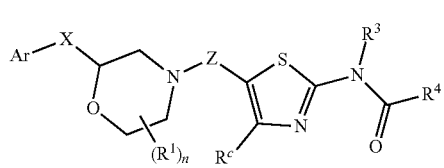

(IIA)

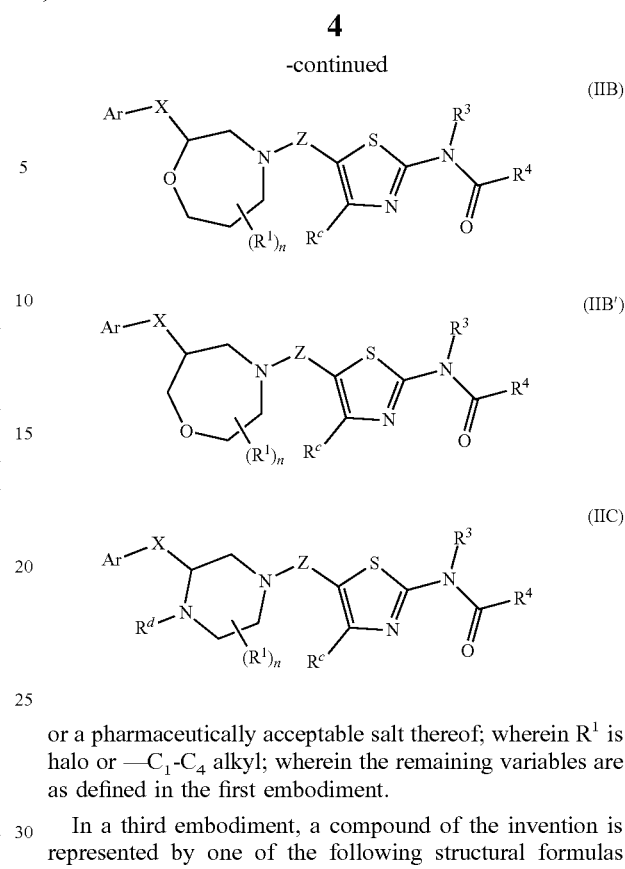

or a pharmaceutically acceptable salt thereof; wherein $R^1$ is halo or —$C_1$-$C_4$ alkyl; wherein the remaining variables are as defined in the first embodiment.

In a third embodiment, a compound of the invention is represented by one of the following structural formulas (IIIA), (IIIB), and (IIIB'):

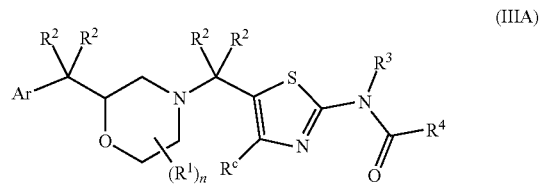

(IIIA)

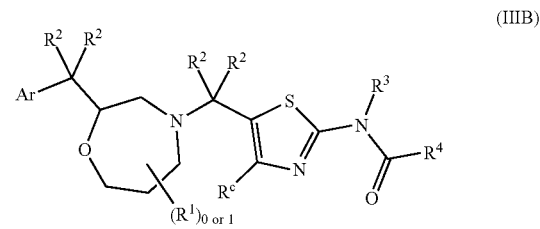

(IIIB)

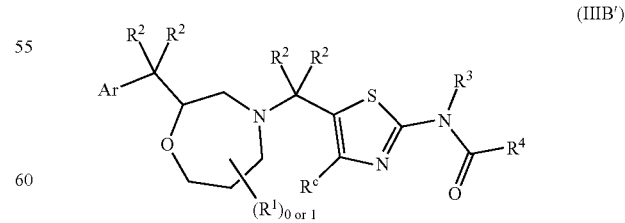

(IIIB')

or a pharmaceutically acceptable salt thereof; wherein $R^2$, for each occurrence, is independently H or $C_1$-$C_4$ alkyl; and wherein the remaining variables are as defined in the first or second embodiment.

In a fourth embodiment, a compound of the invention is represented by one of the following structural formulas (IIIC-1) and (IIIC-2):

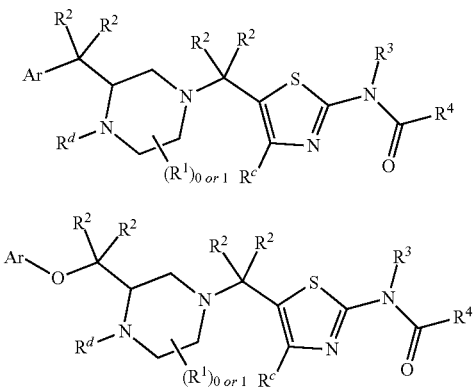

(IIIC-1)

(IIIC-2)

or a pharmaceutically acceptable salt thereof; wherein: $R^d$ is —H, —$C_1$-$C_4$ alkyl, or —C(=O)$C_1$-$C_4$alkyl; $R^1$ is —$C_1$-$C_4$ alkyl; $R^2$, for each occurrence, is independently —H or $C_1$-$C_4$ alkyl; and wherein the remaining variables are as defined in the first or second embodiment.

In a fifth embodiment, a compound of the invention is represented by the following structural formula (IVA):

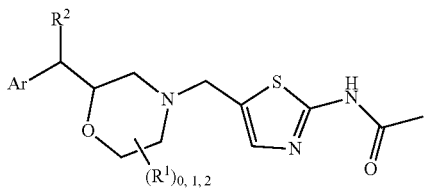

(IVA)

or a pharmaceutically acceptable salt thereof; wherein $R^1$ is —$C_1$-$C_4$ alkyl and wherein $R^2$ is —H, —$CH_3$ or —$CH_2CH_3$; and wherein the remaining variables are as defined in the first, second, or third embodiment.

In a sixth embodiment, a compound of the invention is represented by the following structural formula (IVA'):

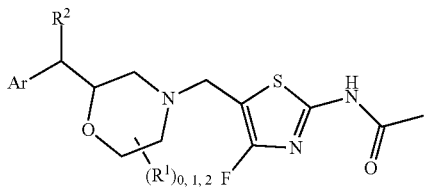

(IVA')

or a pharmaceutically acceptable salt thereof; wherein $R^1$ is —$C_1$-$C_4$ alkyl and wherein $R^2$ is —H, —$CH_3$ or —$CH_2CH_3$; and wherein the remaining variables are as defined in the first, second, or third embodiment.

In a seventh embodiment, a compound of the invention is represented by one of the following structural formulas (IVB) and (IVB'):

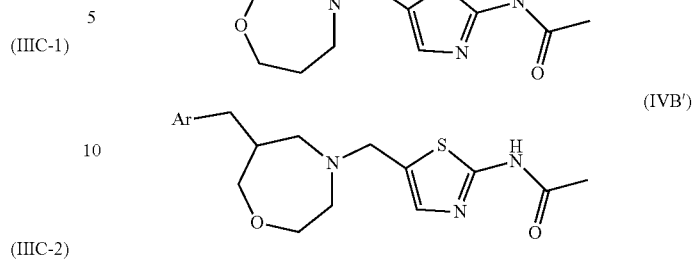

(IVB)

(IVB')

or a pharmaceutically acceptable salt thereof; wherein Ar is as defined in the first, second or third embodiment.

In an eighth embodiment, a compound of the invention is represented by one of the following structural formulas (IVC-1) and (IVC-2):

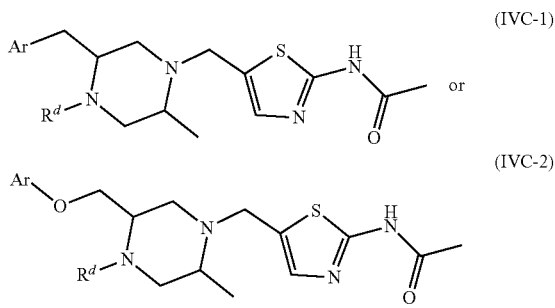

(IVC-1)

(IVC-2)

or a pharmaceutically acceptable salt thereof; wherein $R^d$ is —H, —$CH_3$, —$CH_2CH_3$, or —C(=O)$CH_3$; wherein the remaining variables are as defined in the first, second, or fourth embodiment.

In a ninth embodiment, a compound of the invention is represented by one of the following structural formulas (VA), (VA-1), (VA-2), (VA-3), (VC-1) and (VC-2):

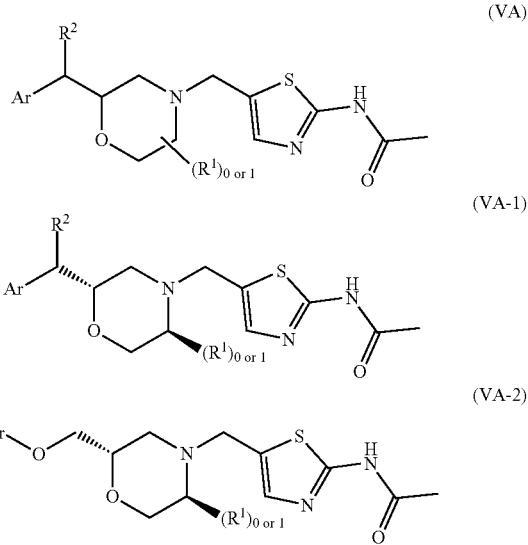

(VA)

(VA-1)

(VA-2)

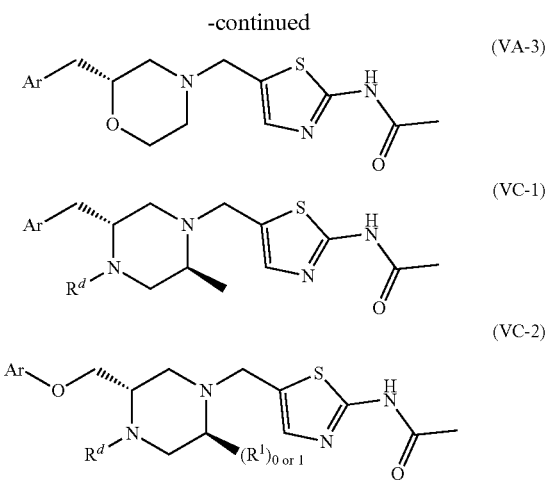

or a pharmaceutically acceptable salt thereof; wherein $R^1$ is $CH_3$; $R^2$ is —H or —$CH_3$; and Ar is as defined in the first, second, fourth, or eighth embodiment.

In a tenth embodiment, a compound of the invention is represented by one of the following structural formulas (VA'), (VA'-1), (VA'-2), (VA'-3)

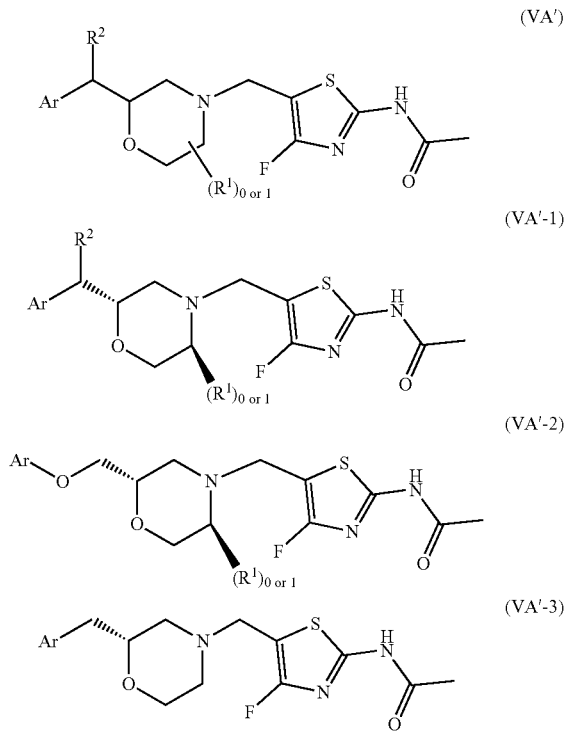

or a pharmaceutically acceptable salt thereof; wherein $R^1$ is $CH_3$; and $R^2$ is H or $CH_3$; and Ar is as defined in the first or second embodiment.

In an eleventh embodiment, in a compound of the invention in accordance to the first, second, third, fourth, fifth, sixth, seventh, eighth, ninth or tenth embodiment, or a pharmaceutically acceptable salt thereof, Ar is an optionally substituted 5- or 6-membered monocyclic heteroaryl.

In a twelfth embodiment, in a compound of the invention in accordance to the first, second, third, fourth, fifth, sixth, seventh, eighth, ninth, tenth or eleventh embodiment, or a pharmaceutically acceptable salt thereof, Ar is an optionally substituted 6-membered monocyclic heteroaryl comprising one or more nitrogen atoms.

In a thirteenth embodiment, in a compound of the invention in accordance to the first, second, third, fourth, fifth, sixth, seventh, eighth, ninth, tenth, eleventh or twelfth embodiment, or a pharmaceutically acceptable salt thereof, Ar is an optionally substituted pyridinyl, an optionally substituted pyrimidinyl, or an optionally substituted pyrazinyl.

In a fourteenth embodiment, in a compound of the invention in accordance to the first, second, third, fourth, fifth, sixth, seventh, eighth, ninth, or tenth embodiment, or a pharmaceutically acceptable salt thereof, Ar is an optionally substituted monocyclic heteroaryl comprising one or more nitrogen atoms.

In a fifteenth embodiment, in a compound of the invention in accordance to the first, second, third, fourth, fifth, sixth, seventh, eighth, ninth, tenth, eleventh, twelfth, or thirteenth embodiment, or a pharmaceutically acceptable salt thereof, Ar is pyridinyl, optionally substituted pyrimidinyl, or optionally substituted pyrazinyl.

In a sixteenth embodiment, in a compound of the invention in accordance to the first, second, third, fourth, fifth, sixth, seventh, eighth, ninth, tenth, eleventh, twelfth, thirteenth, or fourteenth embodiment, or a pharmaceutically acceptable salt thereof, Ar is optionally substituted

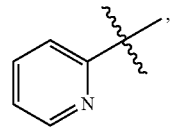 [SMILES: *c1ccccn1], optionally substituted

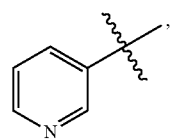 [SMILES: *c1cccnc1], optionally substituted

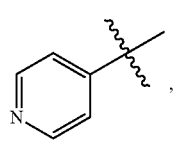, optionally substituted

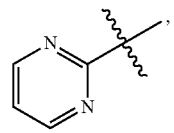 [SMILES: *c1ncccn1], optionally substituted

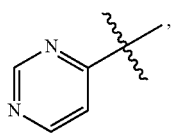 [SMILES: *c1ccncn1]

or optionally substituted

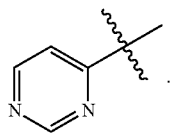

In a seventeenth embodiment, in a compound of the invention in accordance to the first, second, third, fourth, fifth, sixth, seventh, eighth, ninth, tenth, eleventh, twelfth, thirteenth, fourteenth, or fifteenth embodiment, or a pharmaceutically acceptable salt thereof, Ar is optionally substituted

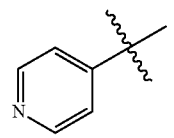 [SMILES: *c1ccncc1]

or optionally substituted

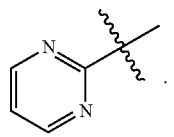 [SMILES: *c1ncccn1]

In an eighteenth embodiment, in a compound of the invention in accordance to the first, second, third, fourth, fifth, sixth, seventh, eighth, ninth, tenth, eleventh, twelfth, thirteenth, fourteenth, fifteenth, sixteenth or seventeenth embodiment, or a pharmaceutically acceptable salt thereof, wherein Ar is optionally substituted with one or more (e.g., two, three, four, etc.) groups selected from $C_1$-$C_4$ alkyl, $C_1$-$C_4$ haloalkyl, $C_3$-$C_6$cycloalkyl, $C_3$-$C_6$ heterocyclyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^y$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, NR$^x$(C=S)NR$^x$R$^y$, C(=S)R$^x$, C(=O)R$^x$, phenyl and monocyclic heteroaryl;
wherein
the $C_1$-$C_4$ alkyl group substituent on Ar is optionally substituted with —CN, —NO$_2$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S) NR$^x$R$^y$—NR$^x$C(=S)R$^y$, —NR$^x$(C=O)OR$^y$, —O(C=O)NR$^x$R$^y$, —NR$^x$(C=S)OR$^y$, —O(C=S) NR$^x$R$^y$, —NR$^x$(C=O)NR$^x$R$^y$, —NR$^x$(C=S)NR$^x$R$^y$, —C(=S)R$^x$, and —C(=O)R$^y$, $C_3$-$C_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from CH$_3$, halomethyl, halo, methoxy and halomethoxy);
the $C_3$-$C_6$ cycloalkyl, $C_3$-$C_6$ heterocyclyl, phenyl and monocyclic heteroaryl group substituent on Ar are optionally and independently substituted with $C_1$-$C_4$alkyl, $C_1$-$C_4$ haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^x$;
each R$^x$ and each R$^y$ is independently —H, $C_1$-$C_4$ alkyl, or $C_3$-$C_8$ cycloalkyl; wherein the $C_1$-$C_4$ alkyl or $C_3$-$C_8$ cycloalkyl represented by R$^x$ or R$^y$ is optionally substituted with one or more substituents selected from halo, hydroxyl, $C_3$-$C_6$ cycloalkyl and phenyl (optionally substituted with one or more groups selected from —CH$_3$, halomethyl, halo, methoxy or halomethoxy);
R$^z$ is H, $C_1$-$C_4$ alkyl, $C_1$-$C_4$ alkoxy, $C_3$-$C_8$ cycloalkyl, or $C_3$-$C_8$ heterocyclyl; wherein the $C_1$-$C_4$ alkyl or $C_3$-$C_8$ cycloalkyl group represented by R$^z$ is optionally substituted with one or more substituents selected from —CN, halo, hydroxyl, $C_1$-$C_4$ alkyl, $C_1$-$C_4$ alkoxy, $C_3$-$C_6$ cycloalkyl and phenyl (optionally substituted with one or more groups selected from —CH$_3$, halomethyl, halo, methoxy and halomethoxy); and
i is 0, 1, or 2.

In a nineteenth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth or eighteenth embodiment, or a pharmaceutically acceptable salt thereof, Ar is optionally substituted with one or more (e.g., two, three, four, etc.) groups selected from $C_1$-$C_4$ alkyl, $C_1$-$C_4$ haloalkyl, halo, —CN, —OR$^z$, and —NR$^x$R$^y$.

In a twentieth embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, or eighteenth embodiments, or a pharmaceutically acceptable salt thereof, Ar is optionally substituted with one or more (e.g., two, three, four, etc.) groups selected from $C_1$-$C_4$ alkyl, $C_1$-$C_4$ haloalkyl, —F, —Cl, —CN, and —OR$^z$; wherein R$^z$ is $C_1$-$C_4$ alkyl optionally substituted with one or more halo groups.

In a twenty-first embodiment, in a compound of the invention in accordance to the first, second, third, fourth, fifth, sixth, seventh, eighth, ninth, tenth, eleventh, twelfth, thirteenth, fourteenth, fifteenth, sixteenth, seventeenth, eighteenth, or nineteenth embodiment, or a pharmaceutically acceptable salt thereof, Ar is optionally substituted with one or more (e.g., two, three, four, etc.) groups selected from —CH$_3$, —CF$_3$, —CHF$_2$, —F, —OCH$_3$, —OCHF$_2$, —OCH$_2$CH$_3$, —OCH(CH$_3$)$_2$, and —OCH$_2$CF$_3$.

In another embodiment, a compound of the invention is selected from the compounds described in the exemplifications herein. Pharmaceutically acceptable salts thereof as well as the neutral forms are included.

In another embodiment of the invention is a compound selected from the group consisting of:

(R)—N-(5-((2-((5-fluoropyrimidin-2-yl)methyl)morpholino)methyl)thiazol-2-yl)acetamide;
(R)—N-(5-((2-((2-methoxypyridin-4-yl)methyl)morpholino)methyl)thiazol-2-yl)acetamide;
(R)—N-(5-((2-(2-methoxy-3-methylpyridin-4-yl)methyl)morpholino)methyl)thiazol-2-yl)acetamide;
(R)—N-(5-((2-(4-fluoro-3-methoxybenzyl)morpholino)methyl)thiazol-2-yl)acetamide;
(R)—N-(5-((2-((2-methoxypyrimidin-4-yl)methyl)morpholino)methyl)thiazol-2-yl)acetamide;
(R)—N-(5-((2-((6-methoxypyrimidin-4-yl)methyl)morpholino)methyl)thiazol-2-yl)acetamide;
(R)—N-(5-((2-(2-(2,2,2-trifluoroethoxy)pyridin-4-yl)methyl)morpholino)methyl)thiazol-2-yl)acetamide;
(R)—N-(5-((2-((2-ethoxypyridin-4-yl)methyl)morpholino)methyl)thiazol-2-yl)acetamide;
(R)—N-(5-((2-((2-isopropoxypyridin-4-yl)methyl)morpholino)methyl)thiazol-2-yl)acetamide;
(R)—N-(5-((2-(2-(difluoromethyl)pyridin-4-yl)methyl)morpholino)methyl)thiazol-2-yl)acetamide;
(R)—N-(5-((2-(2-methylpyrimidin-4-yl)methyl)morpholino)methyl)thiazol-2-yl)acetamide;
(R)—N-(5-((2-(3-fluoro-2-methoxypyridin-4-yl)methyl)morpholino)methyl)thiazol-2-yl)acetamide;
(R)—N-(5-((2-((5-methylpyridin-2-yl)methyl)morpholino)methyl)thiazol-2-yl)acetamide;
(R)—N-(5-((2-(2-(difluoromethoxy)pyridin-4-yl)methyl)morpholino)methyl)thiazol-2-yl)acetamide;
(R)—N-(5-((2-((5-fluoro-4-methylpyridin-2-yl)methyl)morpholino)methyl)thiazol-2-yl)acetamide;
(R)—N-(5-((2-((6-methylpyridin-3-yl)methyl)morpholino)methyl)thiazol-2-yl)acetamide;
(R)—N-(5-((2-((2-methylpyridin-4-yl)methyl)morpholino)methyl)thiazol-2-yl)acetamide;
(R)—N-(5-((2-(2,6-dimethylpyridin-4-yl)methyl)morpholino)methyl)thiazol-2-yl)acetamide;
N-(5-((R)-1-((R)-2-((5-fluoropyrimidin-2-yl)methyl)morpholino)ethyl)thiazol-2-yl)acetamide;
N-(5-((S)-1-((R)-2-((5-fluoropyrimidin-2-yl)methyl)morpholino)ethyl)thiazol-2-yl)acetamide;
N-(5-(((R)-2-((R)-1-(5-fluoropyrimidin-2-yl)ethyl)morpholino)methyl)thiazol-2-yl)acetamide;
N-(5-(((R)-2-((S)-1-(5-fluoropyrimidin-2-yl)ethyl)morpholino)methyl)thiazol-2-yl)acetamide;
N-(5-(((S)-2-((S)-1-(5-fluoropyrimidin-2-yl)ethyl)morpholino)methyl)thiazol-2-yl)acetamide;
N-(5-(((S)-2-((R)-1-(5-fluoropyrimidin-2-yl)ethyl)morpholino)methyl)thiazol-2-yl)acetamide;
N-(5-(((2R,5S)-2-((5-fluoropyrimidin-2-yl)methyl)-5-methylmorpholino)methyl)thiazol-2-yl)acetamide;
N-(5-(((2S,5S)-2-((5-fluoropyrimidin-2-yl)methyl)-5-methylmorpholino)methyl)thiazol-2-yl)acetamide;
N-(5-(((2R,5S)-2-((2,6-dimethylpyridin-4-yl)methyl)-5-methylmorpholino)methyl)thiazol-2-yl)acetamide;
N-(5-(((2R,5S)-5-methyl-2-((2-methylpyridin-4-yl)methyl)morpholino)methyl)thiazol-2-yl)acetamide;
N-(5-(((2R,5S)-5-methyl-2-((6-methylpyridin-3-yl)methyl)morpholino)methyl)thiazol-2-yl)acetamide;
N-(5-(((cis)-2-((5-fluoropyrimidin-2-yl)methyl)-6-methylmorpholino)methyl)thiazol-2-yl)acetamide;
N-(5-(((2R,6S)-2-((5-fluoropyrimidin-2-yl)methyl)-6-methylmorpholino)methyl)thiazol-2-yl)acetamide;
N-(5-(((2S,6R)-2-((5-fluoropyrimidin-2-yl)methyl)-6-methylmorpholino)methyl)thiazol-2-yl)acetamide;
N-(5-((2-(2,6-dimethylpyridin-4-yl)methyl)-1,4-oxazepan-4-yl)methyl)thiazol-2-yl)acetamide;
(S)—N-(5-((2-(2,6-dimethylpyridin-4-yl)methyl)-1,4-oxazepan-4-yl)methyl)thiazol-2-yl)acetamide;
(R)—N-(5-((2-(2,6-dimethylpyridin-4-yl)methyl)-1,4-oxazepan-4-yl)methyl)thiazol-2-yl)acetamide;
N-(5-((2-((5-fluoropyrimidin-2-yl)methyl)-1,4-oxazepan-4-yl)methyl)thiazol-2-yl)acetamide;
(S)—N-(5-((2-((5-fluoropyrimidin-2-yl)methyl)-1,4-oxazepan-4-yl)methyl)thiazol-2-yl)acetamide;
(R)—N-(5-((2-((5-fluoropyrimidin-2-yl)methyl)-1,4-oxazepan-4-yl)methyl)thiazol-2-yl)acetamide;
N-(5-((2-(2-methoxypyridin-4-yl)methyl)-1,4-oxazepan-4-yl)methyl)thiazol-2-yl)acetamide;
(S)—N-(5-((2-(2-methoxypyridin-4-yl)methyl)-1,4-oxazepan-4-yl)methyl)thiazol-2-yl)acetamide;
(R)—N-(5-((2-(2-methoxypyridin-4-yl)methyl)-1,4-oxazepan-4-yl)methyl)thiazol-2-yl)acetamide;
N-(5-((6-((2,6-dimethylpyridin-4-yl)methyl)-1,4-oxazepan-4-yl)methyl)thiazol-2-yl)acetamide;
(S)—N-(5-((6-((2,6-dimethylpyridin-4-yl)methyl)-1,4-oxazepan-4-yl)methyl)thiazol-2-yl)acetamide;
(R)—N-(5-((6-((2,6-dimethylpyridin-4-yl)methyl)-1,4-oxazepan-4-yl)methyl)thiazol-2-yl)acetamide;
N-(5-((6-((5-fluoropyrimidin-2-yl)methyl)-1,4-oxazepan-4-yl)methyl)thiazol-2-yl)acetamide;
(S)—N-(5-((6-((5-fluoropyrimidin-2-yl)methyl)-1,4-oxazepan-4-yl)methyl)thiazol-2-yl)acetamide;
(R)—N-(5-((6-((5-fluoropyrimidin-2-yl)methyl)-1,4-oxazepan-4-yl)methyl)thiazol-2-yl)acetamide;
N-(5-((6-((2-methoxypyridin-4-yl)methyl)-1,4-oxazepan-4-yl)methyl)thiazol-2-yl)acetamide;
(S)—N-(5-((6-((2-methoxypyridin-4-yl)methyl)-1,4-oxazepan-4-yl)methyl)thiazol-2-yl)acetamide;
(R)—N-(5-((6-((2-methoxypyridin-4-yl)methyl)-1,4-oxazepan-4-yl)methyl)thiazol-2-yl)acetamide;
(R)—N-(4-fluoro-5-((2-((6-methylpyridin-3-yl)methyl)morpholino)methyl)thiazol-2-yl)acetamide;
N-(4-fluoro-5-(((2R,5S)-5-methyl-2-((6-methylpyridin-3-yl)methyl)morpholino)methyl)thiazol-2-yl)acetamide;
N-(5-(((2S,5R)-2-methyl-5-((2-methylpyridin-4-yl)methyl)piperazin-1-yl)methyl)thiazol-2-yl)acetamide;
N-(5-(((2S,5R)-2,4-dimethyl-5-((2-methylpyridin-4-yl)methyl)piperazin-1-yl)methyl)thiazol-2-yl)acetamide;
N-(5-(((2S,5R)-4-ethyl-2-methyl-5-((2-methylpyridin-4-yl)methyl)piperazin-1-yl)methyl)thiazol-2-yl)acetamide;
N-(5-(((2S,5R)-5-((5-fluoropyrimidin-2-yl)methyl)-2-methylpiperazin-1-yl)methyl)thiazol-2-yl)acetamide;
N-(5-(((2S,5R)-5-((5-fluoropyrimidin-2-yl)methyl)-2,4-dimethylpiperazin-1-yl)methyl)thiazol-2-yl)acetamide;
N-(5-(((2S,5R)-5-((2,6-dimethylpyridin-4-yl)methyl)-2-methylpiperazin-1-yl)methyl)thiazol-2-yl)acetamide;
N-(5-(((2S,5R)-2-methyl-5-((6-methylpyridin-3-yl)methyl)piperazin-1-yl)methyl)thiazol-2-yl)acetamide;
N-(5-(((2S,5R)-5-((2,6-dimethylpyridin-4-yl)methyl)-2,4-dimethylpiperazin-1-yl)methyl)thiazol-2-yl)acetamide;
N-(5-(((2S,5R)-2,4-dimethyl-5-((6-methylpyridin-3-yl)methyl)piperazin-1-yl)methyl)thiazol-2-yl)acetamide;
N-(5-(((2S,5R)-4-ethyl-2-methyl-5-((6-methylpyridin-3-yl)methyl)piperazin-1-yl)methyl)thiazol-2-yl)acetamide;
N-(5-(((2S,5R)-5-((2,6-dimethylpyridin-4-yl)methyl)-2-methylpiperazin-1-yl)methyl)thiazol-2-yl)acetamide;
N-(5-(((2S,5R)-5-((2-methoxypyridin-4-yl)methyl)-2-methylpiperazin-1-yl)methyl)thiazol-2-yl)acetamide;

N-(5-(((2S,5R)-5-((2,6-dimethylpyrimidin-4-yl)methyl)-2,4-dimethylpiperazin-1-yl)methyl)thiazol-2-yl)acetamide;
N-(5-(((2S,5R)-5-((2-methoxypyridin-4-yl)methyl)-2,4-dimethylpiperazin-1-yl)methyl)thiazol-2-yl)acetamide;
N-(5-((3-((5-fluoropyrimidin-2-yl)methyl)piperazin-1-yl)methyl)thiazol-2-yl)acetamide;
N-(5-((3-((2-methoxypyridin-4-yl)methyl)piperazin-1-yl)methyl)thiazol-2-yl)acetamide;
N-(5-(((2S,5S)-5-(((2,6-dimethylpyridin-4-yl)oxy)methyl)-2-methylpiperazin-1-yl)methyl)thiazol-2-yl)acetamide;
N-(5-(((2S,5S)-5-(((2,6-dimethylpyridin-4-yl)oxy)methyl)-2,4-dimethylpiperazin-1-yl)methyl)thiazol-2-yl)acetamide;
N-(5-(((2S,5S)-2-(((2,6-dimethylpyridin-4-yl)oxy)methyl)-5 methylmorpholino)methyl)thiazol-2-yl)acetamide;
N-(5-(((2S,5S)-2-(((2,6-dimethylpyridin-4-yl)oxy)methyl)-5 methylmorpholino)methyl)thiazol-2-yl)acetamide;
(S)—N-(5-((3-((2,6-dimethylpyridin-4-yl)methyl)piperazin-1-yl)methyl)thiazol-2-yl)acetamide hydrochloride;
(S)—N-(5-((3-((2,6-dimethylpyridin-4-yl)methyl)-4-methylpiperazin-1-yl)methyl)thiazol-2-yl)acetamide;
N-(5-((3-(4-fluoro-3-methoxybenzyl)piperazin-1-yl)methyl)thiazol-2-yl)acetamide;
(R)—N-(5-((3-((2-methylpyridin-4-yl)methyl)piperazin-1-yl)methyl)thiazol-2-yl)acetamide;
(S)—N-(5-((3-((2-methylpyridin-4-yl)methyl)piperazin-1-yl)methyl)thiazol-2-yl)acetamide; and
(S)—N-(5-((4-methyl-3-((2-methylpyridin-4-yl)methyl)piperazin-1-yl)methyl)thiazol-2-yl)acetamide;
or a pharmaceutically acceptable salt thereof.

As used herein, the term "alkyl" refers to a fully saturated branched or straight chained hydrocarbon moiety. Unless otherwise specified, the alkyl comprises 1 to 12 carbon atoms, preferably 1 to 8 carbon atoms, more preferably 1 to 6 carbon atoms or most preferably 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl and n-hexyl.

As used herein, the term "alkoxy" refers to the group —OR, in which R is an alkyl or a cycloalkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopropyl, —O-cyclobutyl, —O-cyclopentyl and —O-cyclohexyl.

As used herein, the terms "aryl", "aryl group", "aryl ring", "aromatic group" and "aromatic ring" are used interchangeably to refer to an aromatic 5- to 12-membered monocyclic or bicyclic carbon ring system. Examples of monocyclic aryl systems include, but are not limited to, cyclopenta-1,3-dien-1-yl, phenyl, naphthyl and the like.

The number of carbon atoms in a group is specified herein by the prefix "C$_x$", wherein x and xx are integers. For example, "C$_{1-4}$ alkyl" is an alkyl group which has from 1 to 4 carbon atoms.

As used herein, the term "halogen" or "halo" may be fluoro, chloro, bromo or iodo.

As used herein, the term "haloalkyl" refers to an alkyl, as defined herein, that is substituted by one or more halo groups as defined herein.

As used herein, the terms "heterocyclyl", "heterocyclyl group", "heterocyclic" and "heterocyclic ring" are used interchangeably to refer to a saturated, unsaturated, non-aromatic, monocyclic or bicyclic (e.g., fused) ring system which has from 3- to 12-ring members, or in particular 3- to 6-ring members or 5- to 7-ring members, at least one of which is a heteroatom, and up to 4 (e.g., 1, 2, 3 or 4) of which may be heteroatoms, wherein the heteroatoms are independently selected from O, S and N, and wherein C can be oxidized (e.g., C(═O)), N can be oxidized (e.g., N(O)) or quaternized (e.g. N$^+$), and S can be optionally oxidized to sulfoxide and sulfone. Examples of non-aromatic heterocyclyls include aziridinyl, azetidinyl, oxetanyl, thietanyl, pyrrolidinyl, tetrahydrofuranyl, thiolanyl, imidazolidinyl, pyrazolidinyl, isoxazolidinyl, isothiazolidinyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, hydantoinyl, pyrrolidinonyl, tetrahydrothiopyranyl, tetrahydropyridinyl, and thiopyranyl, and the like. Examples of bicyclic nonaromatic heterocyclic ring systems include benzo[1,3]dioxolyl, tetrahydroindolyl, and 2-azaspiro[3.3]heptanyl, and the like.

As used herein, the terms "heteroaryl", "heteroaryl group", "heteroaromatic" and "heteroaromatic ring" are used interchangeably to refer to an aromatic 5- to 12-membered monocyclic or bicyclic ring system, having 1 to 4 heteroatoms independently selected from O, S and N, and wherein N can be oxidized (e.g., N(O)) or quaternized, and S can be optionally oxidized to sulfoxide and sulfone. "Heteroaryl" includes a heteroaromatic group that is fused to a phenyl group or non-aromatic heterocycle such as tetrahydrofuran, pyran, pyrrolidine, piperidine, and the like. As used herein, the heteroaryl group Ar can be attached to the rest of a compound of the invention at any ring that has an open valency. Examples of heteroaryls include pyrrolyl, furanyl, imidazolyl, pyrazolyl, oxazolyl, isoxazolyl, thiazolyl, isothiazolyl, oxadiazolyl, thiadiazolyl, triazolyl, tetrazolyl, pyridyl, pyrazinyl, pyrimidyl, pyridazinyl, triazinyl, tetrazinyl, 1-oxo-pyridyl, thienyl, azaindolyl, benzimidazolyl, benzofuryl, benzoisoxazolyl, benzoisothiazolyl, benzothiadiazolyl, benzothiazolyl, benzothienyl, benzotriazolyl, benzoxadiazolyl, benzoxazolyl, cyclopentaimidazolyl, cyclopentatriazolyl, imidazo[1,2-a]pyridyl, indazolyl, indolizinyl, indolyl, isoquinolinyl, oxazolopyridinyl, purinyl, pyrazolo[3,4]pyrimidinyl, pyridopyazinyl, pyridopyrimidinyl, pyrrolo[2,3]pyrimidinyl, pyrrolopyrazolyl, pyrroloimidazolyl, pyrrolotriazolyl, quinazolinyl, quinolinyl, thiazolopyridinyl, napthyridyl, and the like.

As used herein, the term "cycloalkyl" refers to completely saturated monocyclic or bicyclic (e.g., fused) hydrocarbon groups of 3-12 carbon atoms, 3-6 carbon atoms or 5-7 carbon atoms.

As used herein, the term "halocycloalkyl" refers to a cycloalkyl, as defined herein, that is substituted by one or more halo groups as defined herein.

A substituted alkyl, phenyl, heteroaryl, non-aromatic heterocyclyl or heterocyclyl group is an alkyl, phenyl, heteroaryl, non-aromatic heterocyclyl or heterocyclyl group that has one or more substituents. Suitable substituents are those that do not significantly decrease the O-GlcNAcase inhibitory activity of a compound of formula (I), (IIA), (IIB), (IIB'), (ITC), (IIIA), (IIIB), (IIIB'), (IIIC-2), (IVA), (IVA'), (IVB), (IVB'), (IVC-1), (IVC-2), (VA), (VA'), (VA-1), (VA'-1), (VA-2), (VA'-2), (VA-3), (VA'-3), (VC-1), (VC-2) (hereinafter collectively a compound of any one of formulas (I) through (VC-2)), or a pharmaceutically acceptable salt thereof. Examples of suitable substituents for an alkyl, phenyl, heteroaryl, non-aromatic heterocyclyl or heterocyclyl group include but are not limited to C$_1$-C$_4$ alkyl, C$_1$-C$_4$ haloalkyl, C$_3$-C$_6$ cycloalkyl, halo, —CN, —NO$_2$, —OR$^z$, —NR$^x$R$^y$, —S(O)$_t$R$^x$, —NR$^x$S(O)$_t$R$^y$, —S(O)$_t$N-

$R^xR^y$, —C(=O)$OR^x$, —OC(=O)$OR^x$, —C(=S)$OR^y$, —O(C=S)$R^x$, —C(=O)$NR^xR^y$, —$NR^xC$(=O)$R^y$, —C(=S)$NR^xR^y$, —$NR^xC$(=S)$R^y$, —$NR^x$(C=O)$OR^y$, —O(C=O)$NR^xR^y$, —$NR^x$(C=S)$OR^y$, —O(C=S)$NR^xR^y$, —$NR^x$(C=O)$NR^xR^y$, —$NR^x$(C=S)$NR^xR^y$, —C(=S)$R^x$, —C(=O)$R^x$, phenyl and monocyclic heteroaryl. The $C_1$-$C_4$ alkyl group substituent is optionally substituted with —CN, —$NO_2$, —$OR^z$, —$NR^xR^y$, —S(O)$_iR^x$, —$NR^xS$(O)$_iR^y$, —S(O)$_iNR^xR^y$, —C(=O)$OR^x$, —OC(=O)$OR^x$, —C(=S)$OR^x$, —O(C=S)$R^x$, —C(=O)$NR^xR^y$, —$NR^xC$(=O)$R^y$, —C(=S)$NR^xR^y$, —$NR^xC$(=S)$R^y$, —$NR^x$(C=O)$OR^y$, —O(C=O)$NR^xR^y$, —$NR^x$(C=S)$OR^y$, —O(C=S)$NR^xR^y$, —$NR^x$(C=O)$NR^xR^y$, —$NR^x$(C=S)$NR^xR^y$, —C(=S)$R^x$, and —C(=O)$R^y$, $C_3$-$C_6$ cycloalkyl (optionally substituted with one or more groups selected from —$CH_3$, halomethyl, halo, methoxy and halomethoxy), monocyclic heteroaryl (optionally substituted with one or more groups selected from —$CH_3$, halomethyl, halo, methoxy or halomethoxy) and phenyl (optionally substituted with one or more groups selected from —$CH_3$, halomethyl, halo, methoxy and halomethoxy). The $C_3$-$C_6$ cycloalkyl, phenyl and monocyclic heteroaryl group substituents are optionally and independently substituted with $C_1$-$C_4$ alkyl, $C_1$-$C_4$ haloalkyl, halo, CN, $NO_2$, $OR^z$, —$NR^xR^y$, —S(O)$_iR^x$, —$NR^xS$(O)$_iR^y$, —S(O)$_iNR^xR^y$, —C(=O)$OR^x$, —OC(=O)$OR^x$, —C(=S)$OR^x$, —O(C=S)$R^y$, —C(=O)$NR^xR^y$, —$NR^xC$(=O)$R^y$, —C(=S)$NR^xR^y$, —$NR^xC$(=S)$R^y$, —$NR^x$(C=O)$OR^y$, —O(C=O)$NR^xR^y$, —$NR^x$(C=S)$OR^y$, —O(C=S)$NR^xR^y$, —$NR^x$(C=O)$NR^xR^y$, —$NR^x$(C=S)$NR^xR^y$, —C(=S)$R^x$, and —C(=O)$R^x$. In these substituents, each $R^x$ and each $R^y$ is independently H, $C_1$-$C_4$ alkyl, or $C_3$-$C_8$ cycloalkyl, where the $C_1$-$C_4$ alkyl or $C_3$-$C_8$ cycloalkyl represented by $R^x$ or $R^y$ is optionally substituted with one or more substituents selected from halo, hydroxyl, $C_3$-$C_6$ cycloalkyl and phenyl (optionally substituted with one or more groups selected from —$CH_3$, halomethyl, halo, methoxy or halomethoxy). In these substituents, $R^z$ is H, $C_1$-$C_4$ alkyl, or $C_3$-$C_8$ cycloalkyl, where the $C_1$-$C_4$ alkyl or $C_3$-$C_8$ cycloalkyl group represented by $R^z$ is optionally substituted with one or more substituents selected from halo, hydroxyl, $C_3$-$C_6$ cycloalkyl and phenyl (optionally substituted with one or more groups selected from $CH_3$, halomethyl, halo, methoxy and halomethoxy). In these substituents, i is 0, 1, or 2.

Pharmaceutically acceptable salts of the compounds disclosed herein are also included in the invention. In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, α-ketoglutarate or α-glycerophosphate. Inorganic salts may also be formed, including hydrochloride, sulfate, nitrate, bicarbonate and carbonate salts.

Pharmaceutically acceptable salts may be obtained using standard procedures well known in the art, for example by reacting a sufficiently basic compound such as an amine with a suitable acid; affording a physiologically acceptable anion. Alkali metal (for example, sodium, potassium or lithium) or alkaline earth metal (for example calcium) salts of carboxylic acids can also be made.

Pharmaceutically acceptable base addition salts can be prepared from inorganic and organic bases. Suitable bases include but are not limited to alkali metal hydroxides, alkaline earth metal hydroxides, carbonates, bicarbonates, and the like.

Some of the disclosed compounds, or pharmaceutically acceptable salts thereof, contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis or chromatographic separation using a chiral stationary phase). The disclosed compounds may exist in tautomeric forms and mixtures and separate individual tautomers are contemplated. In addition, some compounds may exhibit polymorphism.

When a particular steroisomer (e.g., enantiomer, diastereomer, etc.) of a compound used in the disclosed methods is depicted by name or structure, the stereochemical purity of the compounds is at least 60%, 70%, 80%, 90%, 95%, 97%, 99%, 99.5% or 99.9%. "Stererochemical purity" means the weight percent of the desired stereoisomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

The term "Peak 1" as used herein refers to the first eluding peak during the separation of enantiomers and/or diastereomers, which is followed by the subsequently eluding "Peak 2", and optionally, "Peak 3", and "Peak 4".

In one embodiment, any position occupied by hydrogen is meant to include enrichment by deuterium above the natural abundance of deuterium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

One aspect of the invention includes a method for inhibiting a glycosidase and/or a glycosidase signaling pathway in a cell, the method comprising contacting the cell with an effective amount of a compound of any one of formulas (I)

through (VC-2), or a pharmaceutically acceptable salt thereof. The glycosidase is preferably a glycoside hydrolase, more preferably a family 84 glycoside hydrolase, even more preferably O-glycoprotein-2-acetamido-2-deoxy-3-D-glucopyranosidase (O-GlcNAcase or OGA), most preferably a mammalian O-GlcNAcase. In one embodiment, the cell is contacted in vitro or in vivo. In one embodiment, contacting the cell includes administering the compound to a subject.

One aspect of the invention includes a method for inhibiting a glycosidase and/or a glycosidase signaling pathway in a subject in need thereof, the method comprising administering to the subject, a therapeutically effective amount of a compound of any one of formulas (I) through (VC-2), or a pharmaceutically acceptable salt thereof, thereby activating the glycosidase in the subject. The glycosidase is preferably a glycoside hydrolase, more preferably a family 84 glycoside hydrolase, even more preferably O-glycoprotein-2-acetamido-2-deoxy-3-D-glucopyranosidase (O-GlcNAcase or OGA), most preferably a mammalian O-GlcNAcase.

One aspect of the invention includes a method for promoting survival of a eukaryotic cell (e.g., a mammalian cell) or increasing the lifespan of the cell, the method comprising administering to the subject a therapeutically effective amount of a compound of any one of formulas (I) through (VC-2), or a pharmaceutically acceptable salt thereof, thereby promoting survival of the eukaryotic cell or increasing the lifespan of the cell.

One aspect of the invention includes a method for treating a disease or a condition that is caused, mediated and/or propagated by O-GlcNAcase activity in a subject, the method comprising administering to the subject a therapeutically effective amount of a compound of any one of formulas (I) through (VC-2), or a pharmaceutically acceptable salt thereof. Preferably, the disease or condition is a neurological disorder, diabetes, cancer or stress.

More preferably, the disease or condition is a neurological disorder. In one embodiment, the neurological disorder is one or more tauopathies selected from Acute ischemic stroke (AIS), Alzheimer's disease, Dementia, Amyotrophic lateral sclerosis (ALS). Amyotrophic lateral sclerosis with cognitive impairment (ALSci). Argyrophilic grain dementia, Bluit disease, Corticobasal degeneration (CBP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FIDP-17), Gerstmann-Straussler-Scheinker disease, Guadeloupean parkinsonism. Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GM), Variant Creutzfeldt-Jakob Disease (vCJD), Fatal Familial Insomnia, Kuru, Progressive supercortical gliosis, Progressive supranuclear palsy (PSP), Steele-Richardson-Olszewski syndrome, Subacute sclerosing panencephalitis. Tangle-only dementia, Huntington's disease, and Parkinson's disease. In another embodiment, the neurological disorder is one or more disorders selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, mild cognitive impairment (MCI), Huntington's disease, and Parkinson's disease. In yet another embodiment, the neurological disorder is Alzheimer's disease.

One aspect of the invention includes a method for treating a disease or a condition that is characterized by hyperphosphorylation of tau (e.g., hyperphosphorylation of tau in the brain) in a subject, the method comprising administering to the subject a therapeutically effective amount of a compound of any one of formulas (I) through (VC-2), or a pharmaceutically acceptable salt thereof. In one embodiment, the disease or condition is selected from Acute ischemic stroke (AIS), Alzheimer's disease, Dementia. Amyotrophic lateral sclerosis (ALS), Amyotrophic lateral sclerosis with cognitive impairment (ALSci), Argyrophilic grain dementia, Bluit disease, Corticobasal degeneration. (CBP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallidly-ponto-nigral degeneration. Parkinsonism-dementia complex of Guam, Pick's disease (PiD), Postencephalitic parkinsonism (PEP), Prion diseases (including Creutzfeldt-Jakob Disease (GJD). Variant Creutzfeldt-Jakob Disease (vCJD). Fatal Familial insomnia, Kuru, Progressive supercortical gliosis. Progressive supranuclear palsy (PSP), Steele-Richardson-Olszewski syndrome, Subacute sclerosing panencephalitis, Tangle-only dementia, Huntington's disease, and Parkinson's disease. In another embodiment, the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, ischemic stroke, mild cognitive impairment (MCI), Huntington's disease, and Parkinson's disease. In yet another embodiment, the disease or condition is Alzheimer's disease.

As used herein, the term "subject" and "patient" may be used interchangeably, and means a mammal in need of treatment, e.g., companion animals (e.g., dogs, cats and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: reducing the extent of the disease, disorder or syndrome; ameliorating or improving a clinical symptom or indicator associated with the disorder; and delaying, inhibiting or decreasing the likelihood of the progression of the disease, disorder or syndrome.

The term "an effective amount" means an amount of a compound of any one of formulas (I) through (VC-2), or a pharmaceutically acceptable salt thereof, e.g., 0.1 mg to 1000 mg/kg body weight, when administered to a subject, which results in beneficial or desired results, including clinical results, i.e., reversing, alleviating, inhibiting, reducing or slowing the progression of a disease or condition treatable by a compound of any one of formulas (I) through (VC-2), or a pharmaceutically acceptable salt thereof, reducing the likelihood of recurrence of a disease or condition treatable by a compound of any one of formulas (I) through (VC-2), or a pharmaceutically acceptable salt thereof or one or more symptoms thereof, e.g., as determined by clinical symptoms, compared to a control. The expression "an effective amount" also encompasses the amounts which are effective for increasing normal physiological function, for example, between 0.01 mg/kg per day to 500 mg/kg per day.

Another embodiment of the present invention is a pharmaceutical composition comprising at least one compound described herein, or a pharmaceutically acceptable salt thereof, and at least one pharmaceutically acceptable carrier.

Also included are the use of a compound of any one of formulas (I) through (VC-2), or a pharmaceutically acceptable salt thereof in the manufacture of a medicament for the treatment of one or more diseases or conditions described herein. Also included herein are pharmaceutical compositions comprising a compound of any one of formulas (I) through (VC-2), or a pharmaceutically acceptable salt thereof optionally together with a pharmaceutically acceptable carrier, in the manufacture of a medicament for the treatment of one or more diseases or conditions described herein. Also included is a compound of any one of formulas (I) through (VC-2), or a pharmaceutically acceptable salt thereof for use the treatment of a subject with one or more diseases or conditions described herein. Further included are pharmaceutical compositions comprising a compound of any one of formulas (I) through (VC-2), or a pharmaceutically acceptable salt thereof, optionally together with a pharmaceutically acceptable carrier, for use in the treatment of one or more diseases or conditions described herein.

The term "pharmaceutically acceptable carrier" refers to a non-toxic carrier, diluent, adjuvant, vehicle or excipient that does not adversely affect the pharmacological activity of the compound with which it is formulated, and which is also safe for human use. Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., a Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003, 20th edition) and in The United States Pharmacopeia: The National Formulary (USP 24 NF19) published in 1999.

A compound of any one of formulas (I) through (VC-2), or a pharmaceutically acceptable salt thereof, or the compositions of the present teachings may be administered, for example, by oral, parenteral, sublingual, topical, rectal, nasal, buccal, vaginal, transdermal, patch, pump administration or via an implanted reservoir, and the pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Other forms of administration included in this disclosure are as described in WO 2013/075083, WO 2013/075084, WO 2013/078320, WO 2013/120104, WO 2014/124418, WO 2014/151142, and WO 2015/023915, the contents of which are incorporated herein by reference.

Useful dosages of a compound or pharmaceutically acceptable salt thereof as described herein can be determined by comparing their in vitro activity and in vivo activity in animal models. Methods for the extrapolation of effective dosages in mice and other animals, to humans are known to the art; for example, see U.S. Pat. No. 4,938,949, which is incorporated by reference in its entirety.

EXEMPLIFICATIONS

General Methods

Chromatography on silica gel was carried out using 20-40 uM (particle size), 250-400 mesh, or 400-632 mesh silica gel using either a Teledyne ISCO Combiflash RF or a Grace Reveleris X2 with ELSD purification systems.

Analytical HPLC

Acidic HPLC: Conducted on a Shimadzu 20A instrument with an Ultimate C18 3.0×50 mm, 3 um column eluting with 2.75 mL/4 L TFA in water (solvent A) and 2.5 mL/4 L TFA in acetonitrile (solvent B) by the following methods:

Method A: using the following elution gradient 0%-60% (solvent B) over 6 minutes and holding at 60% for 2 minutes at a flow rate of 1.2 ml/minutes. Wavelength: UV 220 nm, 215 nm and 254 nm.

Method B: using the following elution gradient 10%-80% (solvent B) over 6 minutes and holding at 60% for 2 minutes at a flow rate of 1.2 ml/minutes. Wavelength: UV 220 nm, 215 nm and 254 nm.

Method C: using the following elution gradient 30%-90% (solvent B) over 6 minutes and holding at 60% for 2 minutes at a flow rate of 1.2 ml/minutes. Wavelength: UV 220 nm, 215 nm and 254 nm.

Basic HPLC: Conducted on a Shimadzu 20A instrument with Xbrige Shield RP-18, 5 um, 2.1×50 mm column eluting with 2 mL/4 L $NH_3H_2O$ in water (solvent A) and acetonitrile (solvent B), by the following methods:

Method D: using the following elution gradient 0%-60% (solvent B) over 4.0 minutes and holding at 60% for 2 minutes at a flow rate of 1.2 ml/minutes.

Method E: using the following elution gradient 10%-80% (solvent B) over 4.0 minutes and holding at 60% for 2 minutes at a flow rate of 1.2 ml/minutes.

Method F: using the following elution gradient 30%-90% (solvent B) over 4.0 minutes and holding at 60% for 2 minutes at a flow rate of 1.2 ml/minutes.

Analytical LCMS

Acidic LCMS: Conducted on a Shimadzu 2010 Series, Shimadzu 020 Series, or Waters Acquity UPLC BEH. (MS ionization: ESI) instrument equipped with a C18 column (2.1 mm×30 mm, 3.0 mm or 2.1 mm×50 mm, C18, 1.7 um), eluting with 1.5 mL/4 L TFA in water (solvent A) and 0.75 mL/4 LTFA in acetonitrile (solvent B) using the methods below: 1.5 minute methods:

General method: using the following elution gradient 5%-95% (solvent B) over 0.7 minutes and holding at 95% for 0.4 minutes at a flow rate of 1.5 ml/minutes. Wavelength: UV 220 nm and 254 nm.

2 Minute Methods:

Method A: using the following elution gradient 0%-60% (solvent B) over 0.9 minutes and holding at 60% for 0.6 minutes at a flow rate of 1.2 ml/minutes. Wavelength: UV 220 nm and 254 nm.

Method B: using the following elution gradient 10%-80% (solvent B) over 0.9 minutes and holding at 60% for 0.6 minutes at a flow rate of 1.2 ml/minutes. Wavelength: UV 220 nm and 254 nm.

Method C: using the following elution gradient 30%-90% (solvent B) over 0.9 minutes and holding at 60% for 0.6 minutes at a flow rate of 1.2 ml/minutes. Wavelength: UV 220 nm and 254 nm.

3.5 Minute Method:

Initial conditions, solvent A-95%: solvent B-5%; hold at initial from 0.0-0.1 min; Linear Ramp to solvent A-5%: solvent B-95% between 0.1-3.25 min; hold at solvent A-5%: solvent B-95% between 3.25-3.5 min. Diode array/MS detection.

4 Minute Methods:

Method A: using the following elution gradient 0%-60% (solvent B) over 3 minutes and holding at 60% for 0.5 minutes at a flow rate of 0.8 ml/minutes. Wavelength: UV 220 nm and 254 nm.

Method B: using the following elution gradient 10%-80% (solvent B) over 3 minutes and holding at 60% for 0.5 minutes at a flow rate of 0.8 ml/minutes. Wavelength: UV 220 nm and 254 nm.

Method C: using the following elution gradient 30%-90% (solvent B) over 3 minutes and holding at 60% for 0.5 minutes at a flow rate of 0.8 ml/minutes. Wavelength: UV 220 nm and 254 nm.

7 Minute Methods:

Method A: using the following elution gradient 0%-60% (solvent B) over 6 minutes and holding at 60% for 0.5 minutes at a flow rate of 0.8 ml/minutes. Wavelength: UV 220 nm and 254 nm.

Method B: using the following elution gradient 10%-80% (solvent B) over 6 minutes and holding at 60% for 0.5 minutes at a flow rate of 0.8 ml/minutes. Wavelength: UV 220 nm and 254 nm.

Method C: using the following elution gradient 30%-900% (solvent B) over 6 minutes and holding at 60% for 0.5 minutes at a flow rate of 0.8 ml/minutes. Wavelength: UV 220 nm and 254 nm.

Basic LCMS:

Conducted on a Shimadzu2020 Series or Waters Acquity UPLC BEH (MS ionization: ESI) instrument equipped with XBridge Shield RP18, 5 um column (2.1 mm×30 mm, 3.0 mm i.d.) or 2.1 mm×50 mm, C18, 1.7 um column, eluting with 2 mL/4 L $NH_3H_2O$ in water (solvent A) and acetonitrile (solvent B) using the methods below:

3 Minute Methods:

Method A: using the following elution gradient 0%-60% (solvent B) over 2 minutes and holding at 60% for 0.48 minutes at a flow rate of 1 ml/minutes. Wavelength: UV 220 nm and 254 nm.

Method B: using the following elution gradient 10%-80% (solvent B) over 2 minutes and holding at 60% for 0.48 minutes at a flow rate of 1 ml/minutes. Wavelength: UV 220 nm and 254 nm.

Method C: using the following elution gradient 30%-90% (solvent B) over 2 minutes and holding at 60% for 0.48 minutes at a flow rate of 1 ml/minutes. Wavelength: UV 220 nm and 254 nm.

3.5 Minute Method:

Initial conditions, solvent A-95%: solvent B-5%; hold at initial from 0.0-0.1 min; Linear Ramp to solvent A-5%: solvent B-95% between 0.1-3.25 min; hold at solvent A-5%: solvent B-95% between 3.25-3.5 min. Diode array/MS detection.

7 Minute Methods:

Method A: using the following elution gradient 0%-60% (solvent B) over 6 minutes and holding at 60% for 0.5 minutes at a flow rate of 0.8 ml/minutes. Wavelength: UV 220 nm and 254 nm.

Method B: using the following elution gradient 10%-80% (solvent B) over 6 minutes and holding at 60% for 0.5 minutes at a flow rate of 0.8 ml/minutes. Wavelength: UV 220 nm and 254 nm.

Method C: using the following elution gradient 30%-90% (solvent B) over 6 minutes and holding at 60% for 0.5 minutes at a flow rate of 0.8 ml/minutes. Wavelength: UV 220 nm and 254 nm.

SFC Analytical Separation

Instrument: Waters UPC2 analytical SFC (SFC-H). Column: ChiralCel OJ, 150×4.6 mm I.D., 3 μm. Mobile phase: A for CO2 and B for Ethanol (0.05% DEA). Gradient: B 40%. Flow rate: 2.5 mL/min. Back pressure: 100 bar. Column temperature: 35° C. Wavelength: 220 nm Preparative HPLC Purification General Method: Preparative HPLC was performed on a Gilson UV/VIS-156 with UV detection at 220/254 nm Gilson 281 automatic collection.

Acidic condition: Two acid grading systems used: Hydrochloride acid and Formic acid.

Method A: Hydrochloride acid: YMC-Actus Triart C18 150×30 mm×5 um, Gradient used 0-100% acetonitrile with water and corresponding acid (0.05% HCl).

Method B: Formic acid: Phenomenex Synergi C18 150×30 mm×4 um, Gradient used 0-100% acetonitrile with water and corresponding acid (0.225% formic acid), the gradient shape was optimized for individual separations.

Neutral condition: Xtimate C18 150×25 mm×5 um, Gradient used 0-100% (water (10 mM $NH_4HCO_3$)-ACN), the gradient shape was optimized for individual separations.

Basic condition: Waters Xbridge Prep OBD C18 150×30 10 um, Gradient used 0-100% water (0.04% $NH_3H_2O$+10 mM $NH_4HCO_3$)-acetonitrile, the gradient shape was optimized for individual separations.

Preparative HPLC-MS Purification

Columns Used:

Acid: Waters SunFire Prep, C18 5 um, OBD 19×100 mm

Base: Waters XSelect CSH Prep C18 5 um OBD 19×100 mm

Gradient Profile: 12 min Run: Initial conditions: A-95%: B-5%; hold at initial from 0.0-0.5 min; linear ramp from A-5% to variable B-% (typical range is from B-40% to B-75%) between 0.5-7.5 min; linear ramp from B-% to B-95% from 7.5-8.0 min; hold at A-5%:B-95% between 8.0-10.0 min; end of DAD/MS detection; linear ramp down to initial conditions between 10.0-10.5 min and hold at initial for 1.5 min.

Mobile Phase: Acid: A: 0.1% trifluoroacetic acid in water (v/v); Mobile phase B: 0.1% trifluoroacetic acid in acetonitrile (v/v). Base: A: 0.1% ammonia in water (v/v); Mobile phase B: 0.1% ammonia in acetonitrile (v/v)

Preparative SFC Purification

Instrument: MG III preparative SFC (SFC-1). Column: ChiralCel OJ, 250×30 mm I.D., 5 μm. Mobile phase: A for CO₂ and B for Ethanol (0.1% NH₃H₂O). Gradient: B 50%. Flow rate: 40 mL/min. Back pressure: 100 bar. Column temperature: 38° C. Wavelength: 220 nm. Cycle time: ~8 min.

¹H-NMR

The NMR spectra were recorded on Bruker Avance III HD 500 MHz, Bruker Avance III 500 MHz, Bruker Avance III 400 MHz, Varian-400 VNMRS, or Varian-400 MR. Chemical shifts are expressed in parts per million (ppm) units. Coupling constants (J) are in units of hertz (Hz). Splitting patterns describe apparent multiplicities and are designated as s (single), d (double), t (triplet), dd (double doublet), dt (double triplet), dq (double quartet), m (multiplet), br (broad).

The following general reaction Schemes 1, 2, 3, and 4 provide useful details for preparing the instant compounds. The requisite intermediates are in some cases commercially available or can be prepared according to literature procedures. The illustrative reaction schemes are not limited by the compounds listed or by any particular substituents employed for illustrative purposes substituent labeling (i.e. R groups) as shown in the reaction schemes do not necessarily correlate to that used in the claims and often, for clarity, a single substituent is shown attached to the compound where multiple substituents are allowed under the definitions of Formula (I) hereinabove.

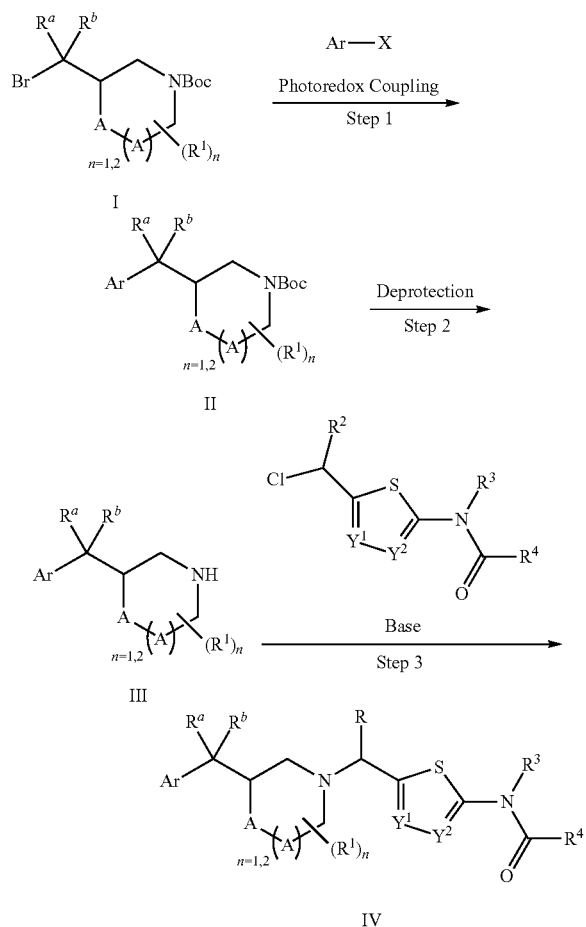

A = O, CH₂, CHR¹
independently substituted

Intermediate 1

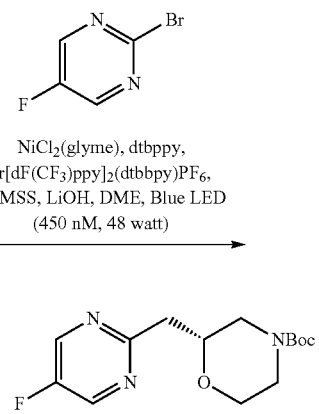

tert-butyl (R)-2-((5-fluoropyrimidin-2-yl)methyl)morpholine-4-carboxylate: A solution of NiCl₂(glyme) (0.039 g, 0.178 mmol), 4-tert-butyl-2-(4-tert-butyl-2-pyridyl)pyridine (0.048 g, 0.178 mmol), and Ir{dF(CF₃)ppy}₂(dtbpy)PF₆ (0.020 g, 0.018 mmol) in DME (8.9 mL) was sparged with N₂ for 15 min. The nickel solution was added to a mixture of tert-butyl (S)-2-(bromomethyl)morpholine-4-carboxylate (0.499 g, 1.78 mmol), 2-bromo-5-fluoro-pyrimidine (0.315 g, 1.78 mmol), tris(trimethylsilyl)silane (0.575 g, 2.31 mmol, 0.71 mL), and lithium hydroxide (0.170 g, 7.12 mmol). After the mixture was sparged with N₂ (15 min), the reaction was irradiated with blue LEDs (48 watts 450 hv) overnight. Celite was added to the reaction and the mixture was diluted with EtOAc and filtered. The organic layer was washed with NH₄Cl (aq), dried over MgSO4, filtered, and concentrated in vacuo. The residue was purified by silica gel chromatography (0-100% EtOAc:heptane) to afford the title compound (0.10 g, 19% yield). LCMS (ESI): [M+H (-t-Bu)] 242.

Intermediate 2

(R)-2-((5-fluoropyrimidin-2-yl)methyl)morpholine hydrochloride: A solution of HCl in dioxane (4.0 M, 0.840 mL, 3.36 mmol) was added to a solution of tert-butyl (R)-2-((5-fluoropyrimidin-2-yl)methyl)morpholine-4-carboxylate (0.100 g, 0.336 mmol) in CH₂Cl₂ (1.68 mL). After 2 h, the mixture was concentrated in vacuo to afford the title compound (0.078 g, 99% yield). LCMS (ESI): [M+H] 198.

Example 1-1

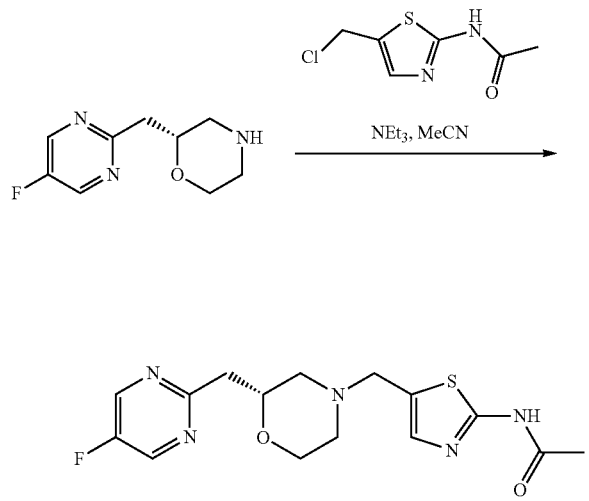

(R)—N-(5-((2-((5-fluoropyrimidin-2-yl)methyl)morpholino)methyl)thiazol-2-yl)acetamide: To a suspension of (R)-2-((5-fluoropyrimidin-2-yl)methyl)morpholine hydrochloride (0.039 g, 0.198 mmol) and N-[5-(chloromethyl)thiazol-2-yl]acetamide (0.040 g, 0.208 mmol) in acetonitrile (1.0 mL) was added triethylamine (0.082 mL, 0.593 mmol) and the mixture was warmed to 55° C. overnight. The reaction was cooled to room temperature, and the mixture was diluted with EtOAc and washed with saturated NH$_4$Cl (aq). The organics were dried over MgSO$_4$, filtered, and concentrated in vacuo. The residue was purified by silica gel chromatography (10-70% EtOAc:ethanol (3:1 v/v)/heptane) to provide the title compound (0.030 g 43% yield). LCMS: [M+H] 352. $^1$HNMR: (500 MHz, CDCl$_3$) δ12.09 (br s, 1H), 8.54 (s, 2H), 7.23 (s, 1H), 4.10-4.17 (m, 1H), 3.80-3.88 (m, 1H), 3.67-3.71 (m, 2H), 3.58-3.67 (m, 1H), 3.16 (dd, J=7.94, 14.04 Hz, 1H), 3.04 (dd, J=4.27, 14.04 Hz, 1H), 2.90 (br d, J=10.99 Hz, 1H), 2.71 (br d, J=10.99 Hz, 1H), 2.33 (s, 3H), 2.24 (dt, J=2.75, 11.14 Hz, 1H), 2.10 (br t, J=10.38 Hz, 1H).

Example 1-2

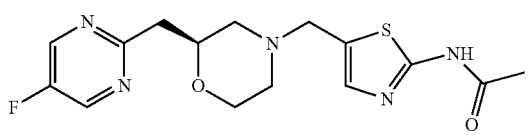 [SMILES: CC(=O)Nc1ncc(CN2CCO[C@@H](Cc3ncc(F)cn3)C2)s1]

(S)—N-(5-((2-((5-fluoropyrimidin-2-yl)methyl)morpholino)methyl)thiazol-2-yl)acetamide: The title compound was prepared in an analogous manner of that in scheme 1 from tert-butyl (R)-2-(bromomethyl)morpholine-4-carboxylate, 2-bromo-5-fluoro-pyrimidine, and N-[5-(chloromethyl)thiazol-2-yl]acetamide. LCMS (ESI): [M+H] 352. $^1$HNMR: (500 MHz, CDCl$_3$) δ11.87 (br s, 1H), 8.54 (s, 2H), 7.22 (s, 1H), 4.08-4.20 (m, 1H), 3.81-3.88 (m, 1H), 3.68 (s, 2H), 3.62 (dt, J=2.44, 11.29 Hz, 1H), 3.16 (dd, J=7.94, 14.04 Hz, 1H), 3.04 (dd, J=4.88, 14.04 Hz, 1H), 2.89 (br d, J=10.99 Hz, 1H), 2.65-2.74 (m, 1H), 2.32 (s, 3H), 2.23 (dt, J=3.36, 11.14 Hz, 1H), 2.08 (t, J=10.38 Hz, 1H).

Example 1-3

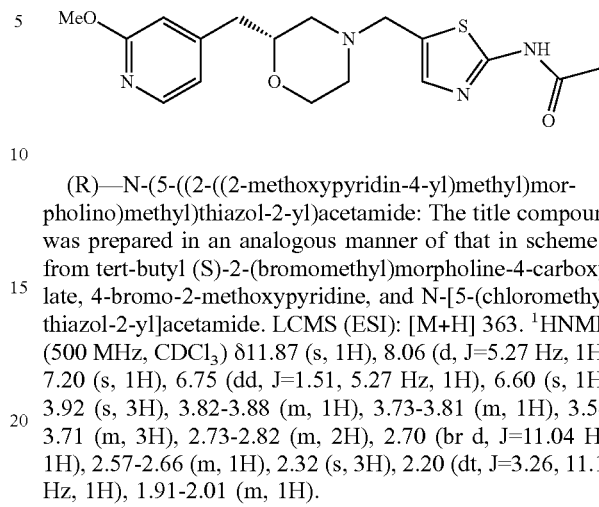

(R)—N-(5-((2-((2-methoxypyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2-methoxypyridine, and N-[5-(chloromethyl)thiazol-2-yl]acetamide. LCMS (ESI): [M+H] 363. $^1$HNMR: (500 MHz, CDCl$_3$) δ11.87 (s, 1H), 8.06 (d, J=5.27 Hz, 1H), 7.20 (s, 1H), 6.75 (dd, J=1.51, 5.27 Hz, 1H), 6.60 (s, 1H), 3.92 (s, 3H), 3.82-3.88 (m, 1H), 3.73-3.81 (m, 1H), 3.54-3.71 (m, 3H), 2.73-2.82 (m, 2H), 2.70 (br d, J=11.04 Hz, 1H), 2.57-2.66 (m, 1H), 2.32 (s, 3H), 2.20 (dt, J=3.26, 11.17 Hz, 1H), 1.91-2.01 (m, 1H).

Example 1-4

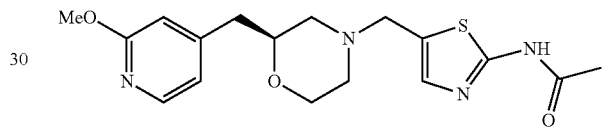

(S)—N-(5-((2-((2-methoxypyridin-4-yl)methyl)morpholino)methyl)thiazol-2-yl)acetamide: The title compound was prepared in an analogous manner of that in scheme 1 from tert-butyl (R)-2-(bromomethyl)morpholine-4-carboxylate, 4-bromo-2-methoxypyridine, and N-[5-(chloromethyl)thiazol-2-yl]acetamide. LCMS (ESI): [M+H] 363. $^1$HNMR: (500 MHz, CDCl$_3$) δ11.59 (br s, 1H), 8.06 (d, J=5.49 Hz, 1H), 7.20 (s, 1H), 6.75 (dd, J=1.22, 4.88 Hz, 1H), 6.60 (s, 1H), 3.92 (s, 3H), 3.82-3.87 (m, 1H), 3.75-3.81 (m, 1H), 3.59-3.69 (m, 3H), 2.73-2.81 (m, 2H), 2.70 (br d, J=10.99 Hz, 1H), 2.62 (dd, J=5.49, 14.04 Hz, 1H), 2.31 (s, 3H), 2.20 (dt, J=3.36, 11.14 Hz, 1H), 1.97 (t, J=10.38 Hz, 1H).

Example 1-5

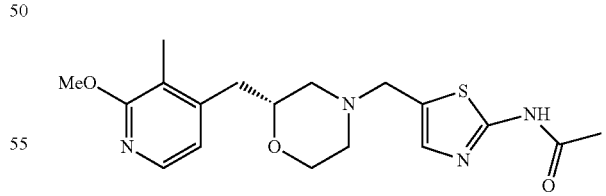

(R)—N-(5-((2-((2-methoxy-3-methylpyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2-methoxy-3-methylpyridine, and N-[5-(chloromethyl)thiazol-2-yl]acetamide. LCMS (ESI): [M+H] 377. $^1$HNMR: (500 MHz, CDCl$_3$) δ12.19 (br s, 1H), 7.90 (d, J=5.49 Hz, 1H), 7.20 (s, 1H), 6.70 (d, J=4.88 Hz, 1H), 3.94 (s, 3H), 3.81-3.88 (m, 1H), 3.72-3.80 (m, 1H), 3.56-3.71 (m, 3H), 2.83 (dd, J=7.33, 14.04 Hz, 1H), 2.75 (br d, J=10.99 Hz, 1H), 2.61-2.71 (m, 2H), 2.32 (s, 3H), 2.17-2.24 (m, 1H), 2.15 (s, 3H), 2.02 (t, J=10.38 Hz, 1H).

Example 1-6

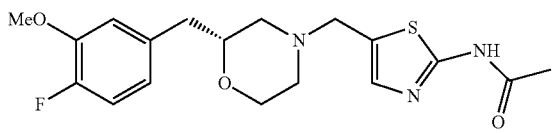 [SMILES: COc1cc(C[C@@H]2CN(Cc3cnc(NC(C)=O)s3)CCO2)ccc1F]

(R)—N-(5-((2-(4-fluoro-3-methoxybenzyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-1-fluoro-2-methoxybenzene, and N-[5-(chloromethyl)thiazol-2-yl]acetamide. LCMS (ESI): [M+H] 380. $^1$HNMR: (500 MHz, CDCl$_3$) δ $^1$H NMR (500 MHz, CDCl$_3$) δ11.88 (br s, 1H), 7.20 (s, 1H), 6.97 (dd, J=7.94, 10.99 Hz, 1H), 6.82 (dd, J=1.83, 7.94 Hz, 1H), 6.68-6.73 (m, 1H), 3.88 (s, 3H), 3.84-3.87 (m, 1H), 3.70-3.79 (m, 1H), 3.59-3.67 (m, 3H), 2.74-2.83 (m, 2H), 2.66-2.73 (m, 1H), 2.63 (dd, J=5.49, 14.04 Hz, 1H), 2.31 (s, 3H), 2.20 (dt, J=3.05, 11.29 Hz, 1H), 1.91-2.01 (m, 1H).

Example 1-7

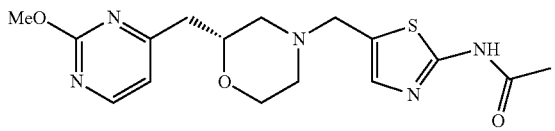 [SMILES: COc1nccc(C[C@@H]2CN(Cc3cnc(NC(C)=O)s3)CCO2)n1]

(R)—N-(5-((2-((2-methoxypyrimidin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-chloro-2-methoxypyrimidine, and N-[5-(chloromethyl)thiazol-2-yl]acetamide. LCMS (ESI): [M+H]364. $^1$HNMR: (500 MHz, CDCl$_3$) δ $^1$H NMR (500 MHz, CDCl$_3$) δ11.22 (br s, 1H), 8.39 (d, J=4.88 Hz, 1H), 7.21 (s, 1H), 6.86 (d, J=4.88 Hz, 1H), 4.00-4.07 (m, 1H), 3.99 (s, 3H), 3.79-3.88 (m, 1H), 3.67 (s, 2H), 3.61-3.66 (m, 1H), 2.82-2.93 (m, 2H), 2.74-2.80 (m, 1H), 2.71 (br d, J=10.99 Hz, 1H), 2.31 (s, 3H), 2.22 (dt, J=3.36, 11.14 Hz, 1H), 1.96-2.09 (m, 1H).

Example 1-8

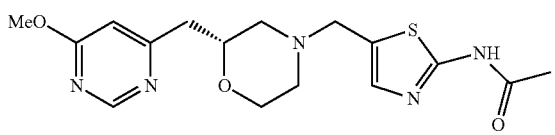 [SMILES: COc1cc(C[C@@H]2CN(Cc3cnc(NC(C)=O)s3)CCO2)ncn1]

(R)—N-(5-((2-((6-methoxypyrimidin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-chloro-6-methoxypyrimidine, and N-[5-(chloromethyl)thiazol-2-yl]acetamide. LCMS (ESI): [M+H]364. $^1$HNMR: (500 MHz, CDCl$_3$) δ11.59 (br s, 1H), 8.70 (s, 1H), 7.21 (s, 1H), 6.65 (s, 1H), 3.93-4.01 (m, 4H), 3.79-3.89 (m, 1H), 3.67 (d, J=2.44, 2H), 3.63 (dt, J=2.44, 11.29 Hz, 1H), 2.80-2.92 (m, 2H), 2.73-2.78 (m, 1H), 2.70 (br d, J=11.60 Hz, 1H), 2.31 (s, 3H), 2.21 (dt, J=3.36, 11.14 Hz, 1H), 2.04 (t, J=10.38 Hz, 1H).

Example 1-9

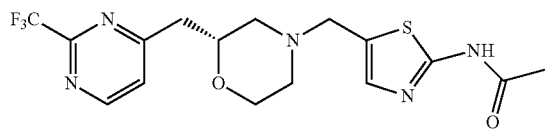 [SMILES: CC(=O)Nc1ncc(CN2CCO[C@H](Cc3ccnc(C(F)(F)F)n3)C2)s1]

(R)—N-(5-((2-(2-(trifluoromethyl)pyrimidin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-chloro-2-(trifluoromethyl)pyrimidine, and N-[5-(chloromethyl)thiazol-2-yl]acetamide. LCMS (ESI): [M+H] 402. $^1$HNMR: (500 MHz, CDCl$_3$) δ12.66 (br s, 1H), 8.75 (d, J=4.88 Hz, 1H), 7.44 (d, J=4.88 Hz, 1H), 7.21 (s, 1H), 3.94-4.03 (m, 1H), 3.80 (dd, J=1.53, 9.46 Hz, 1H), 3.64-3.73 (m, 2H), 3.60 (dt, J=2.44, 11.29 Hz, 1H), 2.91-3.03 (m, 2H), 2.88 (br d, J=10.99 Hz, 1H), 2.71 (br d, J=11.60 Hz, 1H), 2.33 (s, 3H), 2.22 (dt, J=3.36, 11.14 Hz, 1H), 1.97-2.08 (m, 1H).

Example 1-10

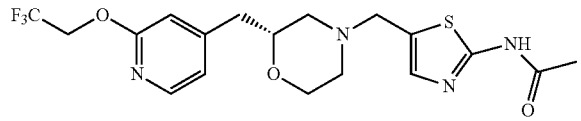 [SMILES: CC(=O)Nc1ncc(CN2CCO[C@H](Cc3ccnc(OCC(F)(F)F)c3)C2)s1]

(R)—N-(5-((2-(2-(2,2,2-trifluoroethoxy)pyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2-(2,2,2-trifluoroethoxy)pyridine, and N-[5-(chloromethyl)thiazol-2-yl]acetamide. LCMS (ESI): [M+H] 431. $^1$HNMR: (500 MHz, CDCl$_3$) δ11.55 (br s, 1H), 8.03 (d, J=4.88 Hz, 1H), 7.21 (s, 1H), 6.84 (dd, J=1.22, 5.49 Hz, 1H), 6.73 (s, 1H), 4.74 (q, J=8.95 Hz, 2H), 3.83-3.89 (m, 1H), 3.75-3.82 (m, 1H), 3.59-3.71 (m, 3H), 2.74-2.83 (m, 2H), 2.71 (br d, J=10.99 Hz, 1H), 2.62-2.68 (m, 1H), 2.31 (s, 3H), 2.21 (dt, J=3.05, 11.29 Hz, 1H), 1.98 (t, J=10.38 Hz, 1H).

Example 1-11

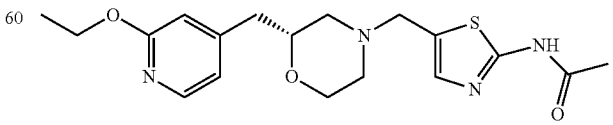

(R)—N-(5-((2-((2-ethoxypyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2-ethoxypyridine, and N-[5-(chloromethyl)thiazol-2-yl]acetamide. LCMS (ESI): [M+H] 377. ¹HNMR: (500 MHz, CDCl₃) δ11.47 (br s, 1H), 8.04 (d, J=4.88 Hz, 1H), 7.20 (s, 1H), 6.73 (dd, J=1.22, 5.49 Hz, 1H), 6.58 (s, 1H), 4.34 (q, J=7.33 Hz, 2H), 3.83-3.92 (m, 1H), 3.74-3.82 (m, 1H), 3.58-3.70 (m, 3H), 2.73-2.83 (m, 2H), 2.70 (br d, J=10.99 Hz, 1H), 2.61 (dd, J=5.49, 14.04 Hz, 1H), 2.31 (s, 3H), 2.19 (dt, J=3.05, 11.29 Hz, 1H), 1.97 (t, J=10.38 Hz, 1H), 1.39 (t, J=7.02 Hz, 3H).

Example 1-12

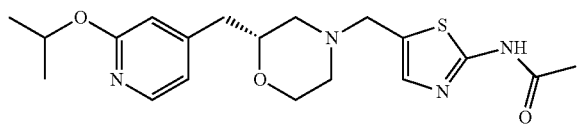 [SMILES: CC(=O)Nc1ncc(CN2CCO[C@H](Cc3ccnc(OC(C)C)c3)C2)s1]

(R)—N-(5-((2-((2-isopropoxypyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2-isopropoxypyridine, and N-[5-(chloromethyl)thiazol-2-yl]acetamide. LCMS (ESI): [M+H]391. ¹HNMR: (500 MHz, CDCl₃) δ11.50 (br s, 1H), 8.03 (d, J=5.49 Hz, 1H), 7.20 (s, 1H), 6.70 (dd, J=1.22, 5.49 Hz, 1H), 6.54 (s, 1H), 5.27 (spt, J=6.10 Hz, 1H), 3.83-3.89 (m, 1H), 3.75-3.81 (m, 1H), 3.59-3.71 (m, 3H), 2.67-2.82 (m, 3H), 2.60 (dd, J=5.49, 14.04 Hz, 1H), 2.31 (s, 3H), 2.19 (dt, J=3.66, 11.29 Hz, 1H), 1.97 (t, J=10.68 Hz, 1H), 1.34 (d, J=6.10 Hz, 6H).

Example 1-13

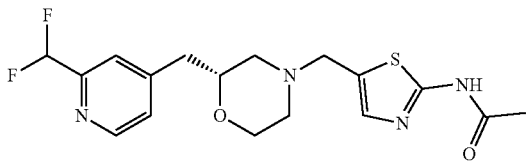 [SMILES: CC(=O)Nc1ncc(CN2CCO[C@H](Cc3ccnc(C(F)F)c3)C2)s1]

(R)—N-(5-((2-(2-(difluoromethyl)pyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2-(difluoromethyl)pyridine, and N-[5-(chloromethyl)thiazol-2-yl]acetamide. LCMS (ESI): [M+H] 383. ¹HNMR: (500 MHz, CDCl₃) δ11.62 (br s, 1H), 8.55 (d, J=4.88 Hz, 1H), 7.49 (s, 1H), 7.27-7.30 (m, 1H), 7.21 (s, 1H), 6.63 (t, J=54.33 Hz, 1H), 3.83-3.89 (m, 1H), 3.77-3.83 (m, 1H), 3.67 (s, 2H), 3.62 (dt, J=2.44, 11.29 Hz, 1H), 2.82-2.89 (m, 1H), 2.69-2.81 (m, 3H), 2.32 (s, 3H), 2.22 (dt, J=3.05, 11.29 Hz, 1H), 1.96-2.02 (m, 1H).

Example 1-14

(R)—N-(5-((2-((2-methylpyrimidin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-chloro-2-methylpyrimidine, and N-[5-(chloromethyl)thiazol-2-yl]acetamide. LCMS (ESI): [M+H] 348.

Example 1-15

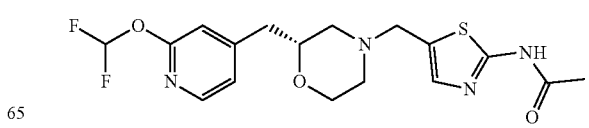

(R)—N-(5-((2-((3-fluoro-2-methoxypyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-3-fluoro-2-methoxypyridine, and N-[5-(chloromethyl)thiazol-2-yl]acetamide. LCMS (ESI): [M+H] 381. ¹HNMR: (500 MHz, CDCl₃) δ11.83 (br s, 1H), 7.82 (d, J=4.88 Hz, 1H), 7.21 (s, 1H), 6.79 (t, J=4.58 Hz, 1H), 4.01 (s, 3H), 3.75-3.89 (m, 2H), 3.58-3.72 (m, 3H), 2.73-2.88 (m, 3H), 2.69 (dd, J=1.53, 11.29 Hz, 1H), 2.32 (s, 3H), 2.20 (dt, J=3.36, 11.14 Hz, 1H), 2.01 (t, J=10.38 Hz, 1H).

Example 1-16

(R)—N-(5-((2-((5-methylpyridin-2-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 2-bromo-5-methylpyridine, and N-[5-(chloromethyl)thiazol-2-yl]acetamide. LCMS (ESI): [M+H] 347. ¹HNMR: (500 MHz, CDCl₃) δ11.45 (br s, 1H), 8.33 (d, J=1.83 Hz, 1H), 7.44 (dd, J=2.44, 7.94 Hz, 1H), 7.20 (s, 1H), 7.09 (d, J=7.94 Hz, 1H), 3.84 (br d, J=11.60 Hz, 1H), 3.67-3.75 (m, 1H), 3.65 (d, J=3.05 Hz, 2H), 3.57-3.63 (m, 1H), 2.72-2.82 (m, 2H), 2.69 (br d, J=11.60 Hz, 1H), 2.62-2.67 (m, 1H), 2.53 (s, 3H), 2.31 (s, 3H), 2.19 (dt, J=3.05, 11.29 Hz, 1H), 1.97 (t, J=10.38 Hz, 1H).

Example 1-17

(R)—N-(5-((2-((2-(difluoromethoxy)pyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2-(difluoromethoxy)pyridine, and N-[5-(chloromethyl)thiazol-2-yl]acetamide. LCMS (ESI): [M+H] 399. ¹HNMR: (500 MHz, CDCl₃) δ11.21 (br s, 1H), 8.08 (d, J=5.49 Hz, 1H), 7.45 (t, J=72.60 Hz, 1H), 7.21 (s, 1H), 6.96 (dd, J=1.53, 5.19 Hz, 1H), 6.77 (s, 1H), 3.82-3.90 (m, 1H), 3.74-3.81 (m, 1H), 3.66 (s, 2H), 3.62 (dt, J=2.44, 11.29 Hz, 1H), 2.66-2.85 (m, 4H), 2.31 (s, 3H), 2.22 (dt, J=3.66, 11.29 Hz, 1H), 1.98 (dd, J=9.77, 10.99 Hz, 1H).

Example 1-18

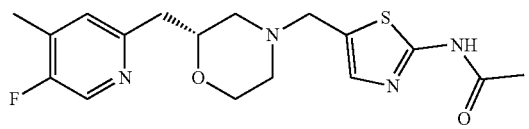 [SMILES: CC(=O)Nc1ncc(CN2CCO[C@H](Cc3cc(C)c(F)cn3)C2)s1]

(R)—N-(5-((2-((5-fluoro-4-methylpyridin-2-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 2-chloro-5-fluoro-4-methylpyridine, and N-[5-(chloromethyl)thiazol-2-yl]acetamide. LCMS (ESI): [M+H] 365.

Example 1-19

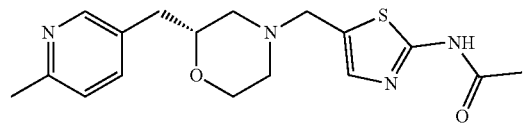 [SMILES: CC(=O)Nc1ncc(CN2CCO[C@H](Cc3ccc(C)nc3)C2)s1]

(R)—N-(5-((2-((6-methylpyridin-3-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 5-bromo-2-methylpyridine, and N-[5-(chloromethyl)thiazol-2-yl]acetamide. LCMS (ESI): [M+H] 347. ¹HNMR: (500 MHz, CDCl₃) 12.03 (br s, 1H), 8.33 (d, J=1.83 Hz, 1H), 7.44 (dd, J=2.44, 7.94 Hz, 1H), 7.20 (s, 1H), 7.08 (d, J=7.94 Hz, 1H), 3.80-3.88 (m, 1H), 3.67-3.75 (m, 1H), 3.64 (d, J=2.44 Hz, 2H), 3.57-3.63 (m, 1H), 2.72-2.83 (m, 2H), 2.69 (dd, J=1.22, 10.99 Hz, 1H), 2.62-2.67 (m, 1H), 2.52 (s, 3H), 2.31 (s, 3H), 2.18 (dt, J=3.05, 11.29 Hz, 1H), 1.91-2.01 (m, 1H).

Example 1-20

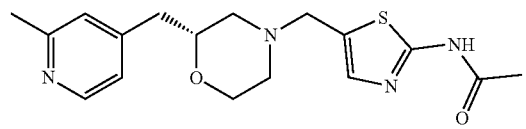 [SMILES: CC(=O)Nc1ncc(CN2CCO[C@H](Cc3ccnc(C)c3)C2)s1]

(R)—N-(5-((2-((2-methylpyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2-methylpyridine, and N-[5-(chloromethyl)thiazol-2-yl]acetamide. LCMS (ESI): [M+H] 347. ¹HNMR: (500 MHz, CDCl₃) δ11.60 (br s, 1H), 8.39 (d, J=4.88 Hz, 1H), 7.20 (s, 1H), 7.01 (s, 1H), 6.95 (d, J=4.88 Hz, 1H), 3.83-3.90 (m, 1H), 3.75-3.81 (m, 1H), 3.59-3.69 (m, 3H), 2.67-2.83 (m, 3H), 2.63 (dd, J=4.88, 14.04 Hz, 1H), 2.53 (s, 3H), 2.31 (s, 3H), 2.21 (dt, J=3.36, 11.14 Hz, 1H), 1.97 (t, J=10.38 Hz, 1H).

Example 1-21

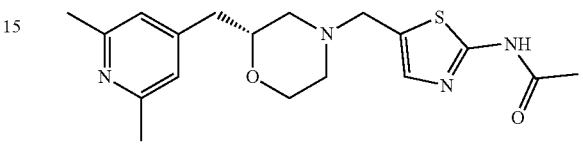

(R)—N-(5-((2-((2,6-dimethylpyridin-4-yl)methyl)morpholino)methyl)thiazol-2-yl)acetamide: The title compound was prepared in an analogous manner of that in scheme 1 from tert-butyl (S)-2-(bromomethyl)morpholine-4-carboxylate, 4-bromo-2,6-dimethylpyridine, and N-15-(chloromethyl)thiazol-2-yl)acetamide. LCMS (ESI): [M+H] 361. ¹HNMR: (500 MHz, CDCl₃) δ11.39 (br s, 1H), 7.20 (s, 1H), 6.82 (s, 2H), 3.82-3.91 (m, 1H), 3.75-3.80 (m, 1H), 3.59-3.69 (m, 3H), 2.67-2.79 (m, 3H), 2.58 (dd, J=5.49, 14.04 Hz, 1H), 2.49 (s, 6H), 2.31 (s, 3H), 2.21 (dt, J=3.36, 11.14 Hz, 1H), 1.97 (dd, J=9.77, 10.99 Hz, 1H).

Example 1-22

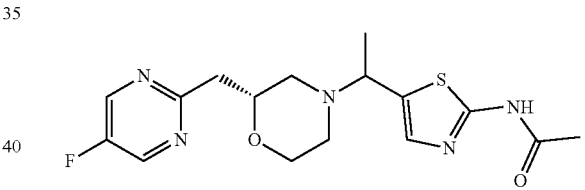

N-(5-(-1-((R)-2-((5-fluoropyrimidin-2-yl)methyl)morpholino)ethyl)thiazol-2-yl)acetamide: The title compound was prepared in an analogous manner of that in scheme 1 from tert-butyl (S)-2-(bromomethyl)morpholine-4-carboxylate, 2-bromo-5-fluoro-pyrimidine, and N-(5-(1-chloroethyl)thiazol-2-yl)acetamide.

Example 1-23

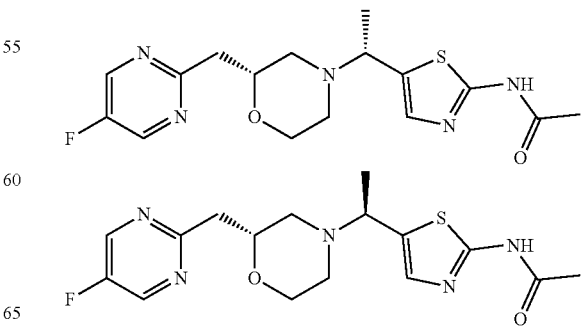

The resulting mixture of diastereomers from Example 1-22, namely N-(5-((R)-1-((R)-2-((5-fluoropyrimidin-2-yl)methyl)morpholino)ethyl)thiazol-2-yl)acetamide and N-(5-((S)-1-((R)-2-((5-fluoropyrimidin-2-yl)methyl)morpholino)ethyl)thiazol-2-yl)acetamide, was separated using the following conditions: Column: CHIRALPAK AD-H 30×250 mm, 5 um. Method: 30% Isopropanol with 0.1% diethyl amine in CO₂ (flow rate: 100 mL/min), ABPR 120 bar, MBPR 60 psi, as:

Peak 1: LCMS (ESI): [M+H] 366. LCMS (ESI): [M+H] 366.

Peak 2: LCMS (ESI): [M+H] 366.

Intermediate 3

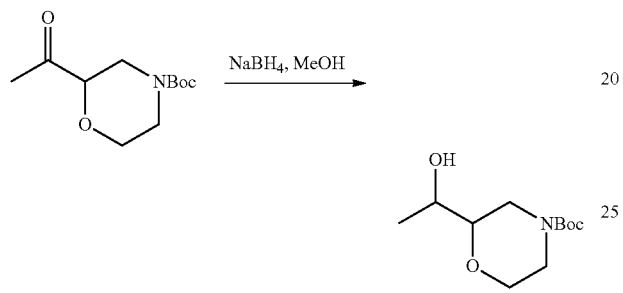

tert-butyl 2-(1-hydroxyethyl)morpholine-4-carboxylate: To a solution of tert-butyl 2-acetylmorpholine-4-carboxylate (1.01 g, 4.40 mmol) in ethanol (22.00 mL) was added sodium borohydride (0.250 mg, 6.60 mmol) and the mixture was stirred at room temperature for 1 hr. The reaction mixture was concentrated under reduced pressure, and the residue was diluted with water. The mixture was treated with 5% aqueous sodium hydrogen sulfate solution and extracted with ethyl acetate. The extract was washed with water, brine, dried over Na₂SO₄, filtered and concentrated in vacuo to provide the title compound (1.00 g, 98% yield).

Intermediate 4

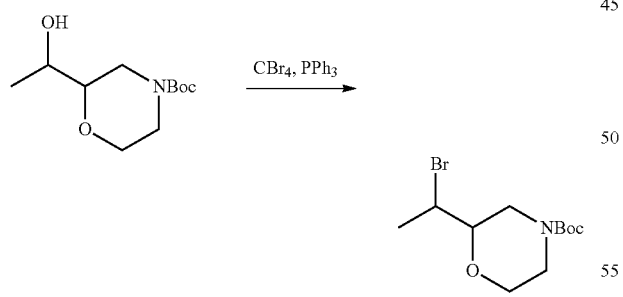

tert-butyl 2-(1-bromoethyl)morpholine-4-carboxylate: To a stirred solution of tert-butyl 2-(1-hydroxyethyl)morpholine-4-carboxylate (1.00 g, 4.40 mmol), triphenylphosphine (2.54 g, 9.68 mmol), and pyridine (1.74 g, 22.0 mmol) in acetonitrile (22.0 mL) was added a solution of tetrabromomethane (3.21 g, 9.68 mmol) in acetonitrile (22.0 mL). The resulting reaction mixture was stirred at room temperature for 16 h. To the reaction mixture was added Et₂O (100 mL) and the resulting precipitate was removed by filtration. The filtrate was washed with water and brine, dried over MgSO₄, filtered, and concentrated in vacuo. The residue was purified over SiO₂ (0-50% EtOAc:heptane) to afford the title compound (0.54 g, 41% yield). LCMS (ESI): [M+H (-tBu)] 238.

Example 1-24

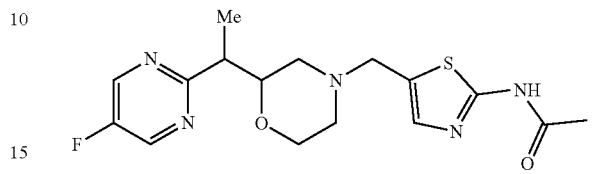

N-(5-((2-(1-(5-fluoropyrimidin-2-yl)ethyl)morpholino)methyl)thiazol-2-yl)acetamide; The title compound was prepared in an analogous manner of that in scheme 1 from tert-butyl 2-(1-bromoethyl)morpholine-4-carboxylate, 2-bromo-5-fluoro-pyrimidine, and N-[5-(chloromethyl)thiazol-2-yl]acetamide.

Example 1-25

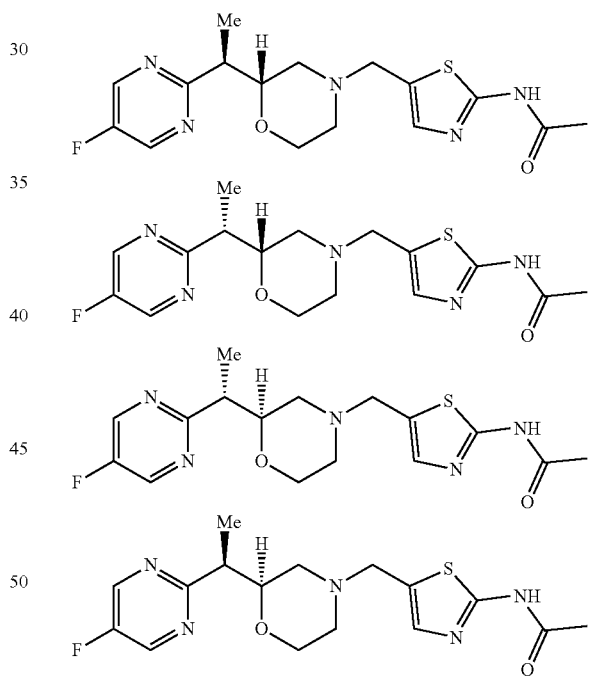

The resulting mixture of diastereomers and enantiomers, from Example 1-24, namely N-(5-(((R)-2-((R)-1-(5-fluoropyrimidin-2-yl)ethyl)morpholino)methyl)thiazol-2-yl)acetamide, N-(5-4(R)-2-((S)-1-(5-fluoropyrimidin-2-yl)ethyl)morpholino)methyl)thiazol-2-yl)acetamide, N-(5-(((S)-2-((S)-1-(5-fluoropyrimidin-2-yl)ethyl)morpholino)methyl)thiazol-2-yl)acetamide and N-(5-(((S)-2-((R)-1-(5-fluoropyrimidin-2-yl)ethyl)morpholino)methyl)thiazol-2-yl)acetamide, was separated using the following conditions: Column: CHIRALPAK AD-H 30×250 mm, 5 um. Method: 30% Isopropanol with 0.1% diethyl amine in CO₂ (flow rate: 100 mL/min), ABPR 120 bar, MBPR 60 psi, as:

Peak 1: LCMS (ESI): [M+H] 366. $^1$H NMR: (500 MHz, METHANOL-d$_4$) δ8.64 (s, 2H), 7.16 (s, 1H), 3.88 (ddd, J=1.83, 3.36, 11.29 Hz, 1H), 3.81-3.86 (m, 1H), 3.60-3.66 (m, 1H), 3.60 (d, J=1.22 Hz, 2H), 3.11-3.21 (m, 1H), 2.66-2.71 (m, 1H), 2.41-2.46 (m, 1H), 2.19 (s, 3H), 2.14-2.18 (m, 1H), 1.92 (dd, J=9.77, 11.60 Hz, 1H), 1.36 (d, J=7.33 Hz, 3H).

Peak 2: LCMS (ESI): [M+H] 366. $^1$H NMR: (500 MHz, METHANOL-d$_4$) δ8.64 (s, 2H), 7.16 (s, 1H), 3.86-3.91 (m, 1H), 3.81-3.86 (m, 1H), 3.58-3.66 (m, 3H), 3.15 (dd, J=7.02, 8.24 Hz, 1H), 2.64-2.73 (m, 1H), 2.41-2.46 (m, 1H), 2.19 (s, 3H), 2.13-2.22 (m, 1H), 1.92 (dd, J=9.77, 11.60 Hz, 1H), 1.36 (d, J=7.33 Hz, 3H).

Peak 3: LCMS (ESI): [M+H] 366. $^1$H NMR: (500 MHz, METHANOL-d$_4$) δ8.65 (s, 2H), 7.26 (s, 1H), 3.89-3.93 (m, 1H), 3.65-3.79 (m, 3H), 3.48 (dt, J=2.44, 11.29 Hz, 1H), 3.15-3.25 (m, 1H), 2.98-3.05 (m, 1H), 2.67 (dd, J=1.83, 10.99 Hz, 1H), 2.20 (s, 3H), 2.14-2.20 (m, 1H), 2.05 (dd, J=10.07, 11.29 Hz, 1H), 1.22 (d, J=7.33 Hz, 3H).

Peak 4: LCMS (ESI): [M+H] 366. $^1$H NMR: (500 MHz, METHANOL-d$_4$) δ8.65 (s, 2H), 7.26 (s, 1H), 3.88-3.96 (m, 1H), 3.66-3.79 (m, 3H), 3.48 (dt, J=2.44, 11.29 Hz, 1H), 3.15-3.24 (m, 1H), 3.02 (d, J=10.99 Hz, 1H), 2.67 (dd, J=1.83, 11.60 Hz, 1H), 2.20 (s, 3H), 2.14-2.19 (m, 1H), 2.05 (dd, J=9.77, 10.99 Hz, 1H), 1.22 (d, J=7.33 Hz, 3H).

Intermediate 5

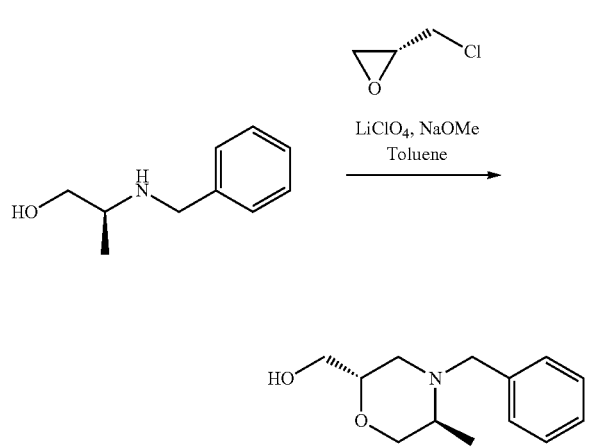

((2S,5S)-4-benzyl-5-methylmorpholin-2-yl)methanol: (S)-2-(benzylamino)propan-1-ol (3.0 g) was dissolved in toluene (57.6 mL) and (2R)-2-(chloromethyl)oxirane (2.50 g, 27.1 mmol, 2.12 mL) was added. Lithium perchlorate (2.88 g, 27.1 mmol) was added and the mixture was stirred at room temperature for 16 h. NaOH (2.14 g, 53.6 mmol) was dissolved in methanol (30 mL) and the mixture was added slowly and stirred at room temperature for 36 h. The reaction was concentrated, dissolved in CH$_2$Cl$_2$, and water was added. The layers were separated and the organics were dried over Na$_2$SO$_4$ and concentrated in vacuo. The residue was purified by silica gel chromatography (0-5% CH$_2$Cl$_2$:MeOH) to afford the title compound (3.70 g, 92% yield). LCMS (ESI): [M+H] 222. $^1$HNMR: (500 MHz, CDCl$_3$) δ7.24-7.35 (m, 5H), 3.75-3.83 (m, 1H), 3.51-3.63 (m, 2H), 3.30-3.49 (m, 5H), 2.58 (dd, J=11.6, 2.4 Hz, 1H), 2.40 (ddd, J=9.9, 6.3, 3.4 Hz, 1H), 1.09 (d, J=6.1 Hz, 3H).

Intermediate 6

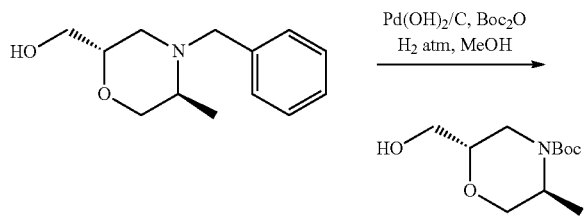

tert-butyl (2S,5S)-2-(hydroxymethyl)-5-methylmorpholine-4-carboxylate: ((2S,5S)-4-benzyl-5-methylmorpholin-2-yl)methanol (3.70 g, 16.72 mmol) was dissolved in methanol (100.0 mL). Palladium hydroxide on carbon (1.88 g, 2.68 mmol, 20% w/w) was added followed by Boc anhydride (3.65 g, 16.7 mmol). The reaction was stirred under an atmosphere of H$_2$ for 16 h. The reaction was filtered over celite and concentrated in vacuo. The residue was purified by silica gel chromatography (0-10% CH$_2$Cl$_2$:MeOH) to afford the title compound (2.32 g, 59% yield). $^1$HNMR: (500 MHz, CDCl$_3$) δ4.03 (br d, J=6.7 Hz, 1H), 3.78-3.94 (m, 3H), 3.65 (dd, J=14.0, 2.4 Hz, 1H), 3.56 (s, 1H), 3.33-3.48 (m, 3H), 1.45-1.47 (m, 9H), 1.24 (d, J=6.7 Hz, 3H).

Intermediate 7

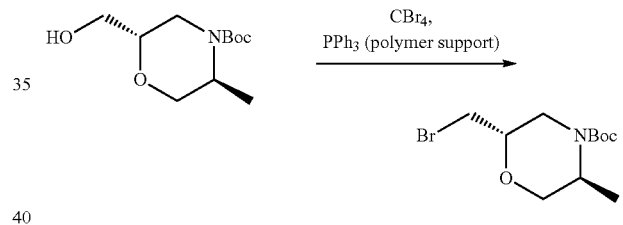

tert-butyl (2S,5S)-2-(bromomethyl)-5-methylmorpholine-4-carboxylate: tert-Butyl (2S,5S)-2-(hydroxymethyl)-5-methylmorpholine-4-carboxylate (939 mg, 4.06 mmol) was dissolved in CH$_2$Cl$_2$ (16.2 mL). The mixture was cooled to 0° C. and triphenylphosphine (polymer supported) (3.19 g, 12.2 mmol) was added followed by carbon tetrabromide (2.69 g, 8.12 mmol). The reaction was allowed to reach ambient temperature and was stirred at room temperature for 16 h. The reaction was filtered over a pad of silica and celite and concentrated in vacuo. The residue was purified by silica gel chromatography (0-50% EtOAc:heptane) to afford the title compound (405 mg, 33% yield). LCMS (ESI): [M-Boc]$^+$ 194. $^1$HNMR: (500 MHz, CDCl$_3$) δ4.08 (dt, J=6.9, 3.6 Hz, 1H), 3.89-4.00 (m, 2H), 3.83 (dd, J=11.9, 4.0 Hz, 1H), 3.47-3.55 (m, 2H), 3.37-3.42 (m, 2H), 1.46-1.49 (m, 9H), 1.24 (d, J=6.7 Hz, 3H)

Intermediate 8

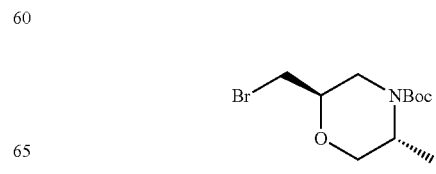

tert-butyl (2R,5R)-2-(bromomethyl)-5-methylmorpholine-4-carboxylate: The title compound was prepared in an analogous manner to that of intermediate 7 from (2S)-2-(benzylamino)propan-1-ol and (2S)-2-(chloromethyl)oxirane. LCMS (ESI): [M-Boc)] 194. ¹HNMR: (500 MHz, CDCl₃) δ4.08 (dt, J=6.7, 3.4 Hz, 1H), 3.96-4.00 (m, 1H), 3.92 (d, J=1.8 Hz, 1H), 3.90 (d, J=1.8 Hz, 1H), 3.83 (dd, J=11.9, 4.0 Hz, 1H), 3.47-3.54 (m, 2H), 3.37-3.41 (m, 2H), 1.46-1.55 (m, 9H), 1.24 (d, J=7.3 Hz, 3H).

Intermediate 9

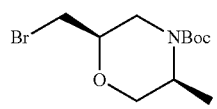 [SMILES: C[C@H]1CO[C@@H](CBr)CN1C(=O)OC(C)(C)C]

tert-butyl (2R,5S)-2-(bromomethyl)-5-methylmorpholine-4-carboxylate: The title compound was prepared in an analogous manner to that of intermediate 7 from (2S)-2-(benzylamino)propan-1-ol and (2S)-2-(chloromethyl)oxirane. LCMS (ESI): [M-Boc)] 194. ¹HNMR: (500 MHz, CDCl₃) δ4.12 (br d, J=7.3 Hz, 1H), 3.81-4.03 (m, 2H), 3.66-3.77 (m, 2H), 3.46-3.60 (m, 1H), 3.35-3.42 (m, 2H), 1.59 (s, 1H), 1.44-1.49 (m, 9H), 1.19-1.34 (m, 3H).

Intermediate 10

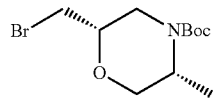 [SMILES: C[C@@H]1CO[C@H](CBr)CN1C(=O)OC(C)(C)C]

tert-butyl (2S,5R)-2-(bromomethyl)-5-methylmorpholine-4-carboxylate: The title compound was prepared in an analogous manner to that of intermediate 7 from (2R)-2-(benzylamino)propan-1-ol and (2R)-2-(chloromethyl)oxirane. LCMS (ESI): [M-Boc)] 194. ¹HNMR: (500 MHz, CDCl₃) δ4.12 (br d, J=7.3 Hz, 1H), 3.99 (br s, 1H), 3.67-3.86 (m, 2H), 3.56 (br s, 1H), 3.35-3.41 (m, 2H), 2.86 (br s, 1H), 1.59 (s, 1H), 1.55 (s, 1H), 1.45-1.51 (m, 9H), 1.23 (d, J=6.7 Hz, 3H).

Example 1-26

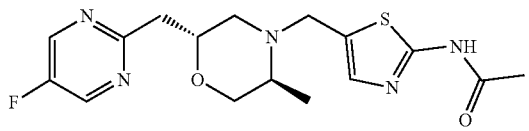 [SMILES: CC(=O)Nc1ncc(CN2C[C@@H](Cc3ncc(F)cn3)OC[C@@H]2C)s1]

N-(5-4(2R,5S)-2-((5-fluoropyrimidin-2-yl)methyl)-5-methylmorpholino)methyl)thiazol-2-yl)acetamide: The title compound was prepared in an analogous manner of that in scheme 1 from tert-butyl (2S,5S)-2-(bromomethyl)-5-methylmorpholine-4-carboxylate, 2-bromo-5-fluoro-pyrimidine, and N-[5-(chloromethyl)thiazol-2-yl]acetamide. LCMS (ESI): [M+H] 366. ¹HNMR: (500 MHz, CDCl₃) δ 10.95 (br s, 1H), 8.51 (s, 2H), 7.27-7.38 (m, 1H), 7.20 (s, 1H), 5.30 (s, 1H), 4.05-4.13 (m, 2H), 3.68 (dd, J=11.0, 3.1 Hz, 1H), 3.58-3.63 (m, 1H), 3.23 (t, J=11.0 Hz, 1H), 3.09 (dd, J=14.0, 8.5 Hz, 1H), 2.99 (dd, J=14.3, 4.6 Hz, 1H), 2.83 (dd, J=11.3, 2.1 Hz, 1H), 2.44 (ddd, J=9.9, 6.3, 3.4 Hz, 1H), 2.31 (s, 3H), 2.12-2.17 (m, 1H), 1.56 (s, 1H), 1.04-1.09 (m, 4H).

Example 1-27

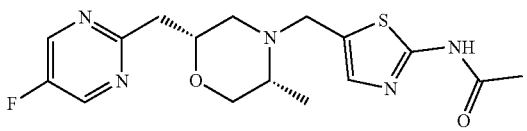 [SMILES: CC(=O)Nc1ncc(CN2C[C@@H](Cc3ncc(F)cn3)OC[C@H]2C)s1]

N-(5-4(2R,5R)-2-((5-fluoropyrimidin-2-yl)methyl)-5-methylmorpholino)methyl)thiazol-2-yl)acetamide: The title compound was prepared in an analogous manner of that in scheme 1 from tert-butyl (2S,5R)-2-(bromomethyl)-5-methylmorpholine-4-carboxylate, 2-bromo-5-fluoro-pyrimidine, and N-[5-(chloromethyl)thiazol-2-yl]acetamide. LCMS (ESI): [M+H] 366. ¹HNMR: (500 MHz, METHANOL-d₄) δ8.65 (s, 2H), 7.24 (s, 1H), 4.17 (dd, J=4.9, 3.7 Hz, 1H), 3.79-3.84 (m, 1H), 3.73-3.78 (m, 1H), 3.58-3.70 (m, 3H), 3.25 (dd, J=14.0, 7.9 Hz, 1H), 3.07 (dd, J=14.0, 5.5 Hz, 1H), 2.77-2.82 (m, 1H), 2.53-2.61 (m, 2H), 2.21 (s, 3H), 1.30 (s, 1H), 1.11 (d, J=6.7 Hz, 3H).

Example 1-28

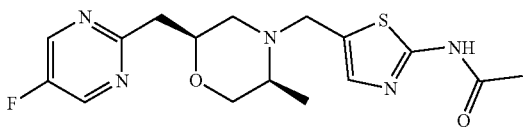 [SMILES: CC(=O)Nc1ncc(CN2C[C@H](Cc3ncc(F)cn3)OC[C@@H]2C)s1]

N-(5-(((2S,5S)-2-((5-fluoropyrimidin-2-yl)methyl)-5-methylmorpholino)methyl)thiazol-2-yl)acetamide: The title compound was prepared in an analogous manner of that in scheme 1 from tert-butyl (2R,5S)-2-(bromomethyl)-5-methylmorpholine-4-carboxylate, 2-bromo-5-fluoro-pyrimidine, and N-[5-(chloromethyl)thiazol-2-yl]acetamide. LCMS (ESI): [M+H] 366. ¹HNMR: (500 MHz, CDCl₃) δ 10.76 (br s, 1H), 8.52 (s, 2H), 7.20 (s, 1H), 5.30 (s, 1H), 4.10-4.17 (m, 1H), 3.61-3.77 (m, 4H), 3.24-3.43 (m, 1H), 3.02 (dd, J=14.0, 4.3 Hz, 1H), 2.77-2.84 (m, 1H), 2.53-2.58 (m, 2H), 2.29 (s, 3H), 2.04 (s, 1H), 1.55 (s, 1H), 1.26 (t, J=7.0 Hz, 1H), 1.08 (d, J=6.7 Hz, 3H).

Example 1-29

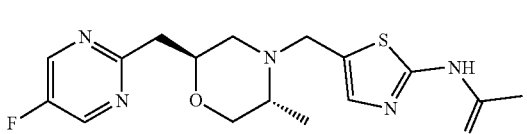

N-(5-(((2S,5R)-2-((5-fluoropyrimidin-2-yl)methyl)-5-methylmorpholino)methyl)thiazol-2-yl)acetamide: The title compound was prepared in an analogous manner of that in scheme 1 from tert-butyl (2R,5R)-2-(bromomethyl)-5-methylmorpholine-4-carboxylate, 2-bromo-5-fluoro-pyrimidine, and N-[5-(chloromethyl)thiazol-2-yl]acetamide. LCMS (ESI): [M+H] 366. ¹HNMR: (500 MHz, CDCl₃) δ11.44 (br s, 1H), 8.51 (s, 2H), 7.20 (s, 1H), 4.05-4.14 (m, 2H), 3.68 (dd, J=11.3, 3.4 Hz, 1H), 3.60 (d, J=14.0 Hz, 1H), 3.20-3.26 (m, 1H), 3.09 (dd, J=14.0, 8.5 Hz, 1H), 2.99 (dd, J=14.0, 4.3 Hz, 1H), 2.84 (dd, J=11.6, 1.8 Hz, 1H), 2.40-2.47 (m, 1H), 2.32 (s, 3H), 2.14 (dd, J=11.6, 10.4 Hz, 1H), 2.04 (s, 1H), 1.58 (br s, 1H), 1.22-1.32 (m, 2H), 1.05 (d, J=6.1 Hz, 3H)

Example 1-30

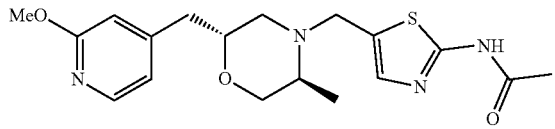 [SMILES: COc1cc(C[C@@H]2CN(Cc3cnc(NC(C)=O)s3)[C@@H](C)CO2)ccn1]

N-(5-(((2R,5S)-2-((2-methoxypyridin-4-yl)methyl)-5-methylmorpholino)methyl)thiazol-2-yl)acetamide: The title compound was prepared in an analogous manner of that in scheme 1 from tert-butyl (2S,5S)-2-(bromomethyl)-5-methylmorpholine-4-carboxylate, 4-bromo-2-methoxypyridine, and N-[5-(chloromethyl)thiazol-2-yl]acetamide. LCMS (ESI): [M+H] 377. ¹HNMR: (500 MHz, CDCl₃) δ11.57 (br s, 1H), 8.03 (d, J=5.5 Hz, 1H), 7.17-7.25 (m, 1H), 6.74 (d, J=5.4 Hz, 1H), 6.59 (s, 1H), 3.89-3.94 (m, 3H), 3.62-3.81 (m, 6H), 2.77-2.85 (m, 2H), 2.67 (dd, J=14.3, 5.2 Hz, 1H), 2.38-2.46 (m, 2H), 2.29 (s, 3H), 1.06 (d, J=6.7 Hz, 3H)

Example 1-31

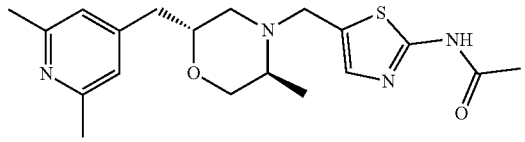 [SMILES: CC(=O)Nc1ncc(CN2C[C@@H](Cc3cc(C)nc(C)c3)OC[C@@H]2C)s1]

N-(5-4(2R,5S)-2-((2,6-dimethylpyridin-4-yl)methyl)-5-methylmorpholino)methyl)thiazol-2-yl)acetamide: The title compound was prepared in an analogous manner of that in scheme 1 from tert-butyl (2S,5S)-2-(bromomethyl)-5-methylmorpholine-4-carboxylate, 4-bromo-2,6-dimethylpyridine, and N-[5-(chloromethyl)thiazol-2-yl]acetamide. LCMS (ESI): [M+H] 375. ¹HNMR: (500 MHz, CDCl₃) δ12.12-12.33 (m, 1H), 7.19 (s, 1H), 6.79 (s, 2H), 4.06 (d, J=14.7 Hz, 1H), 3.74-3.79 (m, 1H), 3.60 (d, J=14.7 Hz, 1H), 3.24 (t, J=10.7 Hz, 1H), 2.62-2.75 (m, 2H), 2.50-2.60 (m, 1H), 2.47 (s, 6H), 2.34-2.45 (m, 1H), 2.32 (s, 3H), 2.01-2.08 (m, 2H), 1.06 (d, J=6.1 Hz, 3H)

Example 1-32

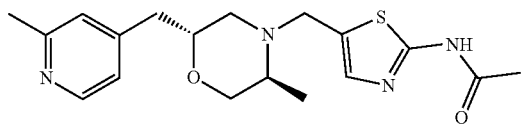 [SMILES: CC(=O)Nc1ncc(CN2C[C@@H](Cc3ccnc(C)c3)OC[C@@H]2C)s1]

N-(5-(((2R,5S)-5-methyl-2-((2-methylpyridin-4-yl)methyl)morpholino)methyl)thiazol-2-yl)acetamide: The title compound was prepared in an analogous manner of that in scheme 1 from tert-butyl (2S,5S)-2-(bromomethyl)-5-methylmorpholine-4-carboxylate, 4-bromo-2-methylpyridine, and N-[5-(chloromethyl)thiazol-2-yl]acetamide. LCMS (ESI): [M+H] 361. ¹HNMR: (500 MHz, CDCl₃) δ12.06 (br s, 1H), 8.23 (d, J=5.5 Hz, 1H), 7.05 (s, 1H), 6.85 (s, 1H), 6.79 (d, J=4.9 Hz, 1H), 3.91-4.01 (m, 1H), 3.59-3.66 (m, 1H), 3.57 (dd, J=11.6, 3.1 Hz, 1H), 3.46 (d, J=14.7 Hz, 1H), 3.10 (t, J=10.7 Hz, 1H), 2.50-2.64 (m, 2H), 2.41-2.50 (m, 1H), 2.37 (s, 3H), 2.29 (ddd, J=9.9, 6.3, 3.4 Hz, 1H), 2.19 (s, 3H), 1.83-1.98 (m, 2H), 1.04-1.21 (m, 1H), 0.93 (d, J=6.1 Hz, 3H)

Example 1-33

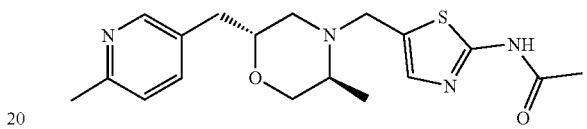

N-(5-(((2R,5S)-5-methyl-2-((6-methylpyridin-3-yl)methyl)morpholino)methyl)thiazol-2-yl)acetamide: The title compound was prepared in an analogous manner of that in scheme 1 from tert-butyl (2S,5S)-2-(bromomethyl)-5-methylmorpholine-4-carboxylate, 5-bromo-2-methylpyridine, and N-[5-(chloromethyl)thiazol-2-yl]acetamide. LCMS (ESI): [M+H] 361. ¹HNMR: (500 MHz, CDCl₃) δ2.33 (br s, 1H), 12.27 (br s, 1H), 8.30 (d, J=2.4 Hz, 1H), 7.41 (dd, J=7.9, 2.4 Hz, 1H), 7.19 (s, 1H), 7.06 (d, J=7.9 Hz, 1H), 4.05 (d, J=14.7 Hz, 1H), 3.66-3.72 (m, 2H), 3.60 (d, J=14.7 Hz, 1H), 3.21 (t, J=11.0 Hz, 1H), 2.58-2.75 (m, 3H), 2.50-2.55 (m, 3H), 2.38-2.45 (m, 1H), 2.29-2.38 (m, 1H), 2.01-2.09 (m, 2H), 1.05 (d, J=6.1 Hz, 3H)

Intermediate 11

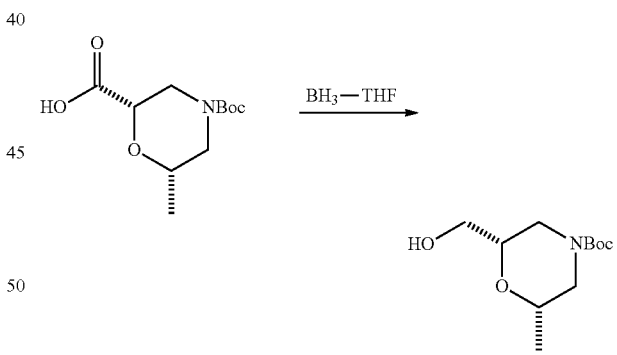

tert-butyl cis-2-(hydroxymethyl)-6-methylmorpholine-4-carboxylate: cis-4-(tert-Butoxycarbonyl)-6-methylmorpholine-2-carboxylic acid (0.75 g, 3.06 mmol) was dissolved in THF (10.0 mL) and cooled to 0° C. A solution of BH₃-THF (1.0 M, 5.51 mL) was added dropwise over 25 min. The reaction was warmed to room temperature and quenched with MeOH:acetic acid (9:1, 5 mL). The mixture was concentrated under reduced pressure and carried onto the next transformation. LCMS (ESI): [M+H (-tBu)] 176. ¹H NMR (CDCl₃) δ: 3.77-3.99 (m, 2H), 3.68 (br d, J=8.5 Hz, 2H), 3.57 (br d, J=6.7 Hz, 2H), 2.64 (br s, 1H), 2.48 (br s, 1H), 1.69 (br s, 1H), 1.42-1.48 (m, 9H), 1.18 (d, J=6.7 Hz, 3H).

Intermediate 12

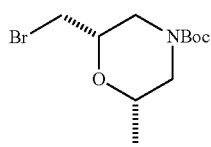 [SMILES: C[C@H]1CN(C(=O)OC(C)(C)C)C[C@@H](CBr)O1]

tert-butyl (cis)-2-(bromomethyl)-6-methylmorpholine-4-carboxylate: The title compound was prepared in an analogous manner to that of intermediate 7 from tert-butyl cis-2-(hydroxymethyl)-6-methylmorpholine-4-carboxylate. LCMS (ESI): [M]* 293. $^1$H NMR (CDCl$_3$) δ: 4.08 (dt, J=6.9, 3.6 Hz, 1H), 3.89-4.00 (m, 2H), 3.83 (dd, J=11.9, 4.0 Hz, 1H), 3.47-3.55 (m, 2H), 3.37-3.42 (m, 2H), 1.46-1.49 (m, 9H), 1.24 (d, J=6.7 Hz, 3H).

Example 1-34

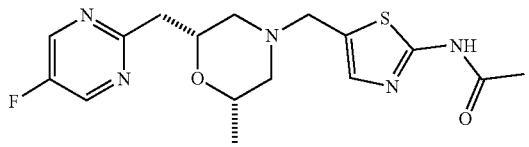 [SMILES: CC(=O)Nc1ncc(CN2C[C@@H](Cc3ncc(F)cn3)O[C@@H](C)C2)s1]

N-(5-(((cis)-2-((5-fluoropyrimidin-2-yl)methyl)-6-methylmorpholino)methyl)thiazol-2-yl)acetamide: The title compound was prepared in an analogous manner of that in scheme 1 from tert-butyl (cis)-2-(bromomethyl)-6-methylmorpholine-4-carboxylate, 2-bromo-5-fluoro-pyrimidine, and N-[5-(chloromethyl)thiazol-2-yl]acetamide. LCMS (ESI): [M+H] 366. $^1$HNMR: (500 MHz, CDCl$_3$) δ11.18 (br s, 1H), 8.53 (s, 2H), 7.32 (s, 1H), 7.20 (s, 1H), 4.11-4.18 (m, 1H), 3.60-3.70 (m, 3H), 3.19 (dd, J=14.3, 7.0 Hz, 1H), 3.03 (dd, J=14.0, 6.7 Hz, 1H), 2.85 (br d, J=10.4 Hz, 1H), 2.73 (br d, J=11.0 Hz, 1H), 2.29-2.31 (m, 3H), 1.98 (t, J=10.7 Hz, 1H), 1.80 (t, J=10.4 Hz, 1H), 1.25 (d, J=7.3 Hz, 1H), 1.08 (d, J=6.1 Hz, 3H).

Example 1-35

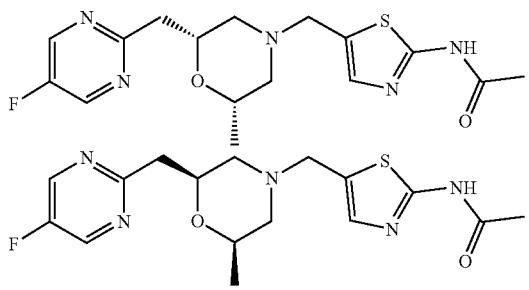

The mixture of enantiomers of Example 1-34, namely N-(5-(42R,6S)-2-((5-fluoropyrimidin-2-yl)methyl)-6-methylmorpholino)methyl)thiazol-2-yl)acetamide and N-(5-(((2S,6R)-2-((5-fluoropyrimidin-2-yl)methyl)-6-methylmorpholino)methyl)thiazol-2-yl)acetamide, was separated using the following conditions: Column: CHIRALPAK IC 30×250 mm, 5 um. Method: 40% MeOH with 0.1% diethyl amine in CO$_2$ (flow rate: 100 mL/min), ABPR 120 bar, MBPR 40 psi, as:

Peak 1: LCMS (ESI): [M+H] 366. $^1$H NMR: (500 MHz, METHANOL-d$_4$) δ8.65 (s, 2H), 7.23 (s, 1H), 4.14-4.19 (m, 1H), 3.69 (s, 2H), 3.58-3.66 (m, 1H), 3.04-3.13 (m, 1H), 2.95-3.04 (m, 1H), 2.87 (d, J=11.6 Hz, 1H), 2.69-2.81 (m, 3H), 2.07-2.25 (m, 3H), 1.93 (t, J=10.7 Hz, 1H), 1.79 (t, J=10.7 Hz, 1H), 1.18 (t, J=7.3 Hz, 3H), 1.05 (d, J=6.1 Hz, 3H)

Peak 2: LCMS (ESI): [M+H] 366. $^1$H NMR: (500 MHz, METHANOL-d$_4$) δ8.65 (s, 2H), 7.23 (s, 1H), 4.14-4.21 (m, 1H), 3.69 (s, 2H), 3.58-3.67 (m, 1H), 2.96-3.17 (m, 2H), 2.83-2.92 (m, 1H), 2.71-2.83 (m, 3H), 2.16-2.28 (m, 3H), 1.93 (t, J=10.7 Hz, 1H), 1.79 (t, J=10.7 Hz, 1H), 1.13-1.27 (m, 3H), 1.05 (d, J=6.1 Hz, 3H)

Intermediate 13

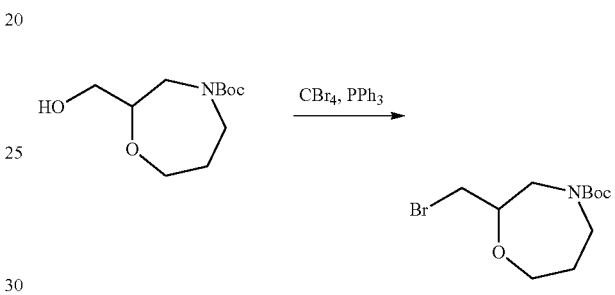

tert-butyl 2-(bromomethyl)-1,4-oxazepane-4-carboxylate: To solution of tert-butyl 2-(hydroxymethyl)-1,4-oxazepane-4-carboxylate (3.00 g, 12.9 mmol) in CH$_2$Cl$_2$ (65 mL) at 0° C. was added triphenylphosphine (polymer supported) (10.21 g, 38.9 mmol) followed by carbon tetrabromide (8.60 g, 25.9 mmol). The mixture was warmed to room temperature and stirred for 72 h. The mixture was filtered over celite and concentrated in vacuo. The residue was purified by silica gel chromatography (0-70% EtOAc:heptane) to afford the title compound (2.26 g, 59% yield). LCMS (ESI): [M-tBu)] 237. $^1$HNMR: (500 MHz, CDCl$_3$) δ4.04-4.18 (m, 1H), 3.91-4.04 (m, 1H), 3.64-3.81 (m, 2H), 3.45-3.58 (m, 1H), 3.20-3.43 (m, 3H), 2.98-3.12 (m, 1H), 1.85-1.98 (m, 2H), 1.46 (d, J=3.05 Hz, 9H)

Example 1-36

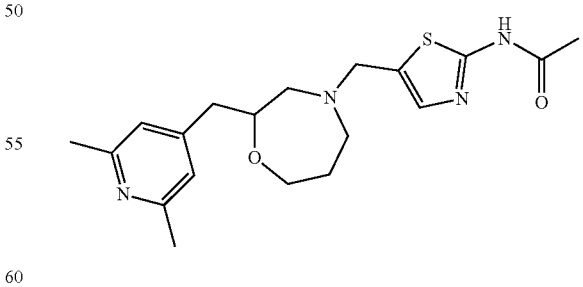

N-(5-((2-((2,6-dimethylpyridin-4-yl)methyl)-1,4-oxazepan-4-yl)methyl)thiazol-2-yl)acetamide: The title compound was prepared in an analogous manner of that in scheme 1 from tert-butyl 2-(bromomethyl)-1,4-oxazepane-4-carboxylate, 4-bromo-2,6-dimethylpyridine, and N-[5-(chloromethyl)thiazol-2-yl]acetamide. LCMS (ESI): [M+H] 375. $^1$HNMR: (500 MHz, CDCl$_3$) δ11.95 (br s, 1H), 7.17 (s, 1H), 6.78 (s, 2H), 3.81-3.90 (m, 2H), 3.79 (d, J=3.66 Hz, 2H), 3.66-3.74 (m, 1H), 2.83-2.90 (m, 2H), 2.69 (dd, J=7.94, 14.04 Hz, 1H), 2.63 (ddd, J=4.27, 8.55, 12.82 Hz, 1H), 2.52 (dd, J=5.80, 13.73 Hz, 1H), 2.47 (s, 6H), 2.43 (dd, J=9.16, 13.43 Hz, 1H), 2.31 (s, 3H), 1.89-1.97 (m, 1H), 1.83-1.89 (m, 1H).

Example 1-37

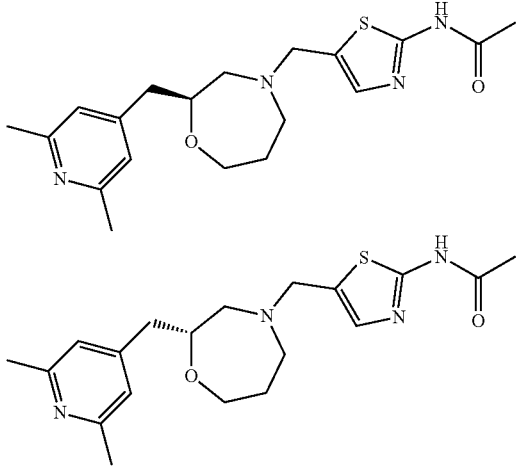

The mixture of enantiomers of Example 1-36, namely (S)—N-(5-((2-(2,6-dimethylpyridin-4-yl)methyl)-1,4-oxazepan-4-yl)methyl)thiazol-2-yl)acetamide and (R)—N-(5-((2-(2,6-dimethylpyridin-4-yl)methyl)-1,4-oxazepan-4-yl)methyl)thiazol-2-yl)acetamide, was separated using the following conditions: Column: CHIRALPAK AD-H 30×250 mm, 5 um. Method: 30% IPA w/0.1% diethyl amine in CO$_2$ (flow rate: 100 mL/min, ABPR 120 bar, MBPR 60 psi, as Peak 1 and Peak 2.

Example 1-38

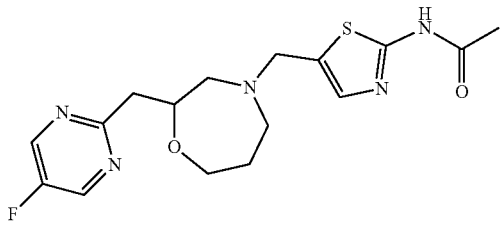 [SMILES: CC(=O)Nc1ncc(CN2CCCOC(Cc3ncc(F)cn3)C2)s1]

N-(5-((2-((5-fluoropyrimidin-2-yl)methyl)-1,4-oxazepan-4-yl)methyl)thiazol-2-yl)acetamide: The title compound was prepared in an analogous manner of that in scheme 1 from tert-butyl 2-(bromomethyl)-1,4-oxazepane-4-carboxylate, 2-bromo-5-fluoro-pyrimidine and N-[5-(chloromethyl)thiazol-2-yl]acetamide. LCMS (ESI): [M+H] 366. $^1$HNMR: (500 MHz, CDCl$_3$) δ11.67 (br s, 1H), 8.51 (s, 2H), 7.19 (s, 1H), 4.26 (q, J=7.33 Hz, 1H), 3.77-3.91 (m, 3H), 3.67-3.75 (m, 1H), 3.13 (dd, J=7.94, 14.04 Hz, 1H), 2.87-3.02 (m, 3H), 2.62-2.70 (m, 1H), 2.55 (dd, J=8.85, 13.12 Hz, 1H), 2.32 (s, 3H), 1.90-2.01 (m, 1H), 1.80-1.88 (m, 1H).

Example 1-39

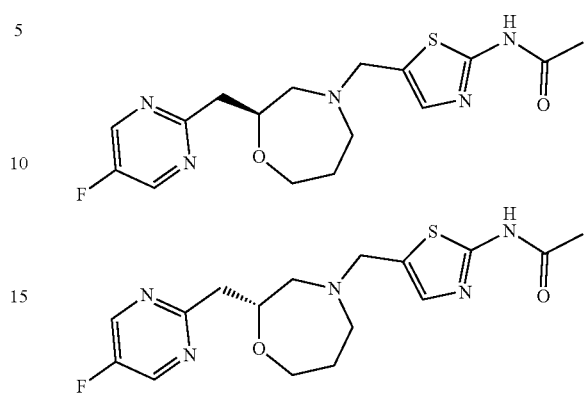

The mixture of enantiomers of Example 1-38, namely (S)—N-(5-((2-(5-fluoropyrimidin-2-yl)methyl)-1,4-oxazepan-4-yl)methyl)thiazol-2-yl)acetamide and (R)—N-(5-((2-((5-fluoropyrimidin-2-yl)methyl)-1,4-oxazepan-4-yl)methyl)thiazol-2-yl)acetamide, was separated using the following conditions: Column: CHIRALPAK IC 30×250 mm, 5 um. Method: 40% EtOH with 0.1% diethyl amine in CO$_2$ (flow rate: 100 mL/min), ABPR 120 bar, MBPR 40 psi, as Peak 1 and Peak 2.

Example 1-40

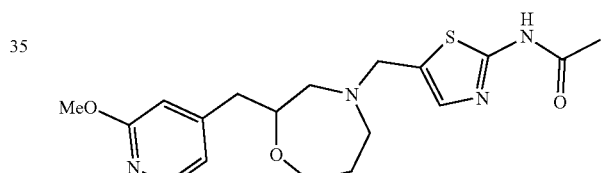

N-(5-((2-((2-methoxypyridin-4-yl)methyl)-1,4-oxazepan-4-yl)methyl)thiazol-2-yl)acetamide: The title compound was prepared in an analogous manner of that in scheme 1 from tert-butyl 2-(bromomethyl)-1,4-oxazepane-4-carboxylate, 4-bromo-2-methoxypyridine, and N-[5-(chloromethyl)thiazol-2-yl]acetamide. LCMS (ESI): [M+H] 377. $^1$HNMR: (500 MHz, CDCl$_3$) δ12.10 (br s, 1H), 8.03 (d, J=4.88 Hz, 1H), 7.17 (s, 1H), 6.72 (dd, J=1.22, 5.49 Hz, 1H), 6.56 (s, 1H), 3.90 (s, 3H), 3.83-3.88 (m, 2H), 3.80 (s, 2H), 3.65-3.73 (m, 1H), 2.80-2.91 (m, 2H), 2.72 (dd, J=7.94, 14.04 Hz, 1H), 2.60-2.67 (m, 1H), 2.56 (dd, J=5.49, 14.04 Hz, 1H), 2.45 (dd, J=8.85, 13.12 Hz, 1H), 2.32 (s, 3H), 1.80-1.96 (m, 2H).

Example 1-41

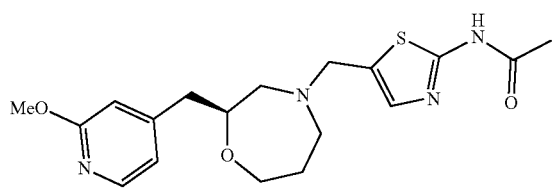

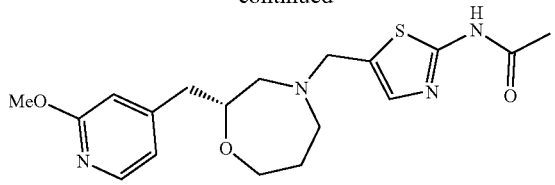

The mixture of enantiomers of Example 1-40, namely (S)—N-(5-((2-(2-methoxypyridin-4-yl)methyl)-1,4-oxazepan-4-yl)methyl)thiazol-2-yl)acetamide and (R)—N-(5-((2-(2-methoxypyridin-4-yl)methyl)-1,4-oxazepan-4-yl)methyl)thiazol-2-yl)acetamide, was separated using the following conditions: Column: CHIRALPAK AD-H 30×250 mm, 5 um. Method: 35% IPA with 0.1% diethyl amine in $CO_2$ (flow rate: 100 mL/min), ABPR 120 bar, MBPR 60 psi, as Peak 1 and Peak 2.

Intermediate 14

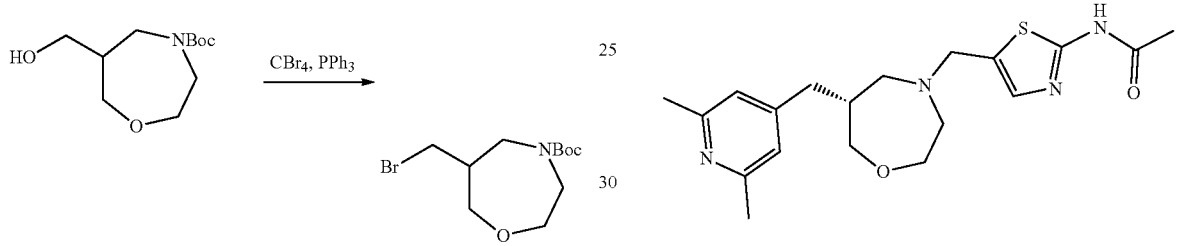

tert-butyl 6-(bromomethyl)-1,4-oxazepane-4-carboxylate: To solution of tert-butyl 6-(hydroxymethyl)-1,4-oxazepane-4-carboxylate (3.18 g, 13.7 mmol) in $CH_2Cl_2$ (65 mL) at 0° C. was added triphenylphosphine (polymer supported) (10.82 g, 41.2 mmol) followed by carbon tetrabromide (9.12 g, 27.5 mmol). The mixture was warmed to room temperature and stirred for 72 h. The mixture was filtered over celite and concentrated in vacuo. The residue was purified by silica gel chromatography (0-20% EtOAc:heptane) to afford the title compound (2.71 g, 67% yield). $^1$HNMR: (500 MHz, $CDCl_3$) δ3.56-3.79 (m, 6H), 3.31-3.45 (m, 4H), 2.35-2.47 (m, 1H), 1.61 (d, J=4.3 Hz, 1H), 1.48 ppm (br d, J=10.4 Hz, 9H).

Example 1-42

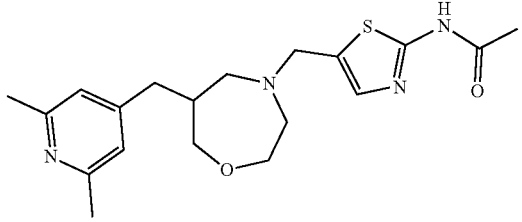

N-(5-((6-((2,6-dimethylpyridin-4-yl)methyl)-1,4-oxazepan-4-yl)methyl)thiazol-2-yl)acetamide: The title compound was prepared in an analogous manner of that in scheme 1 from tert-butyl 6-(bromomethyl)-1,4-oxazepane-4-carboxylate, 4-bromo-2-methoxypyridine, and N-[5-(chloromethyl)thiazol-2-yl]acetamide. LCMS (ESI): [M+H] 375. $^1$HNMR: (500 MHz, METHANOL-$d_4$) δ7.16 (s, 1H), 6.79 (s, 2H), 3.86-3.94 (m, 1H), 3.68-3.82 (m, 5H), 3.42-3.51 (m, 1H), 2.76-2.91 (m, 1H), 2.69 (dq, J=12.9, 3.6 Hz, 2H), 2.45-2.56 (m, 1H), 2.42 (s, 6H), 2.27-2.39 (m, 3H), 2.24 (s, 3H).

Example 1-43

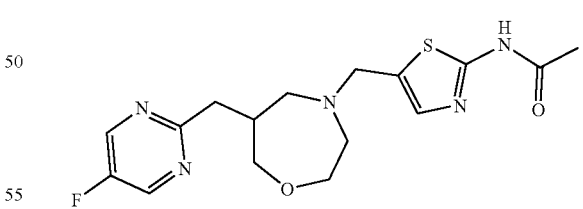

The mixture of enantiomers of Example 1-42, namely (S)—N-(5-((6-((2,6-dimethylpyridin-4-yl)methyl)-1,4-oxazepan-4-yl)methyl)thiazol-2-yl)acetamide and (R)—N-(5-((6-((2,6-dimethylpyridin-4-yl)methyl)-1,4-oxazepan-4-yl)methyl)thiazol-2-yl)acetamide, was separated using the following conditions: Column: CHIRALPAK AD-H 30×250 mm, 5 um. Method: 40% IPA with 0.1% diethyl amine in $CO_2$ (flow rate: 100 mL/min), ABPR 120 bar, MBPR 40 psi, as Peak 1 and Peak 2.

Example 1-44

N-(5-((6-((5-fluoropyrimidin-2-yl)methyl)-1,4-oxazepan-4-yl)methyl)thiazol-2-yl)acetamide: The title compound was prepared in an analogous manner of that in scheme 1 from tert-butyl 6-(bromomethyl)-1,4-oxazepane-4-carboxylate, 2-bromo-5-fluoro-pyrimidine and N-[5-(chloromethyl)thiazol-2-yl]acetamide. LCMS (ESI): [M+H] 366. $^1$HNMR: (500 MHz, METHANOL-$d_4$) δ8.53 (s, 2H), 7.15 (s, 1H), 3.97 (dd, J=11.9, 5.8 Hz, 1H), 3.67-3.84 (m, 5H), 3.49-3.58 (m, 1H), 2.79-2.87 (m, 2H), 2.60-2.77 (m, 5H), 2.46 (dd, J=13.1, 7.6 Hz, 1H), 2.20-2.28 (m, 4H).

Example 1-45

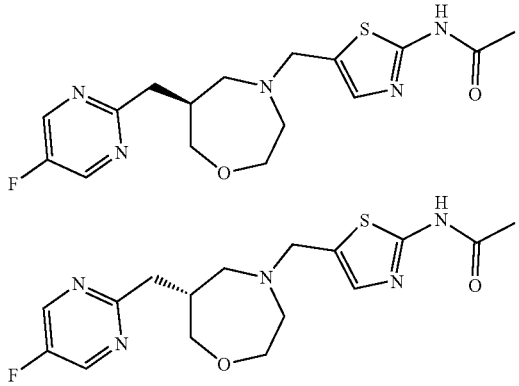

The mixture of enantiomers of Example 1-44, namely (S)—N-(5-((6-((5-fluoropyrimidin-2-yl)methyl)-1,4-oxazepan-4-yl)methyl)thiazol-2-yl)acetamide and (R)—N-(5-((6-((5-fluoropyrimidin-2-yl)methyl)-1,4-oxazepan-4-yl)methyl)thiazol-2-yl)acetamide, was separated using the following conditions: Column: CHIRALPAK AD-H 30×250 mm, 5 um. Method: 40% IPA with 0.1% diethyl amine in $CO_2$ (flow rate: 100 mL/min), ABPR 120 bar, MBPR 60 psi, as Peak 1 and Peak 2.

Example 1-46

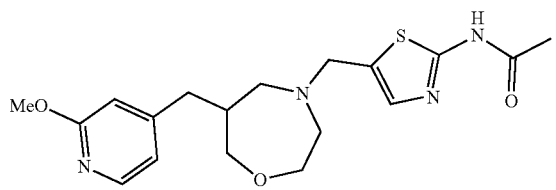

N-(5-((6-((2-methoxypyridin-4-yl)methyl)-1,4-oxazepan-4-yl)methyl)thiazol-2-yl)acetamide: The title compound was prepared in an analogous manner of that in scheme 1 from from tert-butyl 6-(bromomethyl)-1,4-oxazepane-4-carboxylate, 4-bromo-2-methoxypyridine, and N-[5-(chloromethyl)thiazol-2-yl]acetamide. LCMS (ESI): [M+H] 377. $^1$HNMR: (500 MHz, METHANOL-$d_4$) δ7.93 (d, J=4.9 Hz, 1H), 7.17 (s, 1H), 6.71 (dd, J=5.5, 1.2 Hz, 1H), 6.54 (s, 1H), 3.88-3.93 (m, 1H), 3.86-3.88 (m, 3H), 3.70-3.81 (m, 4H), 3.49 (dd, J=12.2, 7.9 Hz, 1H), 2.78-2.84 (m, 1H), 2.67-2.75 (m, 2H), 2.49-2.56 (m, 1H), 2.40-2.47 (m, 2H), 2.28-2.35 (m, 1H), 2.24 (s, 3H).

Example 1-47

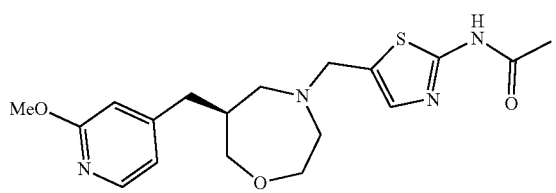

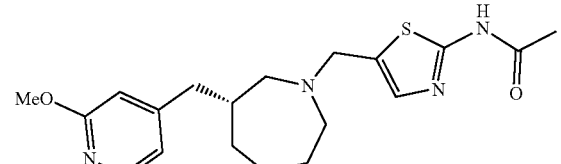

The mixture of enantiomers of Example 1-46, namely (S)—N-(5-((6-((2-methoxypyridin-4-yl)methyl)-1,4-oxazepan-4-yl)methyl)thiazol-2-yl)acetamide and (R)—N-(5-((6-((2-methoxypyridin-4-yl)methyl)-1,4-oxazepan-4-yl)methyl)thiazol-2-yl)acetamide, was separated using the following conditions: Column: CHIRALPAK IC 30×250 mm, 5 um. Method: 40% IPA with 0.1% diethyl amine in $CO_2$ (flow rate: 100 mL/min), ABPR 120 bar, MBPR 40 psi, as Peak 1 and Peak 2.

Scheme 2

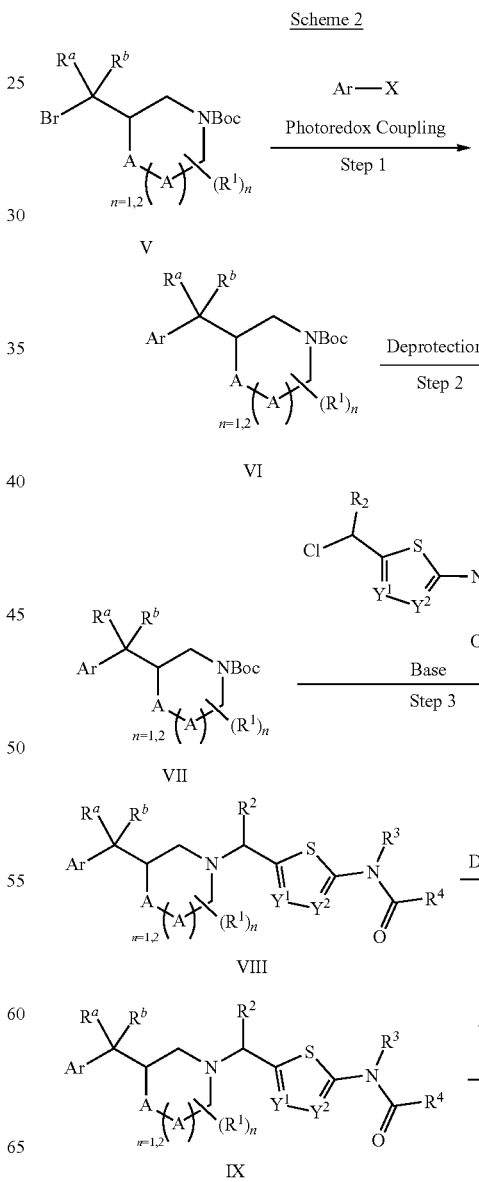

-continued

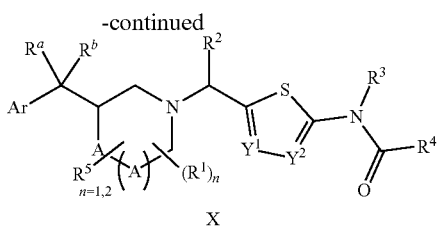

A = NPg, CH$_2$, CHR$^1$
independently substituted

Intermediate 15

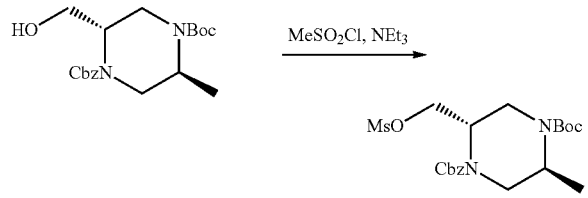

1-benzyl 4-(tert-butyl) (2S,5S)-5-methyl-2-(((methylsulfonyl)oxy)methyl)-piperazine-1,4-dicarboxylate: Methanesulfonyl chloride (6.0 g, 53 mmol, 4.1 mL) was added dropwise to a solution of 1-benzyl 4-(tert-butyl) (2S,5S)-2-(hydroxymethyl)-5-methylpiperazine-1,4-dicarboxylate (16 g, 43.9 mmol) and triethylamine (9.1 g, 90 mmol, 12.5 mL) in ether (200 mL) at 0° C. The reaction was then stirred at room temperature for 2 h. The reaction solution was washed with water, brine, and then dried under MgSO$_4$, and filtered. The filtrate was concentrated under vacuum to provide the title compound which was used in the next step without further purifications. LCMS (ESI): [M+Na] 465 (M+Na).

Intermediate 16

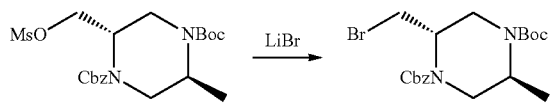 [SMILES: C[C@H]1CN(C(=O)OCc2ccccc2)[C@H](COS(C)(=O)=O)CN1C(=O)OC(C)(C)C ; "LiBr" ; C[C@H]1CN(C(=O)OCc2ccccc2)[C@H](CBr)CN1C(=O)OC(C)(C)C]

1-benzyl 4-(tert-butyl) (2S,5S)-2-(bromomethyl)-5-methylpiperazine-1,4-dicarboxylate: To a solution of 1-benzyl 4-(tert-butyl) (2S,5S)-5-methyl-2-(((methylsulfonyl)oxy)methyl)-piperazine-1,4-dicarboxylate (19 g, 42.9 mmol) in THF (200 mL) was added LiBr (29.8 g, 343.4 mmol). The reaction was heated at reflux for 3 h. After 3 h, another 5 g of LiBr was added. The mixture was heated at reflux for 1 h, and then another 5 g was added. The reaction was kept at reflux for one more hour. The mixture was cooled to room temperature, the solid was filtered off, the filtrate was concentrated in cauo, and purified by chromatography on silica gel (0-100% EtOAc:heptane) to provide the title compound (12.5 g, 68% yield). LCMS (ESI): [M+H] not observed, observe 327 & 329 (M-Boc). $^1$H NMR (400 MHz, CDCl$_3$) δ7.29-7.43 (m, 5H), 5.09-5.26 (m, 2H), 3.99-4.62 (m, 3H), 3.69-3.92 (m, 1H), 3.33-3.58 (m, 2H), 3.10-3.30 (m, 2H), 1.48 (s, 9H), 1.07-1.21 (m, 3H).

Intermediate 17

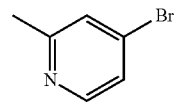

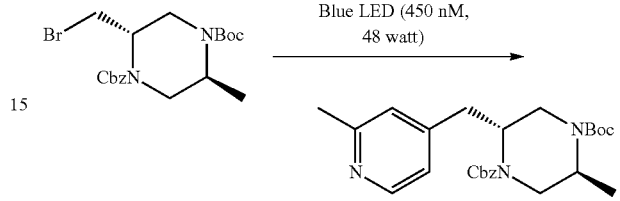

1-benzyl 4-(tert-butyl) (2R,5S)-5-methyl-2-((2-methylpyridin-4-yl)methyl)piperazine-1,4-dicarboxylate: A mixture of NiCl$_2$ glyme (17.9 mg, 81.4 umol), Ir[dF(CF$_3$)ppy]$_2$(dtbbpy)PF$_6$ (18 mg, 16.3 umol) and BBBPY (21.8 mg, 81.4 umol) in DME (20 ml) was purged with nitrogen for 10 minutes. In another vial, a mixture of 4-bromo-2-methylpyridine (280 mg, 1.6 mmol), 1-benzyl 4-(tert-butyl) (2S,5S)-2-(bromomethyl)-5-methylpiperazine-1,4-dicarboxylate (696 mg, 1.6 mmol), lithium hydroxide (156 mg, 6.5 mmol) and bis(trimethylsilyl)silyl-trimethyl-silane (810 mg, 3.3 mmol, 1.0 mL) in DME (6 ml) was purged with nitrogen for 10 min. The first solution was added to the second solution under nitrogen. The reaction mixture was then irradiated with 2× blue Kessel Lamp (blue light) at 40° C. overnight. The reaction mixture was treated with charcoal, filtered and concentrated in vacuo. The residue was purified by chromatography on silica gel (10-100% EtOAc:heptane) to provide the title compound (323 mg, 45% yield). LCMS (ESI): [M+H] 440. $^1$H NMR (400 MHz, CDCl$_3$) δ8.21-8.61 (m, 1H), 7.34-7.48 (m, 3H), 7.29 (br d, J=2.51 Hz, 2H), 7.16-7.26 (m, 1H), 6.84-7.13 (m, 1H), 4.86-5.19 (m, 2H), 4.17-4.61 (m, 2H), 3.56-4.00 (m, 2H), 3.27 (br d, J=12.80 Hz, 1H), 3.06-3.21 (m, 1H), 2.82-3.00 (m, 2H), 2.65-2.81 (m, 2H), 2.52-2.63 (m, 1H), 2.01 (s, 3H), 1.49 (br d, J=13.30 Hz, 9H), 1.17 (br dd, J=6.78, 19.32 Hz, 3H).

Intermediate 18

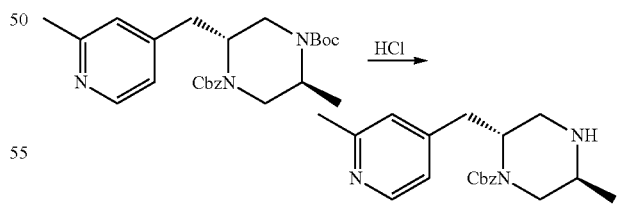

Benzyl (2R,5S)-5-methyl-2-((2-methylpyridin-4-yl)methyl)piperazine-1-carboxylate: To a solution of 1-benzyl 4-(tert-butyl) (2R,5S)-5-methyl-2-((2-methylpyridin-4-yl)methyl)piperazine-1,4-dicarboxylate (320 mg, 0.728 mmol) in CH$_2$Cl$_2$ (5.0 mL) was added a solution of HCl in dioxane (4 M, 0.910 mL). The mixture was stirred at room temperature for 2 h. The mixture was concentrated in vacuo and used in the next step without purification. LCMS (ESI): [M+H] 340.

Intermediate 19

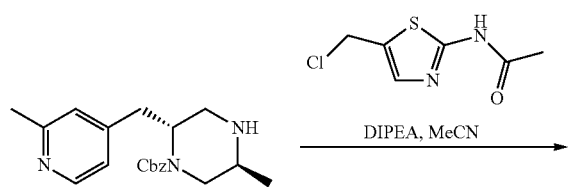

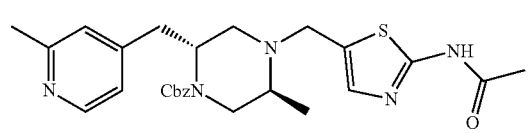

Benzyl (2R,5S)-4-((2-acetamidothiazol-5-yl)methyl)-5-methyl-2-((2-methylpyridin-4-yl)methyl)piperazine-1-carboxylate: To a mixture of benzyl (2R,5S)-5-methyl-2-[(2-methyl-4-pyridyl)methyl]piperazine-1-carboxylate (270 mg, 0.718 mmol, hydrochloride) and N-[5-(chloromethyl)thiazol-2-yl]acetamide (164 mg, 0.862 mmol) in acetonitrile (5.0 mL) was added diisopropylethylamine (0.557 g, 4.3 mmol, 0.753 mL). The reaction was stirred at room temperature for 1 h and concentrated in vacuo. Residue was purified by chromatography on silica gel (0-80% EtOAc-EtOH (3:1 v/v 2% NH$_4$OH):heptane) to provide the title compound (316 mg, 89% yield). LCMS (ESI): [M+H] 494; $^1$H NMR (400 MHz, METHANOL-d$_4$) δ8.12 (br s, 1H), 7.28-7.39 (m, 3H), 7.16-7.27 (m, 3H), 6.97 (br s, 1H), 5.00 (br s, 2H), 4.35 (br s, 1H), 3.75-3.89 (m, 2H), 3.65 (d, J=14.05 Hz, 1H), 3.49 (dd, J=3.39, 13.18 Hz, 1H), 3.18 (br s, 1H), 3.01 (br s, 2H), 2.66 (br dd, J=3.64, 11.92 Hz, 1H), 2.36 (br s, 4H), 2.21 (s, 3H), 1.00 (d, J=6.53 Hz, 3H).

Example 1-48

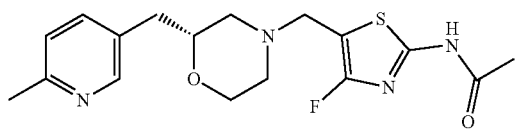

(R)—N-(4-fluoro-5-((2-((6-methylpyridin-3-yl)methyl)morpholino)methyl)thiazol-2-yl)acetamide: The title compound was prepared in an analogous manner of that in scheme 1 and intermediate 26 from tert-butyl (S)-2-(bromomethyl)morpholine-4-carboxylate, 5-bromo-2-methylpyridine, and N-(4-fluoro-5-formylthiazol-2-yl)acetamide (prepared according to the literature procedure described in WO2018/140299A1). LCMS (ESI): [M+H] 364. $^1$HNMR: (500 MHz, CDCl$_3$) δ8.62 (d, J=2.44 Hz, 1H) 8.41 (dd, J=8.24, 2.14 Hz, 1H) 7.89 (d, J=8.55 Hz, 1H) 4.51 (s, 2H) 4.12 (dd, J=13.43, 3.05 Hz, 1H) 3.97-4.06 (m, 2H) 3.70-3.79 (m, 1H) 3.62-3.69 (m, 1H) 3.50 (br d, J=12.21 Hz, 1H) 3.10-3.21 (m, 2H) 2.97-3.08 (m, 3H) 2.79 (s, 3H) 2.23-2.25 (m, 3H).

Example 1-49

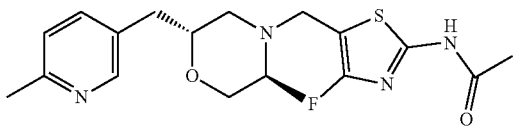

N-(4-fluoro-5-(((2R,5S)-5-methyl-2-((6-methylpyridin-3-yl)methyl)morpholino)methyl)thiazol-2-yl)acetamide: The title compound was prepared in an analogous manner of that in scheme 1 and intermediate 26 from tert-butyl (2S,5S)-2-(bromomethyl)-5-methylmorpholine-4-carboxylate, 5-bromo-2-methylpyridine, and N-(4-fluoro-5-formylthiazol-2-yl)acetamide (prepared according to the literature procedure described in WO2018/140299A1). LCMS (ESI): [M+H] 378.1. $^1$HNMR: (500 MHz, CDCl$_3$) δ11.67 (br s, 1H) 8.33 (s, 1H) 7.46 (dd, J=7.94, 1.83 Hz, 1H) 7.08 (d, J=7.94 Hz, 1H) 3.56-3.75 (m, 5H) 2.75-2.88 (m, 2H) 2.70 (dd, J=14.34, 5.19 Hz, 1H) 2.57 (s, 1H) 2.52 (s, 3H) 2.41-2.49 (m, 2H) 2.30 (s, 3H) 1.07 (d, J=6.71 Hz, 3H)

Example 2-1

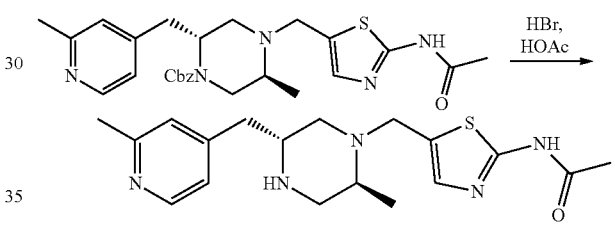

N-(5-(((2S,5R)-2-methyl-5-((2-methylpyridin-4-yl)methyl)piperazin-1-yl)methyl)thiazol-2-yl)acetamide: A mixture of benzyl (2R,5S)-4-[(2-acetamidothiazol-5-yl)methyl]-5-methyl-2-[(2-methyl-4-pyridyl)methyl]piperazine-1-carboxylate (300 mg, 0.607 mmol) and HBr (33% in HOAc, 1.0 mL) was stirred at room temperature for 4 h. The mixture was diluted with ether and the resulting precipitate was filtered and washed with ether, then dried under vacuum to provide the title compound (282 mg, 105% yield, HBr salt). LCMS (ESI): [M+H]360. $^1$H NMR (400 MHz, METHANOL-d$_4$) δ8.69 (d, J=6.27 Hz, 1H), 8.03 (s, 1H), 7.96 (d, J=6.02 Hz, 1H), 7.79 (s, 1H), 4.84 (br s, 1H), 4.60 (d, J=14.81 Hz, 1H), 4.38 (br d, J=8.53 Hz, 1H), 3.65-3.88 (m, 3H), 3.37-3.53 (m, 4H), 2.82 (s, 3H), 2.28 (s, 3H), 1.59 (d, J=6.27 Hz, 3H).

Example 2-2

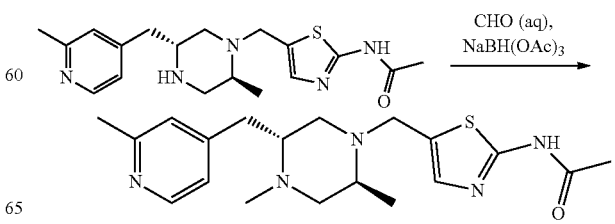

N-(5-(((2S,5R)-2,4-dimethyl-5-((2-methylpyridin-4-yl)methyl)piperazin-1-yl)methyl)thiazol-2-yl)acetamide: To a mixture of N-[5-[[(2S,5R)-2-methyl-5-[(2-methyl-4-pyridyl)methyl]piperazin-1-yl]methyl]thiazol-2-yl]acetamide (50 mg, 0.114 mmol, hydrobromide), sodium triacetoxyborohydride (48 mg, 0.227 mmol) and formaldehyde (37% in water, 1.00 mL) was added triethylamine (23 mg, 0.227 mmol, 31 uL). The reaction solution was then heated at 80° C. in microwave for 20 minutes. The mixture was concentrated in vacuo and purified by HPLC to provide the title compound (24 mg, 43% yield, TFA salt). (ESI): [M+H] 374. $^1$H NMR (400 MHz, METHANOL-$d_4$) δ8.61 (d, J=6.27 Hz, 1H), 7.81 (s, 1H), 7.77 (br d, J=6.02 Hz, 1H), 7.23-7.30 (m, 1H), 4.13-4.27 (m, 1H), 3.85 (d, J=14.81 Hz, 1H), 3.60 (br d, J=11.29 Hz, 2H), 3.47 (d, J=10.04 Hz, 1H), 3.00-3.23 (m, 2H), 2.84-2.99 (m, 5H), 2.75 (s, 3H), 2.40-2.53 (m, 1H), 2.21 (s, 3H), 1.26-1.35 (m, 3H).

Example 2-3

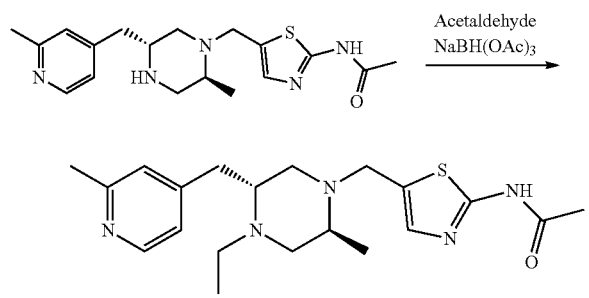

N-(5-(((2S,5R)-4-ethyl-2-methyl-5-((2-methylpyridin-4-yl)methyl)piperazin-1-yl)methyl)thiazol-2-yl)acetamide: To a mixture of N-[5-[[(2S,5R)-2-methyl-5-[(2-methyl-4-pyridyl)methyl]piperazin-1-yl]methyl]thiazol-2-yl]acetamide (50 mg, 0.114 mmol, hydrobromide), sodium triacetoxyborohydride (48 mg, 0.227 mmol), acetaldehyde (0.3 mL) and water (0.6 mL) was added triethylamine (57 mg, 0.568 mmol, 79 uL). The reaction solution was then heated at 80° C. in microwave for 20 minutes. The mixture was concentrated in vacuo and purified by HPLC to provide the title product (19 mg, 33% yield, TFA salt). LCMS (ESI): [M+H] 388. $^1$H NMR (400 MHz, METHANOL-$d_4$) δ8.62 (d, J=6.27 Hz, 1H), 7.84 (s, 1H), 7.79 (d, J=6.27 Hz, 1H), 7.26 (s, 1H), 4.18 (br d, J=14.81 Hz, 1H), 3.85 (d, J=14.56 Hz, 1H), 3.72-3.81 (m, 1H), 3.65 (br dd, J=4.27, 14.05 Hz, 1H), 3.45-3.60 (m, 2H), 3.06-3.26 (m, 2H), 2.95 (br d, J=9.54 Hz, 2H), 2.89 (dd, J=3.01, 13.30 Hz, 1H), 2.75 (s, 3H), 2.54 (dd, J=10.54, 13.30 Hz, 1H), 2.22 (s, 3H), 1.37 (t, J=7.28 Hz, 3H), 1.33 (d, J=5.52 Hz, 3H).

Example 2-4

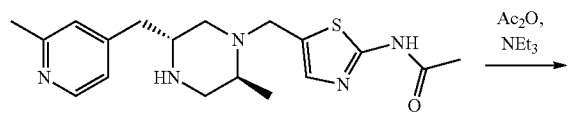

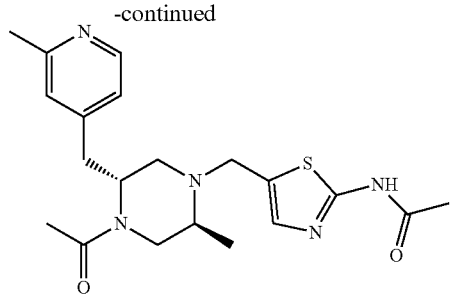

N-(5-(((2S,5R)-4-acetyl-2-methyl-5-((2-methylpyridin-4-yl)methyl)piperazin-1-yl)methyl)thiazol-2-yl)acetamide: To a solution of N-[5-[[(2S,5R)-2-methyl-5-[(2-methyl-4-pyridyl)methyl]piperazin-1-yl]methyl]thiazol-2-yl]acetamide (50 mg, 0.114 mmol, hydrobromide) in CH$_2$Cl$_2$ (1.0 mL) was added acetic anhydride (116 mg, 1.1 mmol, 107 uL), and triethylamine (57 mg, 0.567 mmol, 79 uL). The reaction was stirred at room temperature for 2 h. The reaction mixture was concentrated in vacuo and purified by HPLC to provide the title compound (34 mg, 58% yield, TFA salt). LCMS (ESI): [M+H] 402. $^1$H NMR (400 MHz, METHANOL-$d_4$) δ8.53 (br d, J=5.77 Hz, 1H), 7.72-7.82 (m, 2H), 7.54 (s, 1H), 5.12 (br s, 1H), 4.24-4.48 (m, 2H), 3.82-4.06 (m, 2H), 3.69 (br d, J=6.78 Hz, 1H), 3.37-3.58 (m, 1H), 3.25 (br s, 1H), 3.08 (br d, J=12.55 Hz, 1H), 2.72 (s, 3H), 2.23 (s, 3H), 1.99 (br s, 3H), 1.81-1.96 (m, 1H), 1.19-1.43 (m, 3H).

Example 2-5

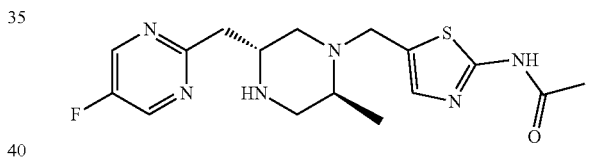

N-(5-4(2S,5R)-5-((5-fluoropyrimidin-2-yl)methyl)-2-methylpiperazin-1-yl)methyl)thiazol-2-yl)acetamide: The title compound was prepared in an analogous manner of that in scheme 2 from 2-bromo-5-fluoropyrimidine, 1-benzyl 4-(tert-butyl) (2S,5S)-2-(bromomethyl)-5-methylpiperazine-1,4-dicarboxylate and N-(5-(chloromethyl)thiazol-2-yl)acetamide. LCMS (ESI): [M+H] 365. $^1$H NMR (400 MHz, METHANOL-$d_4$) δ8.74 (s, 2H), 7.81 (s, 1H), 4.96 (d, J=14.81 Hz, 1H), 4.69 (d, J=14.56 Hz, 1H), 4.34-4.46 (m, 1H), 3.76-3.93 (m, 3H), 3.41-3.60 (m, 4H), 2.28 (s, 3H), 1.67 (d, J=6.27 Hz, 3H).

Example 2-6

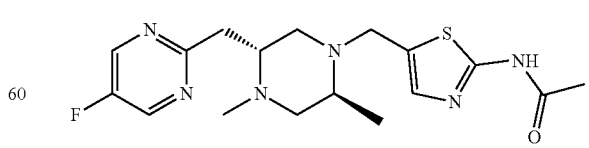

N-(5-((((2S,5R)-5-((5-fluoropyrimidin-2-yl)methyl)-2,4-dimethylpiperazin-1-yl)methyl)thiazol-2-yl)acetamide: The title compound was prepared in an analogous manner of that in example 2-2 from N-(5-(((2S,5R)-5-((5-fluoropyrimidin- 2-yl)methyl)-2-methylpiperazin-1-yl)methyl)thiazol-2-yl) acetamide. LCMS (ESI): [M+H] 379. ¹H NMR (400 MHz, METHANOL-d₄) δ8.68 (d, J=0.75 Hz, 2H), 7.25 (s, 1H), 4.21 (d, J=14.56 Hz, 1H), 3.71-3.91 (m, 2H), 3.35-3.52 (m, 3H), 3.02-3.12 (m, 2H), 2.98 (s, 3H), 2.82 (br s, 1H), 2.46 (dd, J=11.29, 13.30 Hz, 1H), 2.21 (s, 3H), 1.30 (d, J=6.27 Hz, 3H).

Example 2-7

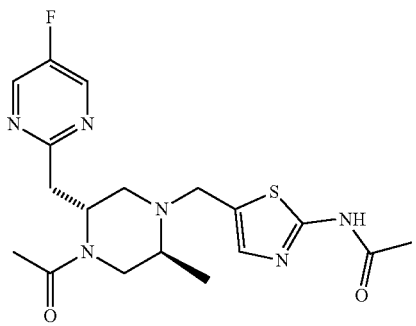

N-(5-(((2S,5R)-4-acetyl-5-((5-fluoropyrimidin-2-yl) methyl)-2-methylpiperazin-1-yl)methyl)thiazol-2-yl)acetamide: The title compound was prepared in an analogous manner of that in example 2-4 from N-(5-(((2S,5R)-5-((5-fluoropyrimidin-2-yl)methyl)-2-methylpiperazin-1-yl) methyl)thiazol-2-yl)acetamide. LCMS (ESI): [M+H] 407. ¹H NMR (400 MHz, METHANOL-d₄) δ8.61 (br s, 2H), 7.61 (s, 1H), 5.06-5.44 (m, 1H), 4.57 (s, 2H), 3.93 (br s, 1H), 3.79 (br d, J=6.78 Hz, 1H), 3.33-3.63 (m, 5H), 2.24 (s, 3H), 2.01-2.14 (m, 3H), 1.32-1.54 (m, 3H).

Example 2-8

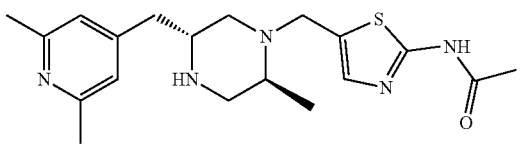 [SMILES: CC(=O)Nc1ncc(CN2C[C@@H](Cc3cc(C)nc(C)c3)NC[C@@H]2C)s1]

N-(5-(((2S,5R)-5-((2,6-dimethylpyridin-4-yl)methyl)-2-methylpiperazin-1-yl)methyl)thiazol-2-yl)acetamide: The title compound was prepared in an analogous manner of that in scheme 2 from 4-bromo-2,6-dimethylpyridine, 1-benzyl 4-(tert-butyl) (2S,5S)-2-(bromomethyl)-5-methylpiperazine-1,4-dicarboxylate and N-(5-(chloromethyl)thiazol-2-yl)acetamide. LCMS (ESI): [M+H] 373. ¹H NMR (400 MHz, METHANOL-d₄) δ7.84 (s, 1H), 7.78 (s, 2H), 4.92-4.97 (m, 1H), 4.68 (d, J=14.81 Hz, 1H), 4.33-4.45 (m, 1H), 3.82-3.93 (m, 1H), 3.71-3.81 (m, 2H), 3.44-3.54 (m, 2H), 3.39 (d, J=7.03 Hz, 2H), 2.77 (s, 6H), 2.29 (s, 3H), 1.62 (d, J=6.53 Hz, 3H).

Example 2-9

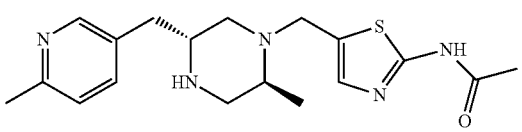 [SMILES: CC(=O)Nc1ncc(CN2C[C@@H](Cc3ccc(C)nc3)NC[C@@H]2C)s1]

N-(5-(((2S,5R)-2-methyl-5-((6-methylpyridin-3-yl)methyl)piperazin-1-yl)methyl)thiazol-2-yl)acetamide: The title compound was prepared in an analogous manner of that in scheme 2 from 5-bromo-2-methylpyridine, 1-benzyl 4-(tert-butyl) (2S,5S)-2-(bromomethyl)-5-methylpiperazine-1,4-dicarboxylate and N-(5-(chloromethyl)thiazol-2-yl)acetamide. LCMS (ESI): [M+H] 360. ¹H NMR (400 MHz, METHANOL-d₄) δ8.86 (d, J=1.76 Hz, 1H), 8.57 (dd, J=2.01, 8.28 Hz, 1H), 7.96 (d, J=8.28 Hz, 1H), 7.84 (s, 1H), 4.91-4.96 (m, 1H), 4.67 (d, J=14.56 Hz, 1H), 4.30-4.43 (m, 1H), 3.70-3.95 (m, 3H), 3.43-3.57 (m, 2H), 3.41 (d, J=7.53 Hz, 2H), 2.81 (s, 3H), 2.29 (s, 3H), 1.62 (d, J=6.53 Hz, 3H).

Example 2-10

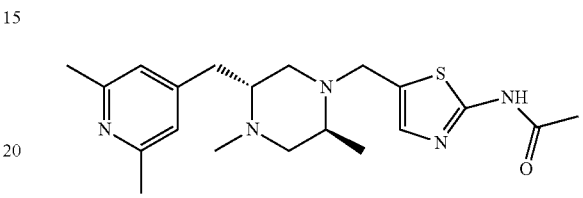

N-(5-4(2S,5R)-5-((2,6-dimethylpyridin-4-yl)methyl)-2,4-dimethylpiperazin-1-yl)methyl)thiazol-2-yl)acetamide: The title compound was prepared in an analogous manner of that in example 2-2 from N-(5-(((2S,5R)-5-((2,6-dimethylpyridin-4-yl)methyl)-2-methylpiperazin-1-yl)methyl)thiazol-2-yl)acetamide. LCMS (ESI): [M+H] 388. ¹H NMR (400 MHz, METHANOL-d₄) δ7.61 (s, 2H), 7.26 (s, 1H), 4.19 (br d, J=15.06 Hz, 1H), 3.83 (d, J=14.81 Hz, 1H), 3.43-3.66 (m, 3H), 2.83-3.04 (m, 7H), 2.70 (s, 6H), 2.39-2.53 (m, 1H), 2.21 (s, 3H), 1.30 (d, J=6.02 Hz, 3H).

Example 2-11

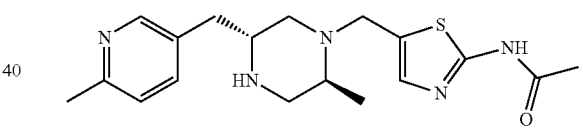

N-(5-(((2S,5R)-2,4-dimethyl-5-((6-methylpyridin-3-yl)methyl)piperazin-1-yl)methyl)thiazol-2-yl)acetamide: The title compound was prepared in an analogous manner of that in example 2-2 from N-(5-(((2S,5R)-2-methyl-5-((6-methylpyridin-3-yl)methyl)piperazin-1-yl)methyl)thiazol-2-yl) acetamide. LCMS (ESI): [M+H] 374. ¹H NMR (400 MHz, METHANOL-d₄) δ8.67 (d, J=2.01 Hz, 1H), 8.35 (dd, J=2.01, 8.53 Hz, 1H), 7.84 (d, J=8.53 Hz, 1H), 7.26 (s, 1H), 4.19 (d, J=14.56 Hz, 1H), 3.86 (d, J=14.81 Hz, 1H), 3.40-3.60 (m, 3H), 2.84-3.08 (m, 6H), 2.76 (s, 3H), 2.49 (dd, J=10.79, 13.05 Hz, 1H), 2.21 (s, 3H), 1.29 (d, J=5.77 Hz, 3H).

Example 2-12

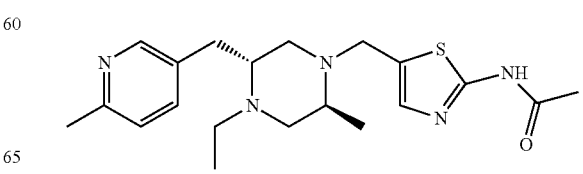

N-(5-(((2S,5R)-4-ethyl-2-methyl-5-((6-methylpyridin-3-yl)methyl)piperazin-1-yl)methyl)thiazol-2-yl)acetamide: The title compound was prepared in an analogous manner of that in example 2-3 from N-(5-(((2S,5R)-2-methyl-5-((6-methylpyridin-3-yl)methyl)piperazin-1-yl)methyl)thiazol-2-yl)acetamide. LCMS (ESI): [M+H] 388. $^1$H NMR (400 MHz, METHANOL-d$_4$) δ8.67 (d, J=1.76 Hz, 1H), 8.35 (dd, J=2.01, 8.28 Hz, 1H), 7.84 (d, J=8.53 Hz, 1H), 7.24 (s, 1H), 4.15 (br d, J=14.56 Hz, 1H), 3.84 (d, J=14.81 Hz, 1H), 3.45-3.73 (m, 4H), 3.21 (q, J=7.28 Hz, 2H), 2.97-3.09 (m, 1H), 2.85-2.96 (m, 2H), 2.76 (s, 3H), 2.49 (dd, J=10.42, 13.18 Hz, 1H), 2.21 (s, 3H), 1.38 (t, J=7.28 Hz, 3H), 1.31-1.34 (m, 3H).

Example 2-13

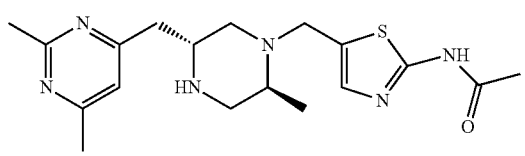 [SMILES: CC(=O)Nc1ncc(CN2C[C@@H](Cc3cc(C)nc(C)n3)NC[C@@H]2C)s1]

N-(5-4(2S,5R)-5-((2,6-dimethylpyrimidin-4-yl)methyl)-2-methylpiperazin-1-yl)methyl)thiazol-2-yl)acetamide: The title compound was prepared in an analogous manner of that in Scheme 2 from 4-bromo-2,6-dimethylpyrimidine, 1-benzyl 4-(tert-butyl) (2S,5S)-2-(bromomethyl)-5-methylpiperazine-1,4-dicarboxylate and N-(5-(chloromethyl)thiazol-2-yl)acetamide. LCMS (ESI): [M+H] 375. $^1$H NMR (400 MHz, METHANOL-d$_4$) δ7.80 (s, 1H), 7.73 (s, 1H), 4.78-4.84 (m, 1H), 4.49-4.61 (m, 1H), 4.37 (br s, 1H), 3.83 (br d, J=13.05 Hz, 1H), 3.63-3.78 (m, 2H), 3.37-3.53 (m, 3H), 3.32-3.37 (m, 1H), 2.87 (s, 3H), 2.75 (s, 3H), 2.26 (s, 3H), 1.58 (d, J=6.27 Hz, 3H).

Example 2-14

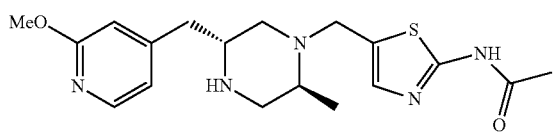 [SMILES: COc1cc(C[C@@H]2CN(Cc3cnc(NC(C)=O)s3)[C@@H](C)CN2)ccn1]

N-(5-(((2S,5R)-5-((2-methoxypyridin-4-yl)methyl)-2-methylpiperazin-1-yl)methyl)thiazol-2-yl)acetamide: The title compound was prepared in an analogous manner of that in Scheme 2 from 4-bromo-2-methoxypyridine, 1-benzyl 4-(tert-butyl) (2S,5S)-2-(bromomethyl)-5-methylpiperazine-1,4-dicarboxylate and N-(5-(chloromethyl)thiazol-2-yl)acetamide. LCMS (ESI): [M+H] 376. $^1$H NMR (400 MHz, METHANOL-d$_4$) δ8.34 (d, J=6.27 Hz, 1H), 7.63-7.75 (m, 2H), 7.49 (dd, J=1.38, 6.15 Hz, 1H), 4.77 (br d, J=14.81 Hz, 1H), 4.44-4.54 (m, 1H), 4.21-4.42 (m, 4H), 3.55-3.73 (m, 3H), 3.33-3.44 (m, 3H), 3.19-3.29 (m, 1H), 2.27 (s, 3H), 1.56 (d, J=6.27 Hz, 3H).

Example 2-15

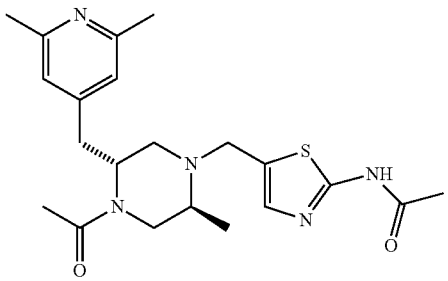

N-(5-(((2S,5R)-4-acetyl-5-((2,6-dimethylpyridin-4-yl)methyl)-2-methylpiperazin-1-yl)methyl)thiazol-2-yl)acetamide: The title compound was prepared in an analogous manner of that in example 2-4 from N-(5-(((2S,5R)-5-((2,6-dimethylpyridin-4-yl)methyl)-2-methylpiperazin-1-yl)methyl)thiazol-2-yl)acetamide. LCMS (ESI): [M+H] 416. $^1$H NMR (400 MHz, METHANOL-d$_4$) δ7.55 (d, J=4.27 Hz, 3H), 5.09 (br s, 1H), 4.56 (br s, 1H), 4.26-4.47 (m, 2H), 3.80-3.98 (m, 2H), 3.71 (br d, J=6.02 Hz, 1H), 3.13-3.28 (m, 2H), 3.06 (br d, J=12.55 Hz, 1H), 2.67 (s, 6H), 2.23 (s, 3H), 1.92-2.10 (m, 3H), 1.22-1.44 (m, 3H).

Example 2-16

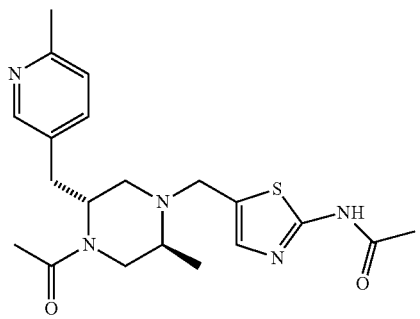

N-(5-(((2S,5R)-4-acetyl-2-methyl-5-((6-methylpyridin-3-yl)methyl)piperazin-1-yl)methyl)thiazol-2-yl)acetamide: The title compound was prepared in an analogous manner of that in example 2-4 from N-(5-(((2S,5R)-2-methyl-5-((6-methylpyridin-3-yl)methyl)piperazin-1-yl)methyl)thiazol-2-yl)acetamide. LCMS (ESI): [M+H] 402. $^1$H NMR (400 MHz, METHANOL-d$_4$) δ8.60 (d, J=1.76 Hz, 1H), 8.32 (dd, J=2.01, 8.28 Hz, 1H), 7.78 (br d, J=8.03 Hz, 1H), 7.48 (s, 1H), 5.04 (br s, 1H), 4.13-4.37 (m, 2H), 3.72-3.96 (m, 2H), 3.57 (br s, 1H), 3.35-3.48 (m, 1H), 3.06-3.25 (m, 2H), 2.99 (br d, J=12.80 Hz, 1H), 2.74 (s, 3H), 2.23 (s, 3H), 1.99 (s, 3H), 1.14-1.39 (m, 3H).

Example 2-17

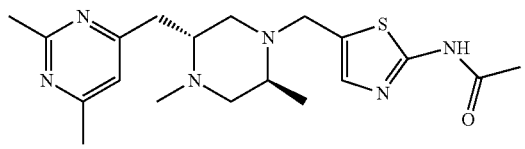 [SMILES: CC(=O)Nc1ncc(CN2C[C@@H](Cc3cc(C)nc(C)n3)N(C)C[C@@H]2C)s1]

N-(5-4(2S,5R)-5-((2,6-dimethylpyrimidin-4-yl)methyl)-2,4-dimethylpiperazin-1-yl)methyl)thiazol-2-yl)acetamide: The title compound was prepared in an analogous manner of that in example 2-2 from N-(5-(((2S,5R)-5-((2,6-dimethylpyrimidin-4-yl)methyl)-2-methylpiperazin-1-yl)methyl)thiazol-2-yl)acetamide. LCMS (ESI): [M+H] 389. $^1$H NMR (400 MHz, METHANOL-d$_4$) δ7.61 (s, 2H), 7.26 (s, 1H), 4.19 (br d, J=15.06 Hz, 1H), 3.83 (d, J=14.81 Hz, 1H), 3.43-3.66 (m, 3H), 2.83-3.04 (m, 7H), 2.70 (s, 6H), 2.39-2.53 (m, 1H), 2.21 (s, 3H), 1.30 (d, J=6.02 Hz, 3H).

Example 2-18

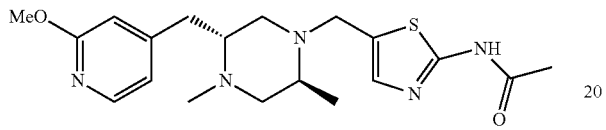

N-(5-4(2S,5R)-5-((2-methoxypyridin-4-yl)methyl)-2,4-dimethylpiperazin-1-yl)methyl)thiazol-2-yl)acetamide: The title compound was prepared in an analogous manner of that in example 2-2 from N-(5-(((2S,5R)-5-((2-methoxypyridin-4-yl)methyl)-2-methylpiperazin-1-yl)methyl)thiazol-2-yl)acetamide. LCMS (ESI): [M+H] 390. $^1$H NMR (400 MHz, METHANOL-d$_4$) δ8.01 (d, J=5.27 Hz, 1H), 7.18 (s, 1H), 6.81 (dd, J=1.38, 5.40 Hz, 1H), 6.68 (s, 1H), 4.16 (d, J=14.31 Hz, 1H), 3.88 (s, 3H), 3.68 (d, J=14.56 Hz, 1H), 3.42-3.57 (m, 2H), 3.36 (br dd, J=3.89, 13.68 Hz, 1H), 2.92-3.04 (m, 4H), 2.81 (dd, J=2.89, 13.43 Hz, 2H), 2.59-2.72 (m, 1H), 2.18-2.31 (m, 4H), 1.27 (d, J=6.27 Hz, 3H).

Intermediate 20

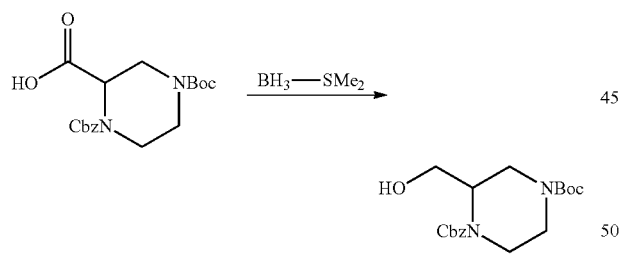

1-benzyl 4-(tert-butyl) 2-(hydroxymethyl)piperazine-1,4-dicarboxylate: Borane dimethyl sulfide complex (10 M, 1.67 mL) was added dropwise to a mixture of 1-((benzyloxy)carbonyl)-4-(tert-butoxycarbonyl)piperazine-2-carboxylic acid (3.05 g, 8.37 mmol) in THF (50.0 mL) at 0° C., then the mixture was stirred at 70° C. for 1 hour. The mixture was cooled to 0° C., quenched with MeOH and stirred at 70° C. for another 2 hours. The mixture was concentrated in vacuo and the residue was purified by column chromatography (Petroleum ether/EtOAc=3/1) on silica gel provide the title compound (1.01 g, 34% yield). $^1$H NMR (500 MHz, CDCl$_3$) δ7.31-7.37 (m, 5H), 5.10-5.17 (m, 2H), 4.17-4.33 (m, 1H), 3.92-4.02 (m, 2H), 3.62-3.73 (m, 2H), 2.75-3.34 (m, 4H), 1.46 (s, 9H).

Intermediate 21

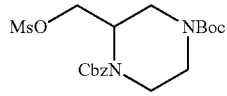

1-benzyl 4-(tert-butyl) 2-(((methylsulfonyl)oxy)methyl)piperazine-1,4-dicarboxylate: The title compound was prepared in an analogous manner of that in intermediate 15. The crude material obtained was used in the next step without any further purification.

Intermediate 22

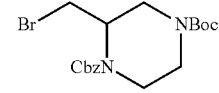

1-benzyl 4-(tert-butyl) 2-(bromomethyl)piperazine-1,4-dicarboxylate: The title compound was prepared in an analogous manner of that in intermediate 16. $^1$H NMR (500 MHz, CDCl$_3$) δ7.32-7.39 (m, 5H), 5.14-5.18 (m, 2H), 4.22-4.48 (m, 2H), 3.83-4.01 (m, 2H), 3.35-3.47 (m, 2H), 2.82-3.07 (m, 3H), 1.47 (s, 9H).

Example 2-19

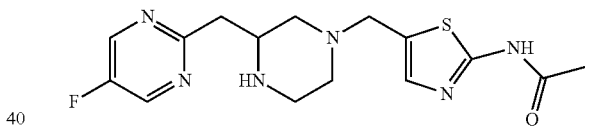

N-(5-((3-((5-fluoropyrimidin-2-yl)methyl)piperazin-1-yl)methyl)thiazol-2-yl)acetamide: The title compound was prepared in an analogous manner of that in scheme 2 from 2-bromo-5-fluoropyrimidine, 1-benzyl 4-(tert-butyl) 2-(bromomethyl)piperazine-1,4-dicarboxylate and N-(5-formylthiazol-2-yl)acetamide.

Example 2-20

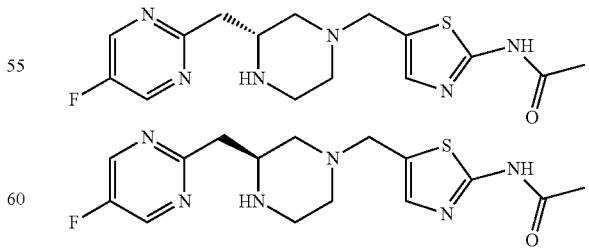

The mixture of enantiomers of Example 2-19, namely (R)—N-(5-((3-((5-fluoropyrimidin-2-yl)methyl)piperazin-1-yl)methyl)thiazol-2-yl)acetamide and (S)—N-(5-((3-((5-fluoropyrimidin-2-yl)methyl)piperazin-1-yl)methyl)thiazol- 2-yl)acetamide, was separated. The chiral separation method: SFC, Column: CHIRALPAK IC 250×30 mm, 10 um; 0.1% NH$_3$H$_2$O EtOH, Flow Rate (ml/min): 80. The products were:

Peak 1: LCMS (ESI): [M+H] 351. $^1$H NMR (400 MHz, D$_2$O) δ8.65 (s, 2H), 7.30 (s, 1H), 3.70-3.80 (m, 2H), 3.24-3.26 (m, 1H), 3.00-3.02 (m, 3H), 2.87-2.95 (m, 1H), 2.76-2.84 (m, 2H), 2.25 (s, 3H), 2.20-2.23 (m, 1H), 1.95-2.00 (m, 1H).

Peak 2: LCMS (ESI): [M+H] 351. $^1$H NMR (400 MHz, D$_2$O) δ8.65 (s, 2H), 7.30 (s, 1H), 3.70-3.80 (m, 2H), 3.24-3.26 (m, 1H), 3.00-3.02 (m, 3H), 2.87-2.95 (m, 1H), 2.76-2.84 (m, 2H), 2.25 (s, 3H), 2.20-2.23 (m, 1H), 1.95-2.00 (m, 1H).

Intermediate 23

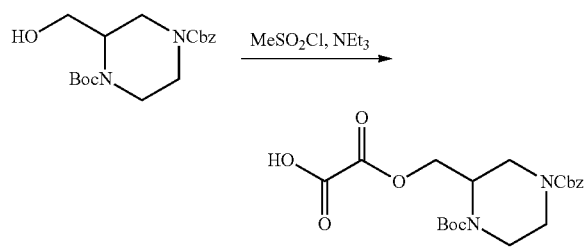

2-((4-((benzyloxy)carbonyl)-1-(tert-butoxycarbonyl)piperazin-2-yl)methoxy)-2-oxoacetic acid: A round-bottom flask was charged with 4-benzyl 1-(tert-butyl) 2-(hydroxymethyl)piperazine-1,4-dicarboxylate (8.0 g, 22.83 mmol) followed by the addition of diethyl ether (35.0 mL). The solution was cooled to 0° C. Oxalyl chloride (5.8 g, 45.66 mmol, 2.0 eq.) was added dropwise. The homogeneous reaction mixture was allowed to warm to 28° C. and stirred for 18 hours. The reaction was cooled to 0° C. and quenched by slow addition of H$_2$O (90 mL). After stirring for 1 hour at 25° C., the resulting mixture was transferred to a separatory funnel, and the aqueous layer mixture was extracted with EtOAc (20 mL×3). The combined organic layers were washed with brine, dried over Na$_2$SO$_4$, filtered and concentrated under reduced pressure to provide the title compound (3.0 g, 31% yield). LCMS (ESI): [M-Boc+H] 323.

Intermediate 24

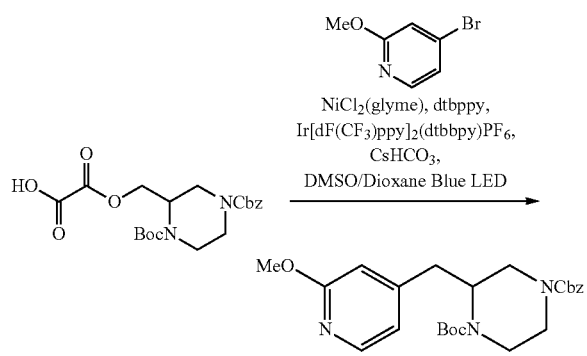

4-benzyl 1-(tert-butyl) 2-((2-methoxypyridin-4-yl)methyl)piperazine-1,4-dicarboxylate: To a suspension of 4-bromo-2-methoxypyridine (50.0 mg, 0.265 mmol) and 2-((4-((benzyloxy)carbonyl)-1-(tert-butoxycarbonyl)piperazin-2-yl)methoxy)-2-oxoacetic acid (112.3 mg, 0.265 mmol, 1.0 eq.) in Dioxane (16.0 mL) and DMSO (4.0 mL) were added NiCl$_2$ glyme (5.8 mg, 26.59 umol), Ir[dF(CF$_3$)ppy]$_2$(dtbbpy)PF$_6$ (3.0 mg, 2.66 umol), 4-tert-butyl-2-(4-tert-butyl-2-pyridyl)pyridine (10.7 mg, 39.89 umol) and CsHCO$_3$ (154.7 mg, 797.79 umol). The mixture was stirred and irradiated with blue LEDs at 60° C. for 60 h under N$_2$. The reaction mixture was concentrated and the residue was treated with water (20 mL), extracted with EtOAc (2×20 mL). The combined organic phases were washed with water (2×20 mL), brine (20 mL), dried over anhydrous Na$_2$SO$_4$, filtered and concentrated. The residue was purified by prep-TLC (Petroleum ether:EtOAc=3:1) to afford 20 mg of impure product, which was purified by prep-HPLC ((0.04% NH$_3$H$_2$O+10 mM NH$_4$HCO$_3$); Mobile phase B: acetonitrile; Column: water Xbridge Prep OBD C18 150×30×5 um; Detection wavelength: 220 nm) to afford the title compound (5.0 mg, 4.26% yield). $^1$H NMR (400 MHz, CDCl$_3$) δ8.07-7.93 (m, 1H), 7.36-7.33 (m, 5H), 6.74-6.53 (m, 2H), 5.29-5.11 (m, 2H), 4.11-3.92 (m, 4H), 3.92 (s, 3H), 3.08-2.95 (m, 3H), 2.72-2.71 (m, 2H), 1.43 (s, 9H).

Intermediate 25

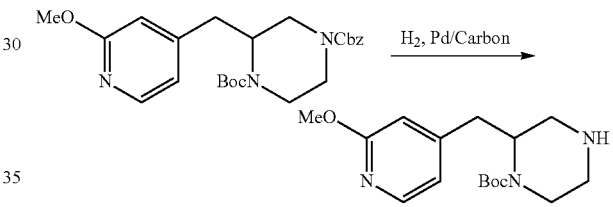

tert-butyl 2-((2-methoxypyridin-4-yl)methyl)piperazine-1-carboxylate: To a solution of 4-benzyl 1-(tert-butyl) 2-((2-methoxypyridin-4-yl)methyl)piperazine-1,4-dicarboxylate (80.0 mg, 0.181 mmol) in MeOH (5.0 mL) was added Pd/C (28.9 mg, 0.271 mmol). The reaction mixture was stirred at 30° C. for 3 hours under 40 psi of H$_2$(g). The reaction mixture was filtered and concentrated in vacuo to provide the title compound (50.0 mg, 89% yield). LCMS (ESI): [M+H] 308.

Intermediate 26

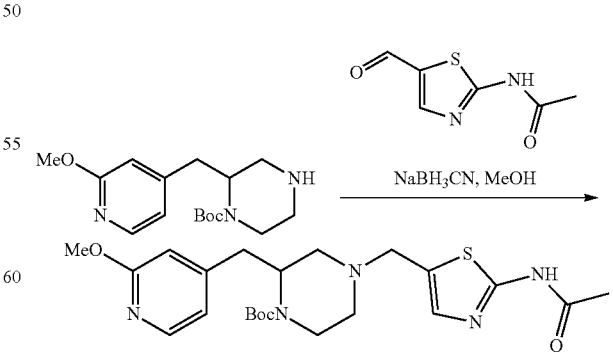

tert-butyl-4-((2-acetamidothiazol-5-yl)methyl)-2-((2-methoxypyridin-4-yl)methyl)piperazine-1-carboxylate: To a solution of tert-butyl 2-((2-methoxypyridin-4-yl)methyl)

piperazine-1-carboxylate (50.0 mg, 0.162 mmol) and N-(5-formylthiazol-2-yl)acetamide (41.52 mg, 0.244 mmol) in MeOH (5.0 mL) was stirred at 50° C. for 0.5 hour. Sodium cyanoborohydride (25.6 mg, 0.406 mmol) was added and the mixture was stirred at 50° C. for 16 hours. The reaction mixture was purified by pre-TLC (Petroleum ether/EtOAc=1/1) to provide the title compound (70.0 mg, 93% yield). LCMS (ESI): [M+H] 462.

Example 2-21

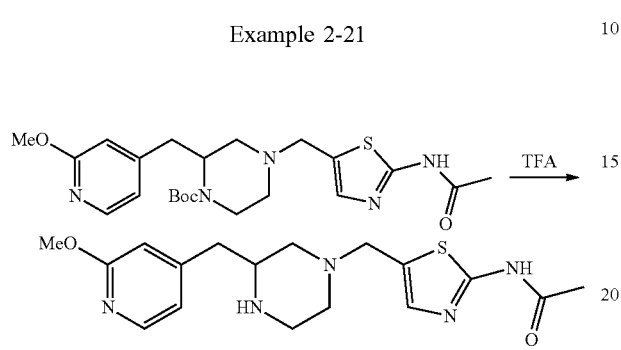

N-(5-((3-((2-methoxypyridin-4-yl)methyl)piperazin-1-yl)methyl)thiazol-2-yl)acetamide: To a solution of tert-butyl 4-((2-acetamidothiazol-5-yl)methyl)-2-((2-methoxypyridin-4-yl)methyl)piperazine-1-carboxylate (70.0 mg, 0.151 mmol) in DCM (10.0 mL) was added TFA (1.0 mL). The reaction mixture was stirred at 30° C. for 1 hour. The reaction mixture was concentrated and basified with $NH_3H_2O$ until pH 9. The residue was purified by preparative HPLC (Mobile phase: water (10 mM $NH_4HCO_3$)-ACN; Column: xtimate prep OBD $C_{18}$ 150×25 mm×5 um; Detection wavelength: 220 nm) to provide the title compound (30.0 mg, 54% yield). LCMS (ESI): [M+H] 362. The resulting enantiomers were separated using chiral SFC.

Example 2-22

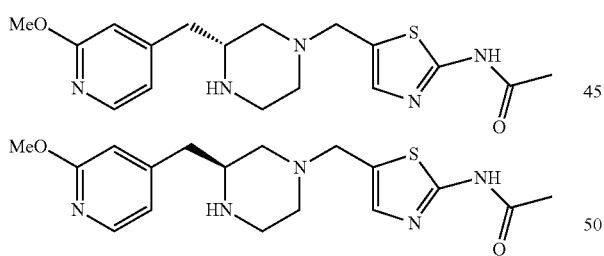

The mixture of enantiomers of Example 2-21, namely (R)—N-(5-((3-((2-methoxypyridin-4-yl)methyl)piperazin-1-yl)methyl)thiazol-2-yl)acetamide and (S)—N-(5-((3-((2-methoxypyridin-4-yl)methyl)piperazin-1-yl)methyl)thiazol-2-yl)acetamide, was separated. The chiral separation method: SFC, Column: DAICEL CHIRALPAK AD (250 mm×30 mm, 10 um); ethanol (0.1% $NH_3H_2O$) in $CO_2$. The products were:

Peak 1: LCMS (ESI): [M+H] 362. $^1$H NMR (400 MHz, METHANOL-$d_4$) δ8.02 (d, J=5.2 Hz, 1H), 7.22 (s, 1H), 6.82 (t, J=5.2 Hz, 1H), 6.66 (s, 1H), 3.87 (s, 3H), 3.70 (s, 2H), 3.20-3.18 (m, 1H), 3.08-3.04 (m, 1H), 2.89-2.80 (m, 3H), 2.74-2.71 (m, 2H), 2.24-2.19 (m, 1H), 2.19 (s, 3H), 2.02-1.99 (m, 1H).

Peak 2: LCMS (ESI): [M+H] 362. $^1$H NMR (400 MHz, METHANOL-$d_4$) δ8.01 (d, J=5.2 Hz, 1H), 7.21 (s, 1H), 6.84-6.82 (m, 1H), 6.66 (s, 1H), 3.88 (s, 3H), 3.69 (s, 2H), 3.16-3.02 (m, 2H), 2.87-2.80 (m, 3H), 2.72-2.69 (m, 2H), 2.23-2.19 (m, 1H), 2.19 (s, 3H), 1.99-1.94 (m, 1H).

Intermediate 27

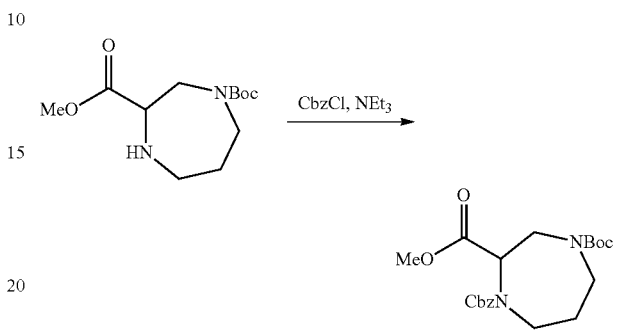

1-benzyl 4-(tert-butyl) 2-methyl 1,4-diazepane-1,2,4-tricarboxylate: To a stirred solution of 1-(tert-butyl) 3-methyl 1,4-diazepane-1,3-dicarboxylate (5.00 g, 19.36 mmol) and triethylamine (4.11 g, 41 mmol, 5.6 mL) at 0° C. in dichloromethane (120 mL) was dropwise added benzyl carbonochloridate (3.63 g, 21.3 mmol, 3.0 mL). The resulting mixture warmed to room temperature and stirred at rt for 1 h. The reaction was then quenched by addition of water. The organic layer was washed with water, then brine. The organic layer was then separated, dried over magnesium sulfate and concentrated. The residue was purified by chromatography on silica gel (0-100% EtOAc in heptane) to provide the title compound (6.80 g, 89% yield). LCMS (ESI): [M-Boc] 293. $^1$H NMR (400 MHz, METHANOL-$d_4$) δ7.23-7.43 (m, 5H), 5.15-5.25 (m, 1H), 4.99-5.13 (m, 2H), 4.15-4.32 (m, 1H), 3.84-4.07 (m, 2H), 3.65-3.77 (m, 3H), 3.11-3.29 (m, 2H), 2.72-3.02 (m, 1H), 1.69-1.89 (m, 1H), 1.51-1.67 (m, 1H), 1.33-1.45 (m, 9H).

Intermediate 28

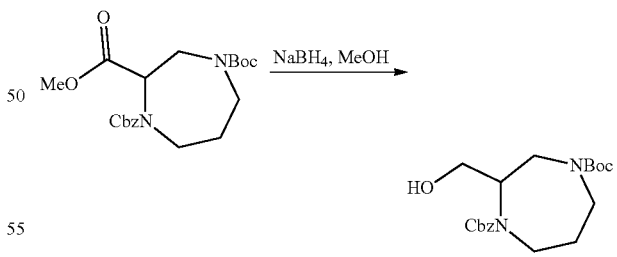

1-benzyl 4-(tert-butyl) 2-(hydroxymethyl)-1,4-diazepane-1,4-dicarboxylate: To a solution of 1-benzyl 4-(tert-butyl) 2-methyl 1,4-diazepane-1,2,4-tricarboxylate (1.00 g, 2.55 mmol) in methanol (10 mL) was added sodium borohydride (145 mg, 3.82 mmol) in small portions at 0° C. The reaction was stirred at rt for 2 h. Sodium borohydride (50 mg) was then added. The reaction stirred for 30 min. Another portion of sodium borohydride (50 mg) was added. Stirred for another 30 min. The reaction was quenched with brine. The mixture was concentrated in vacuo and the residue was diluted with ethyl acetate, washed with brine, dried and the residue was purified by chromatography on silica gel (0-100% EtOAc in heptane) to give provide the title compound (855 mg, 92% yield). LCMS (ESI): [M+Na] 387. ¹H NMR (400 MHz, METHANOL-d₄) δ7.22-7.42 (m, 5H), 5.03-5.23 (m, 2H), 4.45-4.69 (m, 1H), 3.88-4.10 (m, 3H), 3.51-3.65 (m, 2H), 3.16-3.27 (m, 1H), 2.97-3.14 (m, 1H), 2.71-2.93 (m, 1H), 1.76 (br s, 1H), 1.48-1.61 (m, 1H), 1.33-1.45 (m, 9H).

Intermediate 29

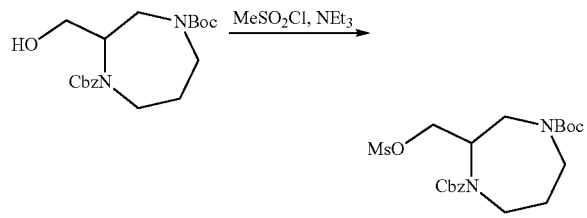

1-benzyl 4-(tert-butyl) 2-(((methylsulfonyl)oxy)methyl)-1,4-diazepane-1,4-dicarboxylate: Methanesulfonyl chloride (320 mg, 2.80 mmol, 216 uL) was added dropwise to a solution of 1-benzyl 4-(tert-butyl) 2-(hydroxymethyl)-1,4-diazepane-1,4-dicarboxylate (850 mg, 2.33 mmol) and triethylamine (589 mg, 5.83 mmol, 807 uL) in ether (10 mL) at 0° C. The reaction was then warmed to room temperature. After 2 h, the reaction was diluted with ethyl acetate and washed with brine, dried over MgSO₄ and evaporated to provide the title compound (880 mg, 85% yield) which was used in the next step without further purifications. LCMS (ESI): [M+Na] 465; ¹H NMR (400 MHz, METHANOL-d4) δ7.22-7.50 (m, 5H), 5.01-5.28 (m, 2H), 4.15-4.47 (m, 2H), 3.79-4.12 (m, 3H), 3.38-3.79 (m, 1H), 3.14-3.26 (m, 1H), 2.95-3.12 (m, 3H), 2.72-2.94 (m, 1H), 1.73-1.94 (m, 1H), 1.51-1.65 (m, 1H), 1.28-1.50 (m, 9H).

Intermediate 30

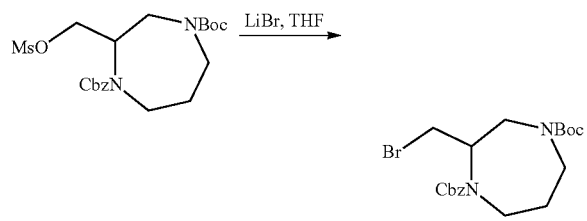

1-benzyl 4-(tert-butyl) 2-(bromomethyl)-1,4-diazepane-1,4-dicarboxylate: To a solution of 1-benzyl 4-(tert-butyl) 2-(((methylsulfonyl)oxy)methyl)-1,4-diazepane-1,4-dicarboxylate 870 mg, 1.97 mmol) in tetrahydrofuran (15 mL) was added lithium bromide (1.37 g, 15.76 mmol). The reaction mixture was then heated at 50° C. for 6 h, cooled to rt and subsequently concentrated in vacuo. The residue was diluted with dichloromethane, a white precipitate formed and was removed by filtration. The eluent was concentrated and purified by chromatography on silica gel (0-100% EtOAc in heptane) to provide the title compound (125 mg, 15% yield). LCMS (ESI): [M+Na] 449/451. ¹H NMR (400 MHz, CHLOROFORM-d) δ7.29-7.45 (m, 5H), 5.06-5.26 (m, 2H), 4.57-4.89 (m, 1H), 3.91-4.25 (m, 3H), 3.29-3.58 (m, 2H), 2.64-3.27 (m, 3H), 1.67-2.00 (m, 2H), 1.36-1.53 (m, 9H).

Intermediate 31

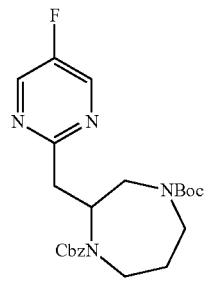 [SMILES: CC(C)(C)OC(=O)N1CCCN(C(=O)OCc2ccccc2)C(Cc2ncc(F)cn2)C1]

1-Benzyl 4-(tert-butyl) 2-((5-fluoropyrimidin-2-yl)methyl)-1,4-diazepane-1,4-dicarboxylate: The title compound was prepared in an analogous manner to intermediate 1 from 2-bromo-5-fluoropyrimidine and 1-benzyl 4-(tert-butyl) 2-(bromomethyl)-1,4-diazepane-1,4-dicarboxylate. LCMS (ESI): [M+H] 445. ¹H NMR (400 MHz, METHANOL-d4) δ8.31-8.51 (m, 2H), 7.09-7.44 (m, 5H), 4.88-5.10 (m, 2H), 4.68-4.80 (m, 1H), 3.84-4.12 (m, 3H), 3.12-3.26 (m, 1H), 2.93-3.08 (m, 3H), 2.76-2.92 (m, 1H), 1.73-1.93 (m, 1H), 1.58 (br s, 1H), 1.33-1.44 (m, 9H).

Intermediate 32

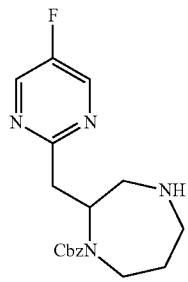 [SMILES: O=C(OCc1ccccc1)N1CCCNCC1Cc1ncc(F)cn1]

Benzyl 2-((5-fluoropyrimidin-2-yl)methyl)-1,4-diazepane-1-carboxylate hydrochloride: The title compound was prepared in an analogous manner to intermediate 2 from 1-benzyl 4-(tert-butyl) 2-((5-fluoropyrimidin-2-yl)methyl)-1,4-diazepane-1,4-dicarboxylate. LCMS (ESI): [M+H] 345.

Intermediate 33

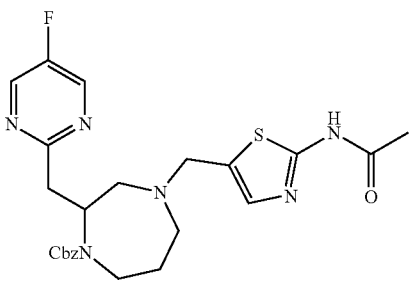 [SMILES: CC(=O)Nc1ncc(CN2CCCN(C(=O)OCc3ccccc3)C(Cc3ncc(F)cn3)C2)s1]

Benzyl 4-((2-acetamidothiazol-5-yl)methyl)-2-((5-fluoropyrimidin-2-yl)methyl)-1,4-diazepane-1-carboxylate: The title compound was prepared in an analogous manner to intermediate 19 from benzyl 2-[(5-fluoropyrimidin-2-yl)methyl]-1,4-diazepane-1-carboxylate hydrochloride and N-[5-(chloromethyl) thiazol-2-yl] acetamide. LCMS (ESI): [M+H] 499; $^1$H NMR (400 MHz, METHANOL-d4) δ8.27-8.46 (m, 2H), 7.26-7.41 (m, 4H), 7.14-7.24 (m, 2H), 4.96-5.07 (m, 1H), 4.89-4.94 (m, 0.5H), 4.73-4.79 (m, 0.5H), 4.49-4.66 (m, 1H), 3.72-3.92 (m, 3H), 3.07-3.21 (m, 2H), 2.81-3.05 (m, 3H), 2.51-2.69 (m, 2H), 2.20 (d, J=2.76 Hz, 3H), 1.77-1.97 (m, 1H), 1.63 (br d, J=10.54 Hz, 1H).

Example 2-23

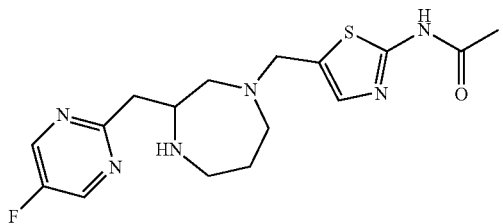 [SMILES: CC(=O)Nc1ncc(CN2CCCNC(Cc3ncc(F)cn3)C2)s1]

N-(5-((3-((5-fluoropyrimidin-2-yl)methyl)-1,4-diazepan-1-yl)methyl)thiazol-2-yl)acetamide: The title compound was prepared in an analogous manner to example 2-1 from benzyl 4-((2-acetamidothiazol-5-yl) methyl)-2-((5-fluoropyrimidin-2-yl) methyl)-1,4-diazepane-1-carboxylate. LCMS (ESI): [M+H] 365. $^1$H NMR (400 MHz, METHANOL-d$_4$) δ8.67 (s, 2H), 7.73 (s, 1H), 4.69-4.80 (m, 2H), 4.58 (br s, 1H), 4.00 (dd, J=8.53, 15.31 Hz, 1H), 3.74-3.87 (m, 2H), 3.48-3.70 (m, 5H), 2.40-2.56 (m, 2H), 2.26 (s, 3H).

Example 2-24

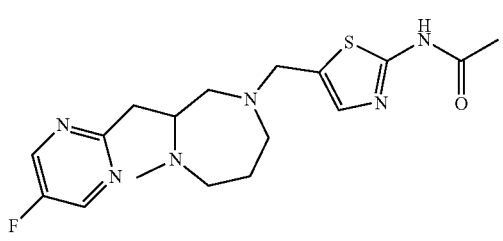 [SMILES: CC(=O)Nc1ncc(CN2CCCN(C)C(Cc3ncc(F)cn3)C2)s1]

N-(5-((3-((5-fluoropyrimidin-2-yl)methyl)-4-methyl-1,4-diazepan-1-yl)methyl)thiazol-2-yl)acetamide: The title compound was prepared in an analogous manner to example 2-2 from N-[5-[[3-[(5-fluoropyrimidin-2-yl)methyl]-1,4-diazepan-1-yl]methyl]thiazol-2-yl]acetamide. LCMS (ESI): [M+H] 379. $^1$H NMR (400 MHz, METHANOL-d$_4$) δ8.59 (s, 2H), 7.15 (s, 1H), 3.92 (br s, 1H), 3.78-3.88 (m, 2H), 3.52-3.63 (m, 2H), 3.40 (d, J=6.78 Hz, 2H), 3.01-3.11 (m, 5H), 2.80-2.97 (m, 2H), 2.08-2.27 (m, 5H).

Example 2-25

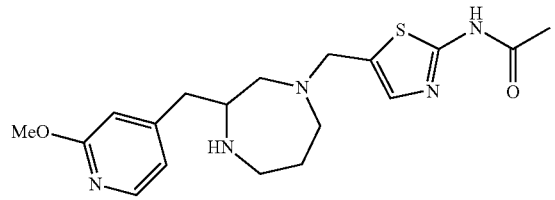 [SMILES: COc1cc(CC2CN(Cc3cnc(NC(C)=O)s3)CCCN2)ccn1]

N-(5-((3-((2-methoxypyridin-4-yl)methyl)-1,4-diazepan-1-yl)methyl)thiazol-2-yl)acetamide: The title compound was prepared in an analogous manner of that in scheme 2 from 4-bromo-2-methoxypyridine, 1-benzyl 4-(tert-butyl) 2-(bromomethyl)-1,4-diazepane-1,4-dicarboxylate and N-(5-(chloromethyl)thiazol-2-yl)acetamide. LCMS (ESI): [M+H] 376. $^1$H NMR (400 MHz, METHANOL-d$_4$) δ8.32 (d, J=6.02 Hz, 1H), 7.79 (s, 1H), 7.71 (s, 1H), 7.59 (d, J=5.77 Hz, 1H), 4.70 (s, 2H), 4.31 (s, 3H), 3.94-4.05 (m, 1H), 3.76 (br dd, J=6.65, 13.43 Hz, 1H), 3.56-3.72 (m, 3H), 3.44-3.56 (m, 3H), 3.36-3.43 (m, 1H), 2.52 (br t, J=8.91 Hz, 1H), 2.36-2.45 (m, 1H), 2.27 (s, 3H).

Example 2-26

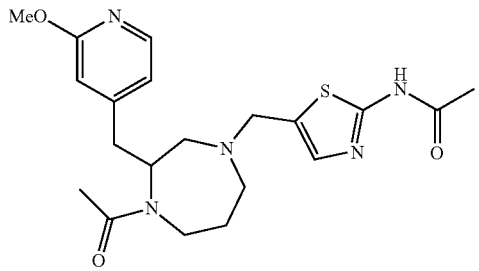 [SMILES: COc1cc(CC2CN(Cc3cnc(NC(C)=O)s3)CCCN2C(C)=O)ccn1]

N-(5-((4-acetyl-3-((2-methoxypyridin-4-yl)methyl)-1,4-diazepan-1-yl)methyl)thiazol-2-yl)acetamide: The title compound was prepared in an analogous manner to example 2-4 from N-(5-((3-((2-methoxypyridin-4-yl)methyl)-1,4-diazepan-1-yl)methyl)thiazol-2-yl)acetamide hydrobromide. LCMS (ESI): [M+H] 418. $^1$H NMR (400 MHz, METHANOL-d$_4$) δ7.90-8.02 (m, 1H), 7.11-7.23 (m, 1H), 6.72-6.78 (m, 1H), 6.59 (d, J=7.53 Hz, 1H), 4.54-4.74 (m, 1H), 3.99-4.19 (m, 1H), 3.86 (d, J=2.01 Hz, 3H), 3.67-3.84 (m, 2H), 3.14 (dd, J=6.40, 15.18 Hz, 1H), 2.85-3.03 (m, 2H), 2.45-2.80 (m, 3H), 2.20 (d, J=1.76 Hz, 3H), 1.92-2.16 (m, 4H), 1.77-1.90 (m, 1H), 1.58 (br d, J=12.55 Hz, 1H).

Example 2-27

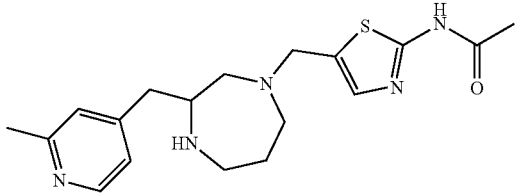 [SMILES: CC(=O)Nc1ncc(CN2CCCNC(Cc3ccnc(C)c3)C2)s1]

N-(5-((3-((2-methylpyridin-4-yl)methyl)-1,4-diazepan-1-yl)methyl)thiazol-2-yl)acetamide: The title compound was prepared in an analogous manner of that in scheme 2 from 4-bromo-2-methylpyridine, 1-benzyl 4-(tert-butyl) 2-(bromomethyl)-1,4-diazepane-1,4-dicarboxylate and N-(5-(chloromethyl)thiazol-2-yl)acetamide. LCMS (ESI): [M+H] 360. $^1$H NMR (400 MHz, METHANOL-d$_4$) δ8.67 (d, J=6.02 Hz, 1H), 8.13 (s, 1H), 8.01 (br d, J=6.02 Hz, 1H), 7.70 (s, 1H), 4.64-4.76 (m, 2H), 4.01 (dd, J=9.03, 15.56 Hz, 1H), 3.70-3.79 (m, 1H), 3.59-3.70 (m, 2H), 3.40-3.59 (m, 5H), 2.83 (s, 3H), 2.46-2.60 (m, 1H), 2.34-2.45 (m, 1H), 2.26 (s, 3H).

Example 2-28

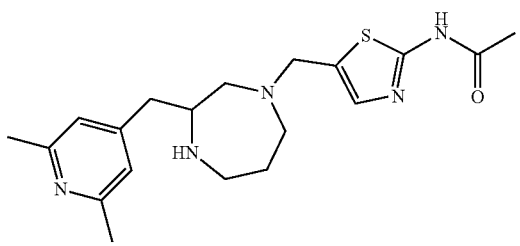 [SMILES: CC(=O)Nc1ncc(CN2CCCNC(Cc3cc(C)nc(C)c3)C2)s1]

N-(5-((3-((2,6-dimethylpyridin-4-yl)methyl)-1,4-diazepan-1-yl)methyl)thiazol-2-yl)acetamide: The title compound was prepared in an analogous manner of that in scheme 2 from 4-bromo-2,6-dimethylpyridine, 1-benzyl 4-(tert-butyl) 2-(bromomethyl)-1,4-diazepane-1,4-dicarboxylate and N-(5-(chloromethyl)thiazol-2-yl)acetamide. LCMS (ESI): [M+H] 374. $^1$H NMR (400 MHz, METHANOL-d$_4$) δ7.86 (s, 2H), 7.73 (s, 1H), 4.78-4.85 (m, 1H), 4.72 (s, 2H), 4.03 (dd, J=8.91, 15.43 Hz, 1H), 3.77 (br dd, J=6.53, 13.55 Hz, 1H), 3.64 (dt, J=3.01, 7.03 Hz, 2H), 3.45-3.59 (m, 3H), 3.33-3.39 (m, 1H), 2.77 (s, 6H), 2.48-2.64 (m, 1H), 2.33-2.46 (m, 1H), 2.25-2.32 (m, 3H)

Example 2-29

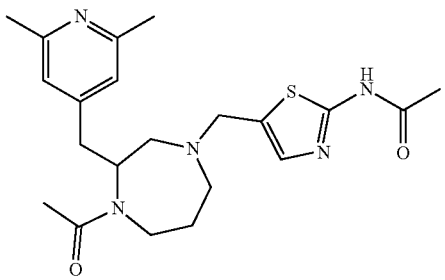 [SMILES: CC(=O)Nc1ncc(CN2CCCN(C(C)=O)C(Cc3cc(C)nc(C)c3)C2)s1]

N-(5-((4-acetyl-3-((2,6-dimethylpyridin-4-yl)methyl)-1,4-diazepan-1-yl)methyl)thiazol-2-yl)acetamide: The title compound was prepared in an analogous manner of that in example 2-4 from N-(5-((3-((2,6-dimethylpyridin-4-yl)methyl)-1,4-diazepan-1-yl)methyl)thiazol-2-yl)acetamide. LCMS (ESI): [M+H] 416. $^1$H NMR (400 MHz, METHANOL-d$_4$) δ7.16 (d, J=18.57 Hz, 1H), 6.91 (d, J=19.58 Hz, 2H), 4.00-4.69 (m, 1H), 3.63-3.93 (m, 3H), 2.91-3.16 (m, 2H), 2.65-2.91 (m, 2H), 2.41-2.61 (m, 9H), 2.20 (s, 3H), 2.01-2.15 (m, 3H), 1.78-1.90 (m, 2H).

Example 2-30

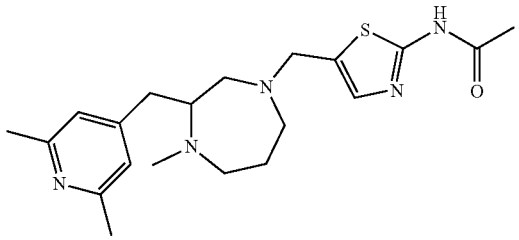 [SMILES: CC(=O)Nc1ncc(CN2CCCN(C)C(Cc3cc(C)nc(C)c3)C2)s1]

N-(5-((3-((2,6-dimethylpyridin-4-yl)methyl)-4-methyl-1,4-diazepan-1-yl)methyl)thiazol-2-yl)acetamide: The title compound was prepared in an analogous manner of that in scheme 2 from N-(5-((3-((2,6-dimethylpyridin-4-yl)methyl)-1,4-diazepan-1-yl)methyl)thiazol-2-yl)acetamide. LCMS (ESI): [M+H] 388.

Scheme 3

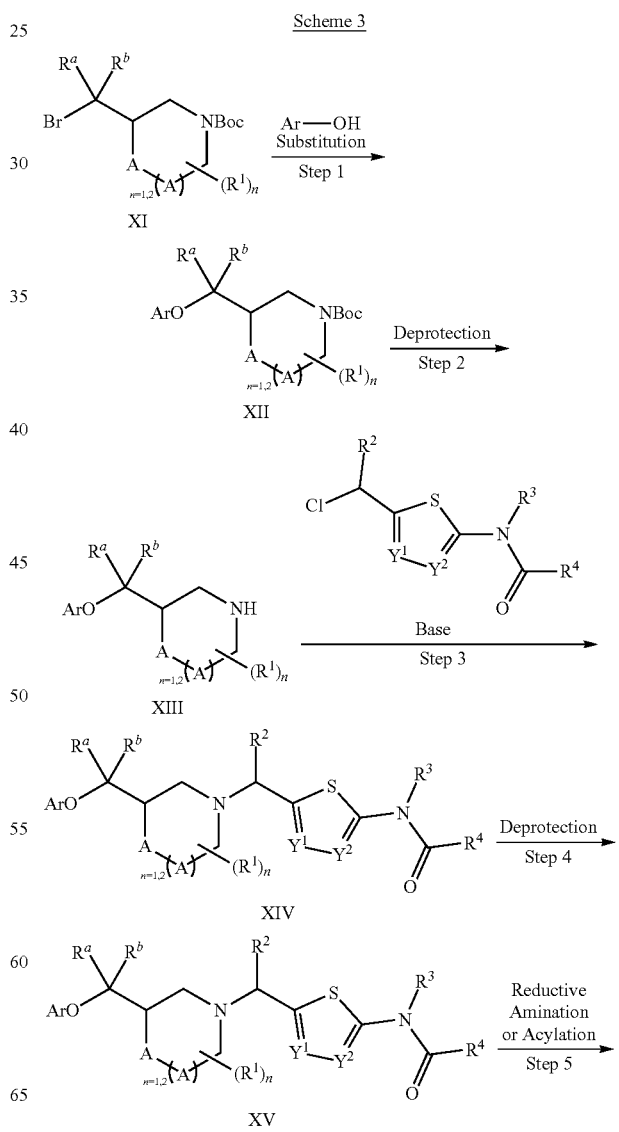

-continued

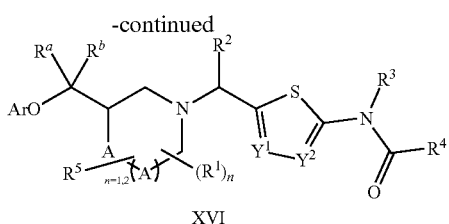

XVI

A = O, NPg, CH$_2$, CHR$^1$
independently substituted

Intermediate 34

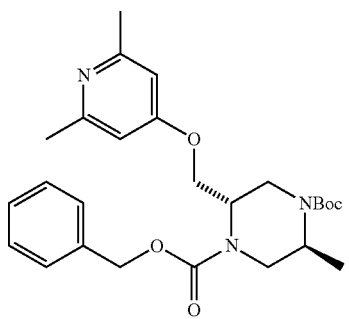

1-Benzyl 4-(tert-butyl) (2S,5S)-2-(((2,6-dimethylpyridin-4-yl)oxy)methyl)-5-methylpiperazine-1,4-dicarboxylate: To a mixture of 2,6-dimethylpyridin-4-ol (255 mg, 2.1 mmol, 193 uL) and K$_2$CO$_3$ (572 mg, 4.2 mmol) in DMF (2 mL) was added a solution of 1-benzyl 4-(tert-butyl) (2S,5S)-2-(bromomethyl)-5-methylpiperazine-1,4-dicarboxylate (885 mg, 2.1 mmol) in DMF (2 mL). The reaction mixture was then heated at 80° C. for 2 h. Remove all the solvent under vacuo. The residue was purified by chromatography on silica gel (0-100% EtOAc:heptane) to provide the title product (116 mg, 12% yield). LCMS (ESI): [M+H] 470. $^1$H NMR (400 MHz, METHANOL-d$_4$) δ7.25-7.44 (m, 5H), 6.50-6.75 (m, 2H), 5.04-5.24 (m, 2H), 4.43-4.70 (m, 1H), 4.21-4.42 (m, 1H), 4.14-4.21 (m, 1H), 3.93-4.07 (m, 1H), 3.81 (br, d, = 13.55 Hz, 1H), 3.33-3.40 (m, 1H), 3.21-3.30 (m, 1H), 2.40 (br, d, =15.56 Hz, 6H), 1.29-1.51 (m, 9H), 1.17 (t, =7.53 Hz, 3H).

Intermediate 35

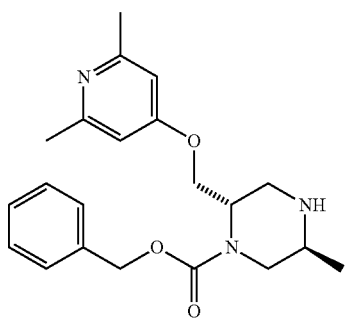

Benzyl (2S,5S)-2-(((2,6-dimethylpyridin-4-yl)oxy)methyl)-5-methylpiperazine-1-carboxylate The title compound was prepared in an analogous manner of that in scheme 3 from 1-benzyl 4-(tert-butyl) (2S,5S)-2-(((2,6-dimethylpyridin-4-yl)oxy)methyl)-5-methylpiperazine-1,4-dicarboxylate. LCMS (ESI): [M+H] 370.

Intermediate 36

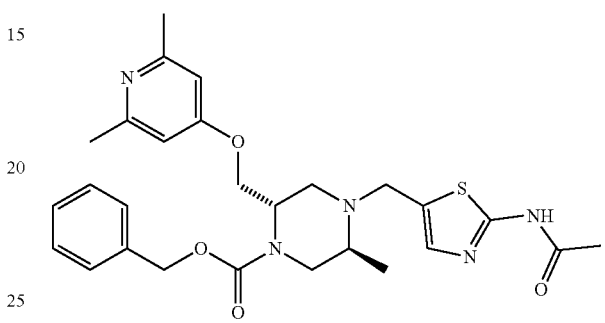

Benzyl (2S,5S)-4-((2-acetamidothiazol-5-yl)methyl)-2-(((2,6-dimethylpyridin-4-yl)oxy)methyl)-5-methylpiperazine-1-carboxylate: The title compound was prepared in an analogous manner of that in scheme 3 from benzyl (2S,5S)-2-(((2,6-dimethylpyridin-4-yl)oxy)methyl)-5-methylpiperazine-1-carboxylate and N-(5-(chloromethyl)thiazol-2-yl)acetamide. LCMS (ESI): [M+H] 524.

Example 3-1

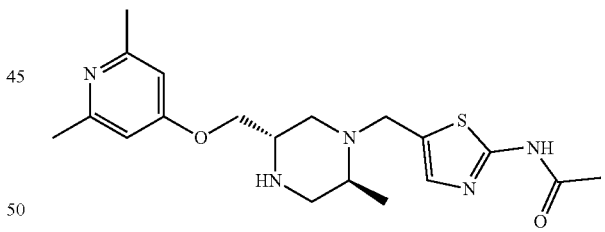

N-(5-(((2S,5S)-5-(((2,6-dimethylpyridin-4-yl)oxy)methyl)-2-methylpiperazin-1-yl)methyl)thiazol-2-yl)acetamide: The title compound was prepared in an analogous manner of that in scheme 3 from benzyl (2S,5S)-4-((2-acetamidothiazol-5-yl)methyl)-2-(((2,6-dimethylpyridin-4-yl)oxy)methyl)-5-methylpiperazine-1-carboxylate. LCMS (ESI): [M+H] 390. $^1$H NMR (400 MHz, METHANOL-d$_4$) δ7.74 (s, 1H), 7.36 (s, 2H), 4.82 (br d, J=14.56 Hz, 1H), 4.58-4.72 (m, 2H), 4.46 (br d, J=14.56 Hz, 1H), 4.26 (br d, J=8.78 Hz, 1H), 3.73 (dt, J=3.01, 13.43 Hz, 3H), 3.33-3.51 (m, 2H), 2.69 (s, 6H), 2.27 (s, 3H), 1.59 (d, J=6.27 Hz, 3H).

Example 3-2

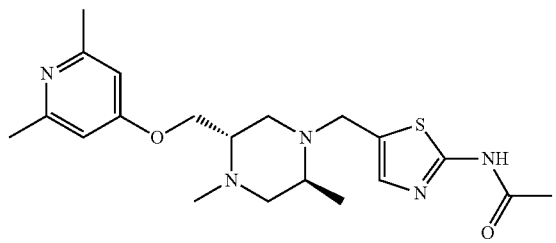 [SMILES: CC(=O)Nc1ncc(CN2C[C@@H](COc3cc(C)nc(C)c3)N(C)C[C@@H]2C)s1]

N-(5-(((2S,5S)-5-(((2,6-dimethylpyridin-4-yl)oxy)methyl)-2,4-dimethylpiperazin-1-yl)methyl)thiazol-2-yl)acetamide: The title compound was prepared in an analogous manner of that in example 2-2 from N-(5-(((2S,5S)-5-(((2,6-dimethylpyridin-4-yl)oxy)methyl)-2-methylpiperazin-1-yl)methyl)thiazol-2-yl)acetamide. LCMS (ESI): [M+H]404. $^1$H NMR (400 MHz, METHANOL-$d_4$) δ.

Example 3-3

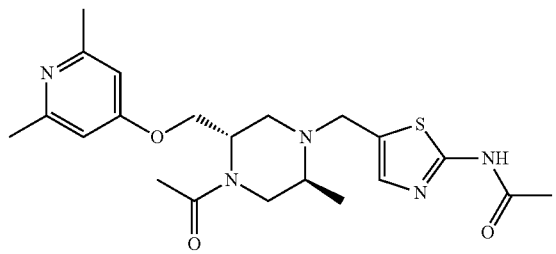 [SMILES: CC(=O)Nc1ncc(CN2C[C@@H](COc3cc(C)nc(C)c3)N(C(C)=O)C[C@@H]2C)s1]

N-(5-4(2S,5S)-4-acetyl-5-(((2,6-dimethylpyridin-4-yl)oxy)methyl)-2-methylpiperazin-1-yl)methyl)thiazol-2-yl)acetamide: The title compound was prepared in an analogous manner of that in example 2-4 from N-(5-(((2S,5S)-5-(((2,6-dimethylpyridin-4-yl)oxy)methyl)-2-methylpiperazin-1-yl)methyl)thiazol-2-yl)acetamide. LCMS (ESI): [M+H]432. $^1$H NMR (400 MHz, METHANOL-$d_4$) δ.

Example 3-4

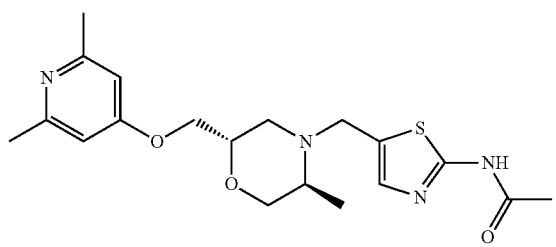 [SMILES: CC(=O)Nc1ncc(CN2C[C@@H](COc3cc(C)nc(C)c3)OC[C@@H]2C)s1]

N-(5-(((2S,5S)-2-(((2,6-dimethylpyridin-4-yl)oxy)methyl)-5 methylmorpholino)methyl)thiazol-2-yl)acetamide: The title compound was prepared in an analogous manner of that in scheme 3 from (2S,5S)-2-(((2,6-dimethylpyridin-4-yl)oxy)methyl)-5-methylmorpholine N-[5-(chloromethyl)thiazol-2-yl]acetamide. LCMS (ESI): [M+H] 391. $^1$H NMR (400 MHz, METHANOL-$d_4$) δ.

Intermediate 37

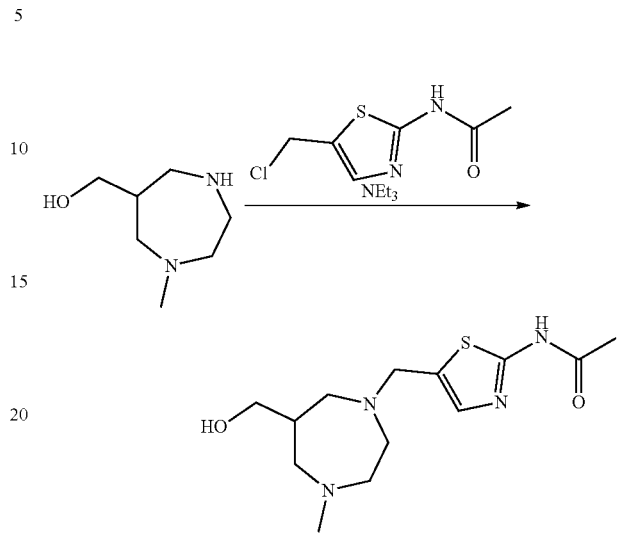

N-(5-((6-(hydroxymethyl)-4-methyl-1,4-diazepan-1-yl)methyl)thiazol-2-yl)acetamide: To a mixture of (1-methyl-1,4-diazepan-6-yl)methanol (1.0 g, 6.6 mmol) and N-[5-(chloromethyl)thiazol-2-yl]acetamide (1.26 g, 6.6 mmol) in acetonitrile (20 mL) and DMF (1.0 mL) was added Hunig's base (1.70 g, 13.18 mmol, 2.30 mL). The reaction was stirred at rt for 4 h. The mixture was concentrated in vacuo and the residue was purified by chromatography on silica gel (50-100% EtOAc-EtOH 3:1 with 2% NH$_4$OH in heptane) to provide the title compound (1.2 g, 55% yield). LCMS (ESI): [M+H] 299. $^1$H NMR (400 MHz, METHANOL-$d_4$) δ7.23 (s, 1H), 3.82 (s, 2H), 3.36-3.45 (m, 2H), 2.81-2.92 (m, 3H), 2.61-2.80 (m, 4H), 2.56 (dd, J=8.78, 12.55 Hz, 1H), 2.47 (s, 3H), 2.20 (s, 3H), 2.06-2.16 (m, 1H).

Example 3-5

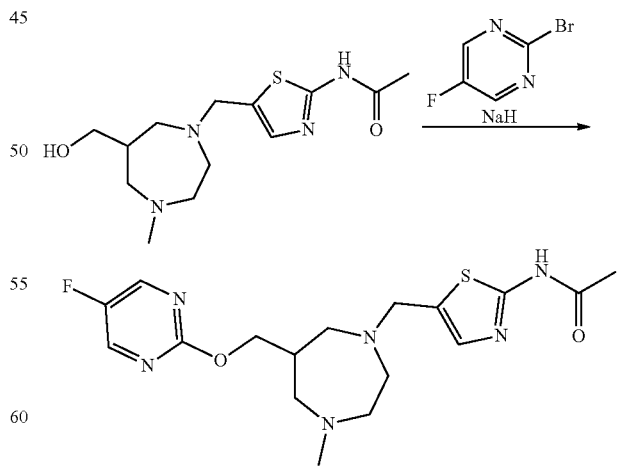

N-(5-((6-(((5-fluoropyrimidin-2-yl)oxy)methyl)-4-methyl-1,4-diazepan-1-yl)methyl)thiazol-2-yl)acetamide:
To a solution of N-[5-[[6-(hydroxymethyl)-4-methyl-1,4-diazepan-1-yl]methyl]thiazol-2-yl]acetamide (100 mg, 335 umol) and 2-bromo-5-fluoro-pyrimidine (59 mg, 335 umol) in THF (2.00 mL) and DMF (0.5 mL) was added NaH (20.11 mg, 503 umol, 60% purity). The mixture was stirred at rt overnight. Methanol was added the mixture, which was subsequently concentrated in vacuo. The residue was purified by HPLC to provide the title compound (8 mg, 5% yield) as the trifluoroacetic acid salt. LCMS (ESI): [M+H] 395. $^1$H NMR (400 MHz, METHANOL-$d_4$) δ8.53 (s, 2H), 7.39 (s, 1H), 4.26-4.42 (m, 2H), 4.15 (s, 2H), 3.51-3.65 (m, 3H), 3.38-3.48 (m, 1H), 3.15-3.27 (m, 3H), 2.96-3.06 (m, 4H), 2.73-2.84 (m, 1H), 2.21 (s, 3H).

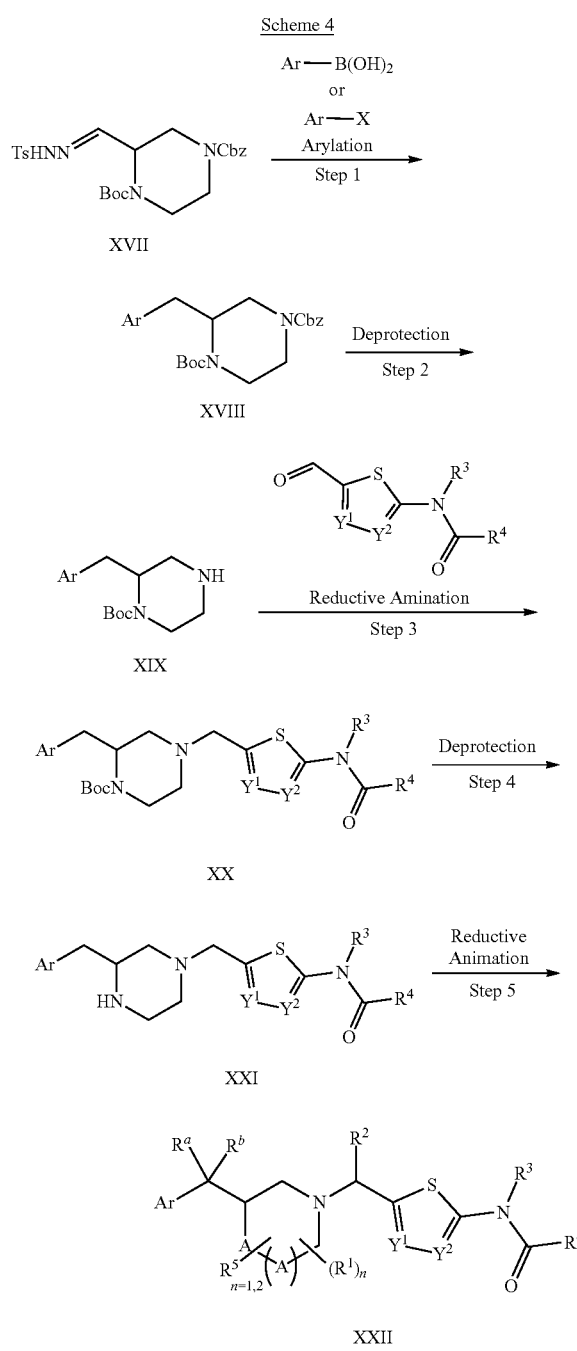

Intermediate 38

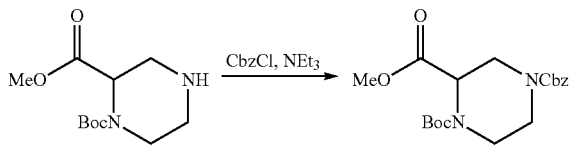 [SMILES: COC(=O)C1CNCCN1C(=O)OC(C)(C)C ; COC(=O)C1CN(C(=O)OCc2ccccc2)CCN1C(=O)OC(C)(C)C]

4-benzyl 1-(tert-butyl) 2-methyl piperazine-1,2,4-tricarboxylate: To a solution of 1-(tert-butyl) 2-methyl piperazine-1,2-dicarboxylate (10.0 g, 40.9 mmol) and Et$_3$N (4.56 g, 45.0 mmol) in DCM (100.0 mL) was added Cbz-Cl (7.68 g, 45.0 mmol) dropwise at 0° C. under N$_2$. Upon the addition, the solution became cloudy and the mixture was stirred at 0° C. for 30 minutes. The reaction was warmed up to 30° C. for 10 hours. The reaction was quenched with aqueous NH$_4$Cl (20 mL) and extracted with EtOAc (3×60 mL). The combined organics were washed with brine (2×50 mL) and dried over Na$_2$SO$_4$. Then the mixture was concentrated under reduced pressure and purified by column chromatography (Petroleum ether/EtOAc=5/1) on silica gel to provide the title compound (10.5 g, 67.79% yield). $^1$H NMR (500 MHz, CDCl$_3$) δ7.31-7.36 (m, 5H), 5.07-5.17 (m, 2H), 4.56-4.76 (m, 3H), 3.59-3.87 (m, 4H), 3.28-2.90 (m, 3H), 1.47 (s, 9H).

Intermediate 39

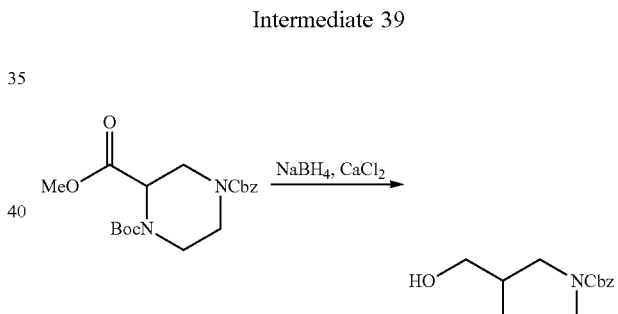

4-benzyl 1-(tert-butyl) 2-(hydroxymethyl)piperazine-1,4-dicarboxylate: To a solution of 4-benzyl 1-(tert-butyl) 2-methyl piperazine-1,2,4-tricarboxylate (7.0 g, 18.5 mmol) in THF (30.0 mL) and EtOH (30.0 mL) was added CaCl$_2$ (3.29 g, 29.6 mmol), which was stirred at 30° C. until the salt was dissolved. The resulting mixture was cooled down to 0° C. and NaBH$_4$ (3.5 g, 92.5 mmol) was added. The reaction was stirred at 0° C. for 30 minutes then was warmed up to 30° C. and stirred for 4 hours. The reaction was quenched with HCl (2 M, 10 mL) and stirred until the effervescence ceased. Then the mixture was extracted with EtOAc (3×50 mL). The combined organic was washed with brine (2×30 mL) and dried over Na$_2$SO$_4$, concentrated under reduced pressure and purified by column chromatography (Petroleum ether/EtOAc=1/1) on silica gel to provide the title compound (5.12 g, 79% yield). $^1$H NMR (400 MHz, CDCl$_3$) δ7.29-7.39 (m, 5H), 5.16 (s, 2H), 3.85-4.19 (m, 4H), 3.59 (br s, 2H), 3.00 (br s, 3H), 1.46 (s, 9H).

Intermediate 40

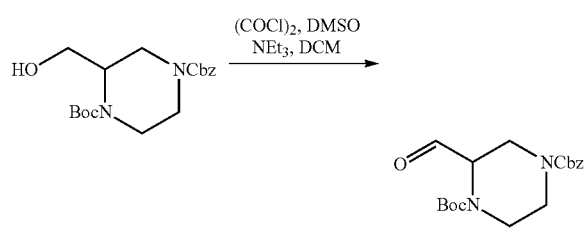

4-benzyl 1-(tert-butyl) 2-formylpiperazine-1,4-dicarboxylate: To a solution of (COCl)$_2$ (17.39 g, 137.00 mmol) in DCM (120 mL) was added DMSO (16.06 g, 205.5 mmol) dropwise at −70° C. and stirred for 30 min. A solution of 4-benzyl 1-(tert-butyl) 2-(hydroxymethyl)piperazine-1,4-dicarboxylate (12.0 g, 34.25 mmol) in DCM (100 mL) was added dropwise and the mixture was stirred at −70° C. for 1 h. Et$_3$N (27.7 g, 274.0 mmol) was added dropwise at −70° C. and the mixture was stirred at −70° C. for 1 h then warmed to 0° C. and stirred for another hour 1 h. The reaction was quenched by water (200 mL) slowly, extracted with DCM (2×200 mL). The combined organic phases were washed with brine (200 mL), dried over anhydrous Na$_2$SO$_4$, filtered and concentrated. The residue was purified by silica gel column (Petroleum ether/EtOAc=10/1 to 5/1) to afford the title compound (8.20 g, 68% yield). $^1$HNMR (400 MHz, CDCl$_3$) δ9.57 (brs, 1H), 7.32-7.36 (m, 5H), 5.12 (s, 2H), 4.48-4.64 (m, 2H), 3.94-4.09 (m, 2H), 2.98-3.21 (m, 3H), 1.47 (s, 9H).

Intermediate 41

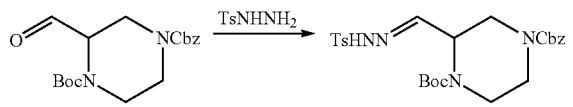

4-Benzyl 1-(tert-butyl) 2-((2-tosylhydrazineylidene)methyl)piperazine-1,4-dicarboxylate: To a solution of 4-benzyl 1-(tert-butyl) 2-formylpiperazine-1,4-dicarboxylate (8.20 g, 23.54 mmol) in MeOH (150 mL) was added TsNHNH$_2$ (4.34 g, 23.54 mmol). The mixture was stirred at 25° C. for 16 h. The solvent was removed and the residue was purified by silica gel column (Petroleum ether/EtOAc=10:1 to 5:1 then 3:1) to afford the title compound (11.50 g, 95% yield). LCMS (ESI): [M+H (-Boc)] 417.

Intermediate 42

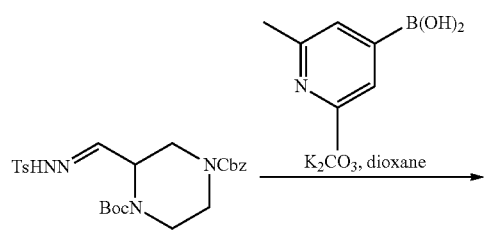

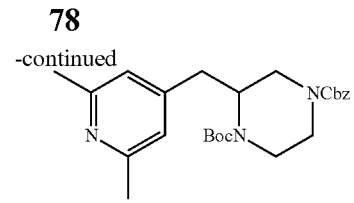

4-Benzyl 1-(tert-butyl) 2-((2,6-dimethylpyridin-4-yl)methyl)piperazine-1,4-dicarboxylate: To a solution of 4-benzyl 1-(tert-butyl) 2-((2-tosylhydrazineylidene)methyl)piperazine-1,4-dicarboxylate (1.00 g, 1.94 mmol) in dioxane (10.0 mL) were added (2,6-dimethylpyridin-4-yl)boronic acid (292.23 mg, 1.94 mmol) and K$_2$CO$_3$ (802.60 mg, 5.81 mmol). The mixture was stirred at 110° C. for 5 h. The solvent was removed and the residue was treated with water (20 mL), extracted with EtOAc (2×20 mL). The combined organic phases were washed with brine (20 mL), dried over anhydrous Na$_2$SO$_4$, filtered and concentrated. The residue was purified by silica gel column (Petroleum ether/EtOAc=3/1 to 1/1) to afford the title compound (500.0 mg, 59% yield). $^1$HNMR (500 MHz, CDCl$_3$) δ7.34-7.36 (m, 5H), 6.75-6.80 (m, 2H), 5.18 (s, 2H), 3.93-4.20 (m, 4H), 2.95-3.15 (m, 3H), 2.43-2.48 (m, 2H), 2.27-2.38 (m, 6H), 1.46 (s, 9H).

Intermediate 43

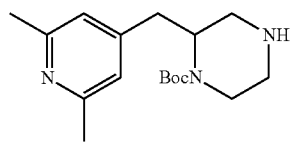 [SMILES: Cc1cc(CC2CNCCN2C(=O)OC(C)(C)C)cc(C)n1]

tert-butyl 2-((2,6-dimethylpyridin-4-yl)methyl)piperazine-1-carboxylate: The title compound was prepared in an analogous manner to intermediate 25.

Intermediate 44

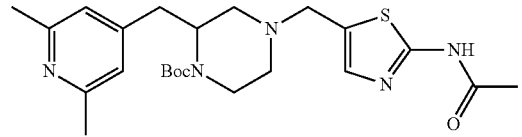 [SMILES: CC(=O)Nc1ncc(CN2CCN(C(=O)OC(C)(C)C)C(Cc3cc(C)nc(C)c3)C2)s1]

tert-butyl 4-((2-acetamidothiazol-5-yl)methyl)-2-((2,6-dimethylpyridin-4-yl)methyl)piperazine-1-carboxylate: The title compound was prepared in an analogous manner to intermediate 26. The resulting enantiomers were separated using chiral SFC.

Intermediate 45

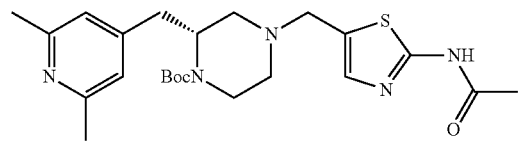

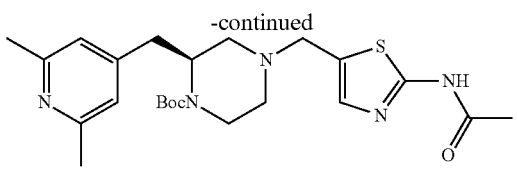

The mixture of enantiomers of Intermediate 44, namely tert-butyl (R)-4-((2-acetamidothiazol-5-yl)methyl)-2-((2,6-dimethylpyridin-4-yl)methyl)piperazine-1-carboxylate and tert-butyl (S)-4-((2-acetamidothiazol-5-yl)methyl)-2-((2,6-dimethylpyridin-4-yl)methyl)piperazine-1-carboxylate, was separated using SFC (Column: REGIS (s,s) WHELK-O1 (250 mm×30 mm, 5 um); Condition: 0.1% $NH_3H_2O$ EtOH) to afford the title compound (100.0 mg, 31 yield, Rt=4.56 min), as Peak 1 and Peak 2.

Example 4-1

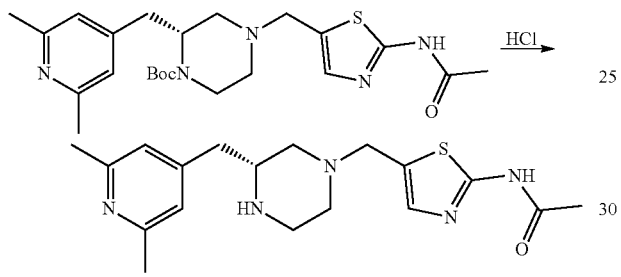

(R)—N-(5-((3-((2,6-dimethylpyridin-4-yl)methyl)piperazin-1-yl)methyl)thiazol-2-yl)acetamide hydrochloride: A solution of HCl in dioxane (0.217 mmol, 1.00 mL) was added to tert-butyl (R)-4-((2-acetamidothiazol-5-yl)methyl)-2-((2,6-dimethylpyridin-4-yl)methyl)piperazine-1-carboxylate; intermediate 45 (100.0 mg, 0.217 mmol) and the mixture was stirred at 25° C. for 2 h. The mixture was concentrated and the residue was treated with water (5 mL) and lyophilized to afford the title compound (80.0 mg, Hydrochloride). LCMS (ESI): [M+H] 360. $^1$HNMR: (500 MHz, MeOD) δ7.76 (s, 2H), 7.70 (s, 1H), 4.57 (s, 2H), 4.20-4.22 (m, 1H), 3.62-3.71 (m, 3H), 3.50-3.55 (m, 1H), 3.33-3.41 (m, 4H), 2.76 (s, 6H), 2.25 (s, 3H).

Example 4-2

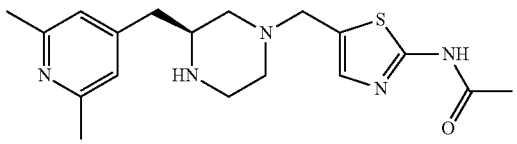 [SMILES: CC(=O)Nc1ncc(CN2CCN[C@@H](Cc3cc(C)nc(C)c3)C2)s1]

(S)—N-(5-((3-((2,6-dimethylpyridin-4-yl)methyl)piperazin-1-yl)methyl)thiazol-2-yl)acetamide hydrochloride: The title compound was prepared in an analogous manner to example 4-1 from tert-butyl (S)-4-((2-acetamidothiazol-5-yl)methyl)-2-((2,6-dimethylpyridin-4-yl)methyl)piperazine-1-carboxylate; intermediate 46 LCMS (ESI): [M+H] 360. $^1$HNMR: (500 MHz, MeOD) δ7.76 (s, 2H), 7.71 (s, 1H), 4.58 (s, 2H), 4.20-4.23 (m, 1H), 3.64-3.72 (m, 3H), 3.50-3.56 (m, 1H), 3.35-3.41 (m, 4H), 2.76 (s, 6H), 2.26 (s, 3H).

Example 4-3

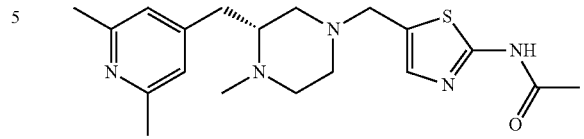

(R)—N-(5-((3-((2,6-dimethylpyridin-4-yl)methyl)-4-methylpiperazin-1-yl)methyl)thiazol-2-yl)acetamide: The title compound was prepared in an analogous manner to example 2-2 from (R)—N-(5-((3-((2,6-dimethylpyridin-4-yl)methyl)piperazin-1-yl)methyl)thiazol-2-yl)acetamide hydrochloride; example 4-1 LCMS (ESI): [M+H] 374. $^1$HNMR: (500 MHz, CDCl$_3$) δ12.01 (s, 1H), 7.14 (s, 1H), 6.76 (s, 2H), 3.48-3.64 (m, 2H), 2.93-2.96 (m, 1H), 2.77-2.79 (m, 1H), 2.63-2.66 (m, 1H), 2.33-2.53 (m, 14H), 2.29 (s, 3H), 2.08-2.01 (m, 1H).

Example 4-4

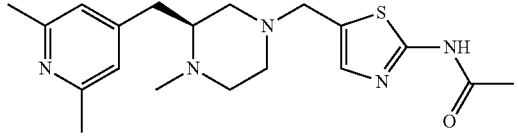 [SMILES: CC(=O)Nc1ncc(CN2CCN(C)[C@@H](Cc3cc(C)nc(C)c3)C2)s1]

(S)—N-(5-((3-((2,6-dimethylpyridin-4-yl)methyl)-4-methylpiperazin-1-yl)methyl)thiazol-2-yl)acetamide: The title compound was prepared in an analogous manner to example 2-2 from (S)—N-(5-((3-((2,6-dimethylpyridin-4-yl)methyl)piperazin-1-yl)methyl)thiazol-2-yl)acetamide hydrochloride; example 4-2 LCMS (ESI): [M+H] 374. $^1$HNMR: (500 MHz, CDCl$_3$) δ12.23 (s, 1H), 7.13 (s, 1H), 6.75 (s, 2H), 3.48-3.64 (m, 2H), 2.93-2.95 (m, 1H), 2.76-2.79 (m, 1H), 2.63-2.66 (m, 1H), 2.32-2.53 (m, 14H), 2.28 (s, 3H), 2.01-2.08 (m, 1H).

Intermediate 47

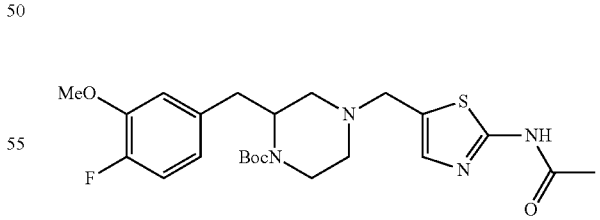

tert-butyl 4-((2-acetamidothiazol-5-yl)methyl)-2-(4-fluoro-3-methoxybenzyl)piperazine-1-carboxylate: The title compound was prepared in an analogous manner to intermediate 26 from 4-benzyl 1-(tert-butyl) 2-((2-tosylhydrazineylidene)methyl)piperazine-1,4-dicarboxylate, (4-fluoro-3-methoxyphenyl)boronic acid, and N-(5-formylthiazol-2-yl)acetamide. LCMS (ESI): [M+H] 479.

Example 4-5

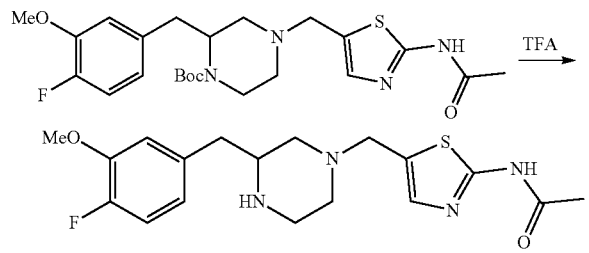

N-(5-((3-(4-fluoro-3-methoxybenzyl)piperazin-1-yl)methyl)thiazol-2-yl)acetamide: To a solution of tert-butyl 4-((2-acetamidothiazol-5-yl)methyl)-2-(4-fluoro-3-methoxybenzyl)piperazine-1-carboxylate (80.0 mg, 0.167 mmol) in DCM (5.0 mL) was added TFA (2.98 g, 2.0 mL). The reaction mixture was stirred at 28° C. for 1 hour. The mixture was adjusted to pH 8 with $NH_3H_2O$. Water (5 mL) was added and extracted with DCM (10 mL×2). The combined organic phase was dried over $Na_2SO_4$, filtered and concentrated. The resulting enantiomers were separated by SFC (Column: Chiralpak AD-3 150× 4.6 mm I.D., 3 um Mobile phase: A: CO2 B:ethanol (0.05% DEA)) to provide Example 4-6.

Example 4-6

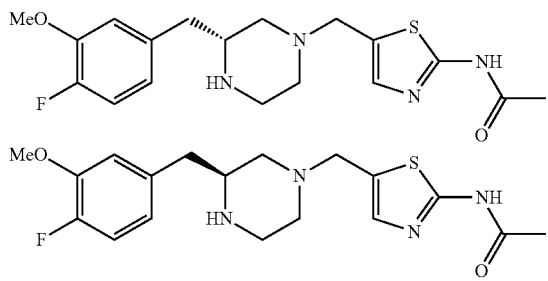

The mixture of enantiomers of Example 4-5, namely (R)—N-(5-((3-(4-fluoro-3-methoxybenzyl)piperazin-1-yl)methyl)thiazol-2-yl)acetamide and (S)—N-(5-((3-(4-fluoro-3-methoxybenzyl)piperazin-1-yl)methyl)thiazol-2-yl)acetamide, was separated as:

Peak 1: LCMS (ESI): [M+H] 379. $^1$HNMR: (500 MHz, Methanol-d4) δ7.20 (s, 1H), 6.96-6.98 (m, 1H), 6.88-6.90 (m, 1H), 6.70-6.71 (m, 1H), 3.83 (s, 3H), 3.77 (s, 2H), 2.92-2.96 (m, 2H), 2.76-2.79 (m, 3H), 2.61-2.65 (m, 2H), 2.18 (s, 3H), 2.17-2.18 (m, 1H), 1.82-1.87 (m, 1H).

Peak 2: LCMS (ESI): [M+H] 379. $^1$HNMR: (500 MHz, Methanol-d4) δ7.22 (s, 1H), 6.91-6.99 (m, 2H), 6.72-6.75 (m, 1H), 3.88 (s, 3H), 3.71 (s, 2H), 3.10-3.13 (m, 2H), 2.83-2.96 (m, 3H), 2.72-2.74 (m, 2H), 2.25-2.35 (m, 1H), 2.19 (s, 3H), 1.98-2.03 (m, 1H).

Example 4-7

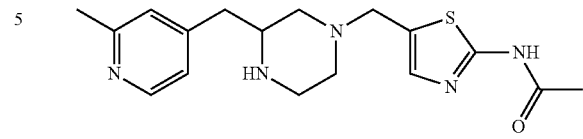

The title compound was prepared in an analogous manner to example 4-6 from 4-benzyl 1-(tert-butyl) 2-((2-tosylhydrazineylidene)methyl)piperazine-1,4-dicarboxylate, (2-methylpyridin-4-yl)boronic acid, and N-(5-formylthiazol-2-yl)acetamide.

Example 4-8

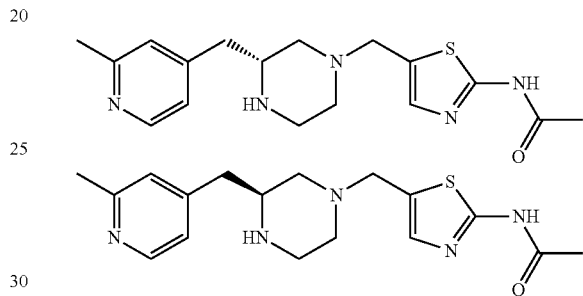

The resulting mixture of enantiomers of Example 4-7, namely (R)—N-(5-((3-((2-methylpyridin-4-yl)methyl)piperazin-1-yl)methyl)thiazol-2-yl)acetamide and (S)—N-(5-((3-((2-methylpyridin-4-yl)methyl)piperazin-1-yl)methyl)thiazol-2-yl)acetamide, was separated by SFC (Column: DAICEL CHIRALPAK AD-H (250 mm×30 mm, 5 um), Condition: 0.1% $NH_3H_2O$ EtOH, Flow Rate (ml/min): 50), as:

Peak 1: LCMS (ESI): [M+H] 346. $^1$HNMR: (500 MHz, CDCl$_3$) δ 10.61 (br s, 1H), 8.39 (d, J=5.0 Hz, 1H), 7.18 (s, 1H), 7.00 (s, 1H), 6.94 (d, J=5.0 Hz, 1H), 3.66 (s, 2H), 2.96-3.05 (m, 1H), 2.83-2.85 (m, 1H), 2.78-2.81 (m, 3H), 3.66-2.67 (m, 2H), 2.65 (s, 3H), 2.52 (s, 3H), 2.18-2.29 (m, 1H), 1.96-1.98 (m, 1H).

Peak 2: LCMS (ESI): [M+H] 346. $^1$HNMR: (500 MHz, CDCl$_3$) δ 10.95 (s, 1H), 8.38 (d, J=5.0 Hz, 1H), 7.18 (s, 1H), 7.00 (s, 1H), 6.94 (d, J=5.0 Hz, 1H), 3.66 (s, 2H), 2.96-3.05 (m, 1H), 2.83-2.85 (m, 1H), 2.78-2.81 (m, 3H), 3.66-2.67 (m, 2H), 2.65 (s, 3H), 2.52 (s, 3H), 2.18-2.29 (m, 1H), 1.95-1.98 (m, 1H).

Example 4-9

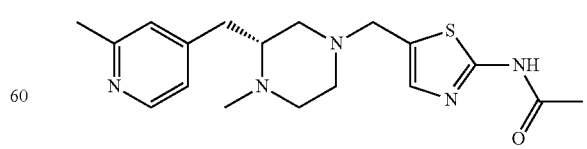

(R)—N-(5-(((4-methyl-3-((2-methylpyridin-4-yl)methyl)piperazin-1-yl)methyl)thiazol-2-yl)acetamide: The title compound was prepared in an analogous manner to example 2-2 from (R)—N-(5-((3-((2-methylpyridin-4-yl)methyl)piperazin-1-yl)methyl)thiazol-2-yl)acetamide; example 4-8. LCMS (ESI): [M+H] 360. ¹HNMR: (400 MHz, Methanol-d4) δ8.21 (d, J=5.2 Hz, 1H), 7.15 (s, 1H), 7.10 (s, 1H), 7.04 (d, J=4.8 Hz, 1H), 3.59-3.64 (m, 2H), 3.08-3.11 (m, 1H), 2.85-2.86 (m, 1H), 2.83-2.84 (m, 1H), 2.68-2.69 (m, 2H), 2.44-2.55 (m, 9H), 2.42 (s, 3H), 1.99-2.19 (m, 1H).

Example 4-10

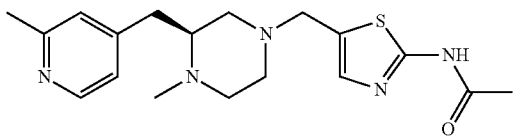 [SMILES: CC(=O)Nc1ncc(CN2CCN(C)[C@@H](Cc3ccnc(C)c3)C2)s1]

(S)—N-(5-((4-methyl-3-((2-methylpyridin-4-yl)methyl)piperazin-1-yl)methyl)thiazol-2-yl)acetamide: The title compound was prepared in an analogous manner to example 2-2 from (S)—N-(5-((3-((2-methylpyridin-4-yl)methyl)piperazin-1-yl)methyl)thiazol-2-yl)acetamide; example 4-9. LCMS (ESI): [M+H] 360. ¹HNMR: (400 MHz, Methanol-d4) δ8.21 (d, J=5.6 Hz, 1H), 7.15 (s, 1H), 7.12 (s, 1H), 7.04 (d, J=4.8 Hz, 1H), 3.55-3.64 (m, 2H), 3.09-3.12 (m, 1H), 2.85-2.86 (m, 1H), 2.83-2.84 (m, 1H), 2.68-2.69 (m, 2H), 2.44-2.54 (m, 9H), 2.42 (s, 3H), 1.99-2.19 (m, 1H).

Example 4-11

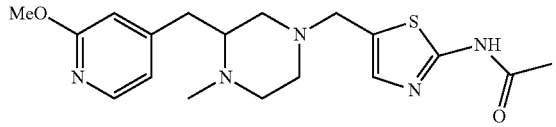 [SMILES: COc1cc(CC2CN(Cc3cnc(NC(C)=O)s3)CCN2C)ccn1]

N-(5-((3-((2-methoxypyridin-4-yl)methyl)-4-methylpiperazin-1-yl)methyl)thiazol-2-yl)acetamide: The title compound was prepared in an analogous manner to example 4-10 from 4-benzyl 1-(tert-butyl) 2-((2-tosylhydraziney-lidene)methyl)piperazine-1,4-dicarboxylate, (2-methoxy-pyridin-4-yl)boronic acid, and N-(5-formylthiazol-2-yl)acetamide.

Example 4-12

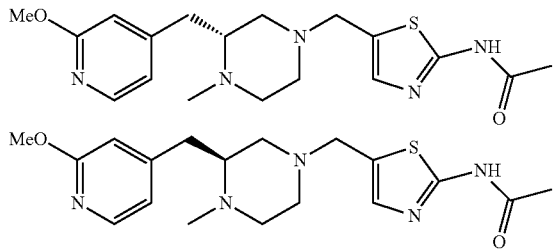

The resulting mixture of enantiomers from Example 4-12, namely (R)—N-(5-((3-((2-methoxypyridin-4-yl)methyl)-4-methylpiperazin-1-yl)methyl)thiazol-2-yl)acetamide and (S)—N-(5-((3-((2-methoxypyridin-4-yl)methyl)-4-methylpiperazin-1-yl)methyl)thiazol-2-yl)acetamide, was separated by (column: DAICEL CHIRALPAK IC (250 mm×30 mm, 10 um), condition: 0.1% NH₃H₂O EtOH) as:

Peak 1: LCMS (ESI): [M+H] 376. ¹HNMR: (500 MHz, Methanol-d4) δ8.94 (d, J=5.2 Hz, 1H), 7.15 (s, 1H), 6.78 (d, J=4.8 Hz, 1H), 6.61 (s, 1H), 3.85 (s, 3H), 3.55-3.66 (s, 2H), 3.06-3.08 (m, 1H), 2.84-2.85 (m, 1H), 2.81-2.83 (m, 1H), 2.40-2.60 (m, 8H), 2.19 (s, 3H), 1.99-2.02 (m, 1H).

Peak 2: LCMS (ESI): [M+H] 376. ¹HNMR: (500 MHz, Methanol-d4) δ7.95 (d, J=5.6 Hz, 1H), 7.15 (s, 1H), 6.80 (d, J=5.2 Hz, 1H), 6.61 (s, 1H), 3.85 (s, 3H), 3.56-3.69 (m, 2H), 3.07-3.09 (m, 1H), 2.85-2.89 (m, 1H), 2.69-2.72 (m, 1H), 2.44-2.60 (m, 8H), 2.19 (s, 3H), 1.99-2.02 (m, 1H).

Example 4-13

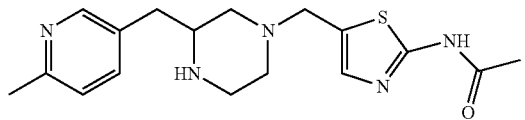 [SMILES: CC(=O)Nc1ncc(CN2CCNC(Cc3ccc(C)nc3)C2)s1]

N-(5-((3-((6-methylpyridin-3-yl)methyl)piperazin-1-yl)methyl)thiazol-2-yl)acetamide: The title compound was prepared in an analogous manner to example 4-6 from 4-benzyl 1-(tert-butyl) 2-((2-tosylhydrazineylidene)methyl)piperazine-1,4-dicarboxylate, (2-methylpyridin-4-yl)boronic acid, and N-(5-formylthiazol-2-yl)acetamide.

Example 4-14

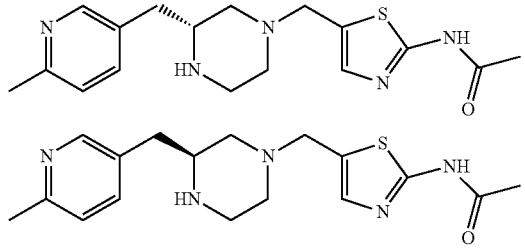

The resulting mixture of enantiomers from Example 4-14, namely (R)—N-(5-((3-((6-methylpyridin-3-yl)methyl)piperazin-1-yl)methyl)thiazol-2-yl)acetamide and (S)—N-(5-((3-((6-methylpyridin-3-yl)methyl)piperazin-1-yl)methyl)thiazol-2-yl)acetamide, was separated by SFC (DAICEL CHIRALPAK AD-H (250 mm×30 mm, 5 um); Begin B: 45%; End B: 45%; FlowRate (ml/min): 50) as:

Peak 1: LCMS (ESI): [M+H] 346. ¹HNMR: (500 MHz, Methanol-d4) δ8.80 (s, 1H), 8.51-8.52 (m, 1H), 7.96 (d, J=8.5 Hz, 1H), 7.60 (s, 1H), 4.38 (s, 2H), 4.05-4.06 (m, 1H), 3.31-3.65 (m, 6H), 3.16-3.17 (m, 2H), 2.81 (s, 3H), 2.25 (s, 3H).

Peak 2: LCMS (ESI): [M+H] 346. ¹HNMR: (500 MHz, Methanol-d4) δ8.83 (s, 1H), 8.55 (d, J=8.5 Hz, 1H), 7.96 (d, J=8.5 Hz, 1H), 7.73 (s, 1H), 4.61 (s, 2H), 4.19-4.18 (m, 1H), 3.66-3.69 (m, 3H), 3.38-3.52 (m, 5H), 2.81 (s, 3H), 2.26 (s, 3H).

Example 4-15

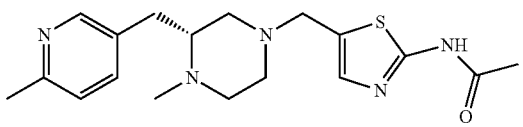 [SMILES: CC(=O)Nc1ncc(CN2CCN(C)[C@H](Cc3ccc(C)nc3)C2)s1]

(R)—N-(5-((4-methyl-3-((6-methylpyridin-3-yl)methyl)piperazin-1-yl)methyl)thiazol-2-yl)acetamide: The title compound was prepared in an analogous manner to example 2-2 from (R)—N-(5-((3-((6-methylpyridin-3-yl)methyl)piperazin-1-yl)methyl)thiazol-2-yl)acetamide; example 4-14. LCMS (ESI): [M+H] 360. $^1$HNMR: (400 MHz, Methanol-d4) δ8.21 (s, 1H), 7.55 (dd, J=8.0, 2.0 Hz, 1H), 7.20 (d, J=8.0 Hz, 1H), 7.16 (s, 1H), 3.60 (s, 2H), 3.10-3.13 (m, 1H), 2.86 (d, J=11.6 Hz, 1H), 2.72 (d, J=9.2 Hz, 1H), 2.34-2.50 (m, 11H), 2.19 (s, 3H), 1.94-1.97 (m, 1H).

Example 4-16

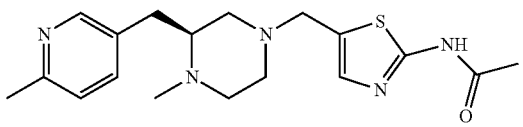 [SMILES: CC(=O)Nc1ncc(CN2CCN(C)[C@@H](Cc3ccc(C)nc3)C2)s1]

(S)—N-(5-((4-methyl-3-((6-methylpyridin-3-yl)methyl)piperazin-1-yl)methyl)thiazol-2-yl)acetamide: The title compound was prepared in an analogous manner to example 2-2 from (S)—N-(5-((3-((6-methylpyridin-3-yl)methyl)piperazin-1-yl)methyl)thiazol-2-yl)acetamide; example 4-15. LCMS (ESI): [M+H] 360. $^1$HNMR: (400 MHz, Methanol-d4) δ8.21 (s, 1H), 7.54-7.57 (m, 1H), 7.16-7.21 (m, 2H), 3.60 (s, 2H), 3.12 (d, J=11.6 Hz, 1H), 2.85-2.88 (m, 1H), 2.72 (d, J=9.6 Hz, 1H), 2.34-2.54 (m, 11H), 2.19 (s, 3H), 1.98-1.97 (m, 1H).

Intermediate 48

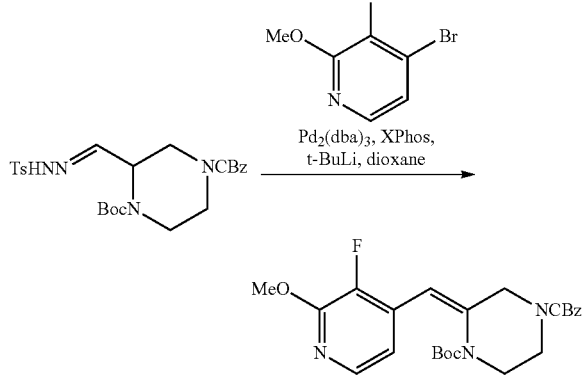

4-benzyl 1-(tert-butyl) (Z)-2-((3-fluoro-2-methoxypyridin-4-yl)methylene)piperazine-1,4-dicarboxylate: To a solution of 4-benzyl 1-(tert-butyl) (Z)-2-((2-tosylhydraziney-lidene)methyl)piperazine-1,4-dicarboxylate (1.0 g, 1.94 mmol) and 4-bromo-3-fluoro-2-methoxypyridine (0.599 g, 2.91 mmol) in dioxane (10.0 mL) were added Pd$_2$(dba)$_3$ (0.177 g, 0.194 mmol), XPhos (0.092 g, 0.194 mmol) and lithium 2-methylpropan-2-olate (0.465 g, 5.82 mmol). The mixture was stirred at 80° C. for 2 hours under N$_2$. The reaction was concentrated and was purified by column chromatography (Petroleum ether/EtOAc=5/1) on silica gel to provide the title compound (118 mg, 13% yield). LCMS (ESI): [M+H] 458.

Intermediate 49

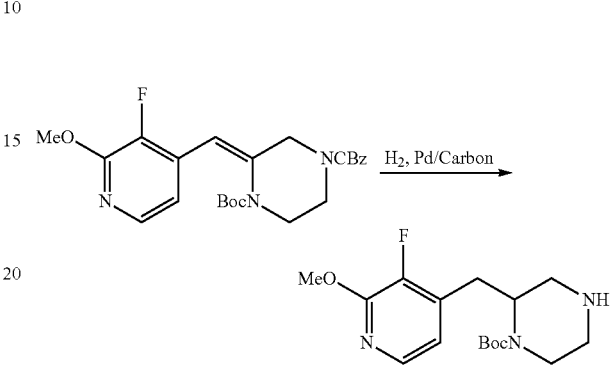

tert-butyl 2-((3-fluoro-2-methoxypyridin-4-yl)methyl)piperazine-1-carboxylate: To a solution of 4-benzyl 1-(tert-butyl) (Z)-2-((3-fluoro-2-methoxypyridin-4-yl)methylene)piperazine-1,4-dicarboxylate (94 mg, 0.205 mmol) in MeOH (5.0 mL) was added Pd(OH)$_2$/C (29 mg, 0.021 mmol, 10% purity) under N$_2$ atmosphere. The suspension was degassed and purged with H$_2$ for three times. The mixture was stirred under H$_2$ (40 Psi) at 30° C. for 2 hours. The mixture was filtered, and the eluent was concentrated under reduced pressure to give a residue which was purified by column chromatography (Petroleum ether/EtOAc=1/2) on silica gel to provide the title compound (32.0 mg, 48% yield). LCMS (ESI): [M+H] 326.

Example 4-17

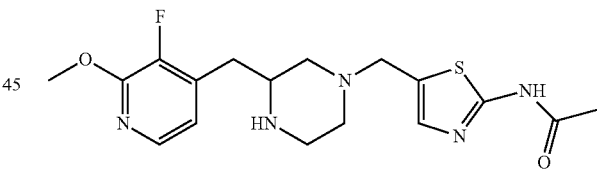

N-(5-((3-((3-fluoro-2-methoxypyridin-4-yl)methyl)piperazin-1-yl)methyl)thiazol-2-yl)acetamide: The title compound was prepared in an analogous manner to example 2-22 from tert-butyl 2-((3-fluoro-2-methoxypyridin-4-yl)methyl)piperazine-1-carboxylate (intermediate X; above) and N-(5-formylthiazol-2-yl)acetamide.

Example 4-18

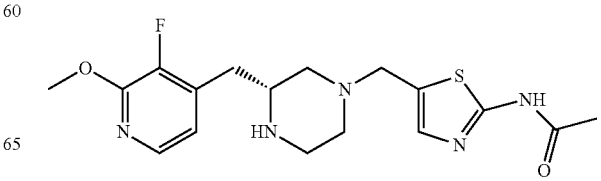

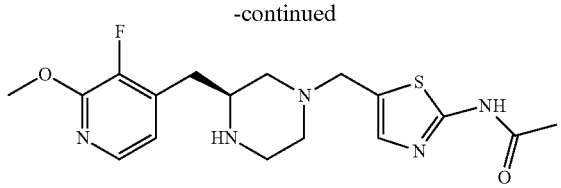

The resulting mixture of enantiomers from Example 4-18, namely (R)—N-(5-((3-((3-fluoro-2-methoxypyridin-4-yl)methyl)piperazin-1-yl)methyl)thiazol-2-yl)acetamide and (S)—N-(5-((3-((3-fluoro-2-methoxypyridin-4-yl)methyl)piperazin-1-yl)methyl)thiazol-2-yl)acetamide, was separated by SFC separated by SFC (Instrument: SFC-14; Condition: 0.1% $NH_3H_2O$ IPA); Column: DAICEL CHIRALPAK AD-H (250 mm*30 mm, 5 um); Begin B: 35%; End B: 35%; FlowRate (ml/min): 50) as:

Peak 1: LCMS (ESI): [M+H] 380. $^1$HNMR: (400 MHz, Methanol-d4) δ7.80 (d, J=5.2 Hz, 1H), 7.22 (s, 1H), 6.83 (t, J=4.8 Hz, 1H), 3.96 (s, 3H), 3.69-3.72 (m, 2H), 3.04-3.08 (m, 1H), 2.95-2.98 (m, 1H), 2.75-2.84 (m, 5H), 2.20 (s, 3H), 2.14-2.19 (m, 1H), 1.91-1.96 (m, 1H).

Peak 2: LCMS (ESI): [M+H] 380. $^1$HNMR: (400 MHz, Methanol-d4) δ7.86 (d, J=4.8 Hz, 1H), 7.24 (s, 1H), 6.86 (t, J=4.8 Hz, 1H), 3.98 (s, 3H), 3.73-3.81 (m, 2H), 3.46-3.47 (m, 1H), 3.25-3.26 (m, 1H), 3.07-3.10 (m, 1H), 2.93-2.97 (m, 4H), 2.24-2.38 (m, 1H), 2.21-2.23 (m, 1H), 2.20 (s, 3H).

Biological Data

OGA Enzyme Inhibition Biochemical Assay

Recombinant full length human OGA enzyme was purchased from Origene. 4-MUGlcNAc substrate was purchased from Sigma. All other reagents were purchased from Sigma or Fisher. Assay buffer consists of the McIlvaine buffer system, pH 6.4 (0.2M $Na_2HPO_4$ mixed with 0.1M citric acid) and 0.01% BSA. Reactions consist of 1 nM OGA, 100 μM 4-MUGlcNAc ($K_m$), and compound in a final volume of 10 μl. Reactions were incubated for 90 minutes at room temperature and quenched with 40 μl of 3M glycine, pH 10 and read on a Perkin Elmer Envision plate reader (Ex: 355 nm/Em: 460 nm). Compounds were tested with a 10-point dose-response starting from 20 μM with a 4-fold dilution. Data was fit using GraphPad Prism using a 4-paramter fit with variable slope.

| | OGA $IC_{50}$ (nM) |
|---|---|
| Example 1-1 | 16 |
| Example 1-2 | 4400 |
| Example 1-3 | 43 |
| Example 1-4 | 11000 |
| Example 1-5 | 61 |
| Example 1-6 | 100 |
| Example 1-7 | 110 |
| Example 1-8 | 130 |
| Example 1-9 | 1500 |
| Example 1-10 | 160 |
| Example 1-11 | 130 |
| Example 1-12 | 270 |
| Example 1-13 | 260 |
| Example 1-14 | 180 |
| Example 1-15 | 56 |
| Example 1-16 | 160 |
| Example 1-17 | 136 |
| Example 1-18 | 200 |
| Example 1-19 | 110 |
| Example 1-20 | 84 |
| Example 1-21 | 38 |
| Example 1-23 Peak 1 | 19 |
| Example 1-23 Peak 2 | 360 |
| Example 1-25 Peak 1 | 5.3 |
| Example 1-25 Peak 2 | 73 |
| Example 1-25 Peak 3 | 160 |
| Example 1-25 Peak 4 | 1300 |
| Example 1-26 | 5.1 |
| Example 1-27 | 6600 |
| Example 1-28 | 150 |
| Example 1-29 | 12000 |
| Example 1-30 | 17000 |
| Example 1-31 | 9 |
| Example 1-32 | 1.4 |
| Example 1-33 | 31 |
| Example 1-34 | 680 |
| Example 1-35 Peak 1 | 560 |
| Example 1-35 Peak 2 | 20000 |
| Example 1-36 | 57 |
| Example 1-37 Peak 1 | 31 |
| Example 1-37 Peak 2 | 110 |
| Example 1-38 | 45 |
| Example 1-39 Peak 1 | 20 |
| Example 1-39 Peak 2 | 760 |
| Example 1-40 | 99 |
| Example 1-41 Peak 1 | 39 |
| Example 1-41 Peak 2 | 270 |
| Example 1-42 | 19 |
| Example 1-43 Peak 1 | 19 |
| Example 1-43 Peak 2 | 38 |
| Example 1-44 | 32 |
| Example 1-45 Peak 1 | 1600 |
| Example 1-45 Peak 2 | 14 |
| Example 1-46 | 42 |
| Example 1-47 Peak 1 | 1000 |
| Example 1-47 Peak 2 | 17 |
| Example 1-48 | 140 |
| Example 1-49 | 170 |
| Example 2-1 | 7.4 |
| Example 2-2 | 9.8 |
| Example 2-3 | 26 |
| Example 2-4 | 7500 |
| Example 2-5 | 19 |
| Example 2-6 | 17 |
| Example 2-7 | 9600 |
| Example 2-8 | 9.1 |
| Example 2-9 | 45 |
| Example 2-10 | 34 |
| Example 2-11 | 45 |
| Example 2-12 | 180 |
| Example 2-13 | 22 |
| Example 2-14 | 7.5 |
| Example 2-15 | 5900 |
| Example 2-16 | 20000 |
| Example 2-17 | 41 |
| Example 2-18 | 4.9 |

-continued

| | OGA IC$_{50}$ (nM) |
|---|---|
| Example 2-19 | ND |
| Example 2-20 Peak 1 | 560 |
| Example 2-20 Peak 2 | >20000 |
| Example 2-21 | ND |
| Example 2-22 Peak 1 | 18000 |
| Example 2-22 Peak 2 | 850 |
| Example 2-23 | 5600 |
| Example 2-24 | 12000 |
| Example 2-25 | >20000 |
| Example 2-26 | >20000 |
| Example 2-27 | 9900 |
| Example 2-28 | 12000 |
| Example 2-29 | >20000 |
| Example 2-30 | ND |
| Example 3-1 | 21 |
| Example 3-2 | 38 |
| Example 3-3 | 11000 |
| Example 3-4 | 17 |
| Example 3-5 | >20000 |
| Example 4-1 | 7000 |
| Example 4-2 | 350 |
| Example 4-3 | 1600 |
| Example 4-4 | 200 |
| Example 4-5 | ND |
| Example 4-6 Peak 1 | 11000 |
| Example 4-6 Peak 2 | 4100 |
| Example 4-8 Peak 1 | 6700 |
| Example 4-8 Peak 2 | 490 |
| Example 4-9 | >20000 |
| Example 4-10 | 660 |
| Example 4-12 Peak 1 | 950 |
| Example 4-12 Peak 2 | >20000 |
| Example 4-14 Peak 1 | >20000 |
| Example 4-14 Peak 2 | 4400 |
| Example 4-15 | >20000 |
| Example 4-16 | 2000 |
| Example 4-18 Peak 1 | 14000 |
| Example 4-18 Peak 2 | 1500 |

While we have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound represented by the following structural formula:

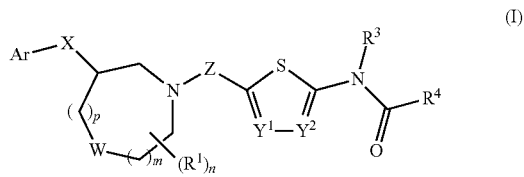

(I)

or a pharmaceutically acceptable salt thereof, wherein:

Ar is an optionally substituted 5- to 10-membered aryl or an optionally substituted 5- to 10-membered heteroaryl, wherein Ar is not a 9-membered bicyclic heteroaryl having 1 to 4 nitrogen atoms when the sum of m and p is 1; wherein said 5- to 10-membered aryl or 5- to 10-membered heteroaryl represented by Ar is optionally substituted with one or more groups selected from $C_1$-$C_4$ alkyl, $C_1$-$C_4$ haloalkyl, $C_3$-$C_6$ cycloalkyl, $C_3$-$C_6$ heterocyclyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, —C(=O)R$^x$, phenyl and monocyclic heteroaryl;

wherein
the $C_1$-$C_4$ alkyl group substituent on Ar is optionally substituted with —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^x$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^y$, $C_3$-$C_6$ cycloalkyl (optionally substituted with one or more groups selected from —CH$_3$, halomethyl, halo, methoxy and halomethoxy), monocyclic heteroaryl (optionally substituted with one or more groups selected from —CH$_3$, halomethyl, halo, methoxy or halomethoxy) and phenyl (optionally substituted with one or more groups selected from —CH$_3$, halomethyl, halo, methoxy and halomethoxy);
the $C_3$-$C_6$ cycloalkyl, $C_3$-$C_6$ heterocyclyl, phenyl and monocyclic heteroaryl group substituent on Ar are optionally and independently substituted with $C_1$-$C_4$ alkyl, $C_1$-$C_4$ haloalkyl, halo, —CN, —NO$_2$, —OR$^z$, —NR$^x$R$^y$, —S(O)$_i$R$^x$, —NR$^x$S(O)$_i$R$^y$, —S(O)$_i$NR$^x$R$^y$, —C(=O)OR$^x$, —OC(=O)OR$^x$, —C(=S)OR$^x$, —O(C=S)R$^y$, —C(=O)NR$^x$R$^y$, —NR$^x$C(=O)R$^y$, —C(=S)NR$^x$R$^y$, —NR$^x$C(=S)R$^y$, —NR$^x$(C=O)OR$^y$, —O(C=O)NR$^x$R$^y$, —NR$^x$(C=S)OR$^y$, —O(C=S)NR$^x$R$^y$, —NR$^x$(C=O)NR$^x$R$^y$, —NR$^x$(C=S)NR$^x$R$^y$, —C(=S)R$^x$, and —C(=O)R$^x$;

each R$^x$ and each R$^y$ is independently —H, $C_1$-$C_4$ alkyl, or $C_3$-$C_8$ cycloalkyl; wherein the $C_1$-$C_4$ alkyl or $C_3$-$C_8$ cycloalkyl represented by R$^x$ or R$^y$ is optionally substituted with one or more substituents selected from halo, hydroxyl, $C_3$-$C_6$ cycloalkyl and phenyl (optionally substituted with one or more groups selected from —CH$_3$, halomethyl, halo, methoxy or halomethoxy);

$R^z$ is —H, $C_1$-$C_4$ alkyl, $C_1$-$C_4$ alkoxy, $C_3$-$C_8$ cycloalkyl, or $C_3$-$C_8$ heterocyclyl; wherein the $C_1$-$C_4$ alkyl or $C_3$-$C_8$ cycloalkyl group represented by $R^z$ is optionally substituted with one or more substituents selected from —CN, halo, hydroxyl, $C_1$-$C_4$ alkyl, $C_1$-$C_4$ alkoxy, $C_3$-$C_6$ cycloalkyl and phenyl (optionally substituted with one or more groups selected from —$CH_3$, halomethyl, halo, methoxy and halomethoxy); and i is 0, 1, or 2;

W is O or —$NR^d$; when W is —$NR^d$, then p is 0 and m is 1;

X is —$CR^2R^2$, —$(CR^2R^2)_2$, —$(CR^2R^2)$O— or —O$(CR^2R^2)$—;

$Y^1$ and $Y^2$ are each $CR^c$ or N, wherein at least one of $Y^1$ or $Y^2$ is N;

Z is —$CR^2R^2$, —C(=O), —$(CR^2R^2)_2$, or —$CH_2C$(=O);

$R^c$ is —H, halo, —$C_1$-$C_4$ alkyl, or —$C_1$-$C_4$ haloalkyl;

$R^d$ is —H, $C_1$-$C_4$ alkyl, $C_1$-$C_4$ haloalkyl, or —C(=O)$C_1$-$C_4$ alkyl;

m is 1 or 2;

p is 0 or 1, provided that the sum of m and p is not 3;

n is 0 or an integer from 1 to 9;

when n is other than 0, $R^1$, for each occurrence, is independently halo, —$C_1$-$C_4$ alkyl, —$C_1$-$C_4$ haloalkyl, or —$C_1$-$C_4$ alkoxy;

$R^2$, for each occurrence, is independently —H, halo, —$C_1$-$C_4$ alkyl, —$C_1$-$C_4$ haloalkyl, —$C_3$-$C_{10}$ cycloalkyl, or —$C_3$-$C_{10}$ halocycloalkyl;

or alternatively two $R^2$ together with the carbon atom to which they are attached form a —$C_3$-$C_{10}$ cycloalkyl;

$R^3$ is —H or —$C_1$-$C_4$ alkyl; and $R^4$ is —H, —$C_1$-$C_4$ alkyl, —$C_1$-$C_4$ haloalkyl, or —$C_3$-$C_6$ cycloalkyl;

or alternatively $R^3$ and $R^4$ taken together with their intervening atoms form an optionally substituted 5- to 7-membered heterocyclyl.

2. The compound according to claim 1, wherein the compound is represented by the following structural formula:

(IIA)

or a pharmaceutically acceptable salt thereof; wherein $R^1$ is halo or —$C_1$-$C_4$ alkyl.

3. The compound according to claim 1, wherein the compound is represented by the following structural formula:

(IIIA)

or a pharmaceutically acceptable salt thereof; wherein $R^2$, for each occurrence, is independently —H or —$C_1$-$C_4$ alkyl.

4. The compound according to claim 1, wherein the compound is represented by the following structural formula:

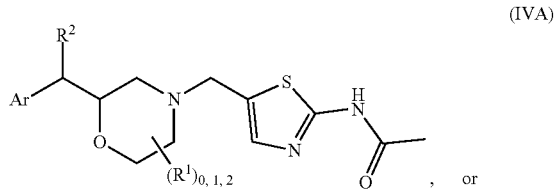

(IVA)

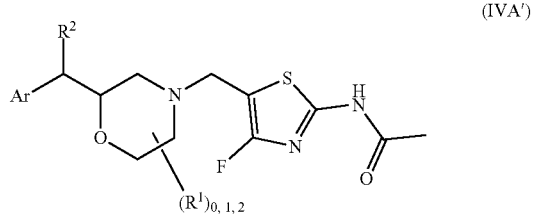

(IVA')

or a pharmaceutically acceptable salt thereof; wherein $R^1$ is —$C_1$-$C_4$ alkyl and wherein $R^2$ is —H, —$CH_3$ or —$CH_2CH_3$.

5. The compound according to claim 1, wherein the compound is represented by a structural formula selected from:

(VA)

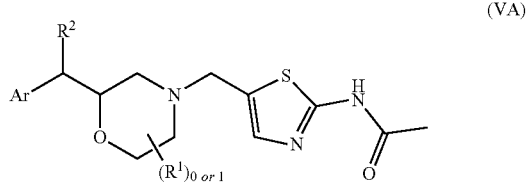

(VA-1)

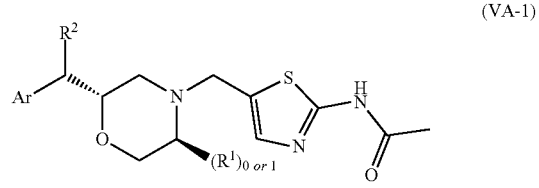

(VA-2)

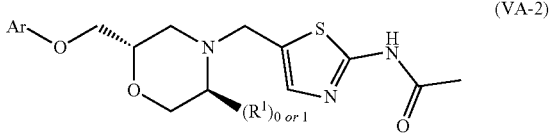

(VA-3)

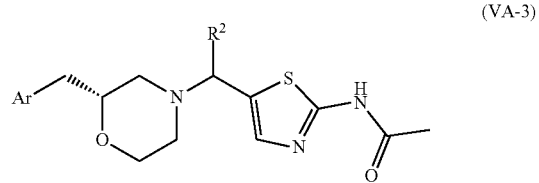

(VA')

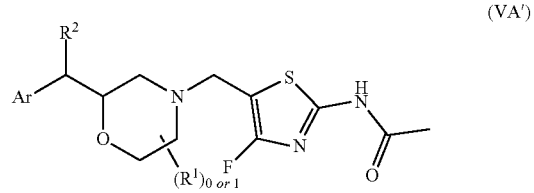

-continued (VA'-1)

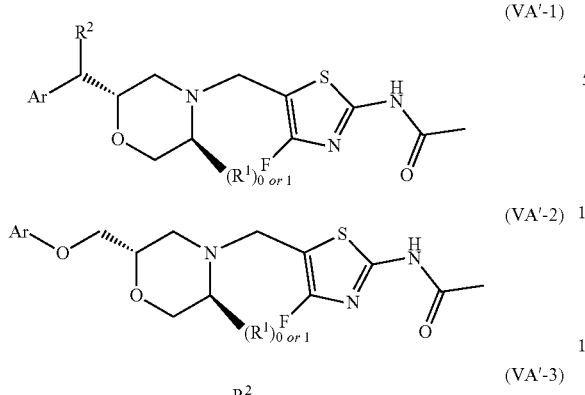

(VA'-2)

(VA'-3)

or a pharmaceutically acceptable salt thereof; wherein R¹ is —CH₃; and R² is —H or —CH₃.

6. The compound according to claim 1, wherein the compound is represented by a structural formula selected from:

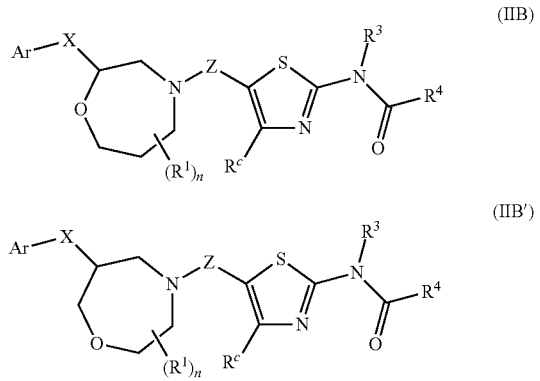

(IIB)

(IIB')

or a pharmaceutically acceptable salt thereof; wherein R¹ is halo or —C₁-C₄ alkyl.

7. The compound according to claim 1, wherein the compound is represented by a structural formula selected from:

(IIIB)

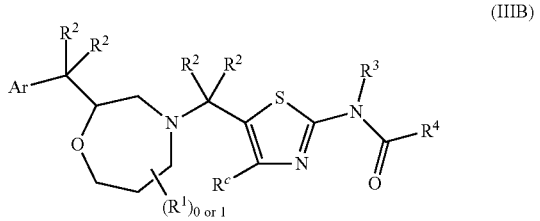

-continued (IIIB')

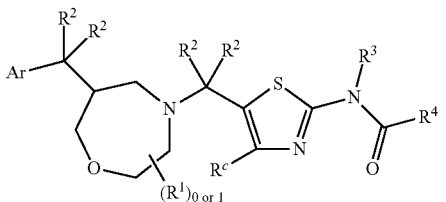

or a pharmaceutically acceptable salt thereof; wherein R², for each occurrence, is independently —H or —C₁-C₄ alkyl.

8. The compound according to claim 1, wherein the compound is represented by a structural formula selected from:

(IVB)

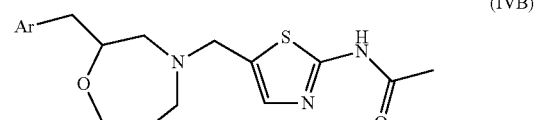

(IVB')

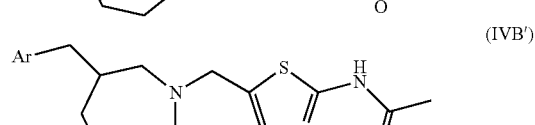

or a pharmaceutically acceptable salt thereof.

9. The compound according to claim 1, wherein the compound is represented by the following structural formula:

(IIC)

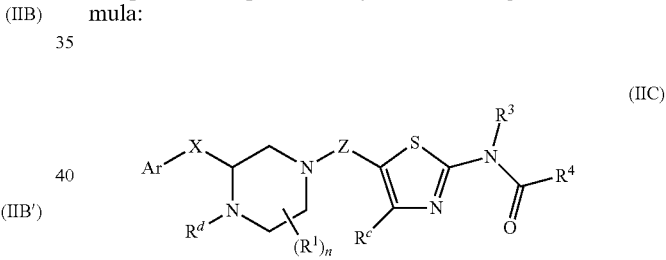

or a pharmaceutically acceptable salt thereof; wherein R¹ is halo or —C₁-C₄ alkyl.

10. The compound according to claim 1, wherein the compound is represented by one of the following structural formulas:

(IIIC-1)

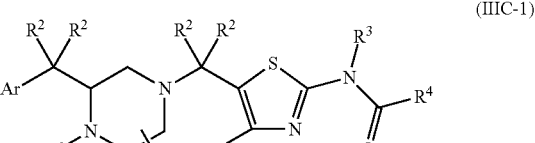

(IIIC-2)

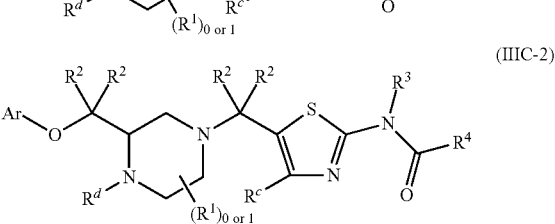

or a pharmaceutically acceptable salt thereof; wherein:

$R^d$ is —H, —$C_1$-$C_4$ alkyl, or —C(=O)$C_1$-$C_4$ alkyl;
$R^1$ is —$C_1$-$C_4$ alkyl;
$R^2$, for each occurrence, is independently —H or $C_1$-$C_4$ alkyl.

11. The compound according to claim 1, wherein the compound is represented by one of the following structural formulas:

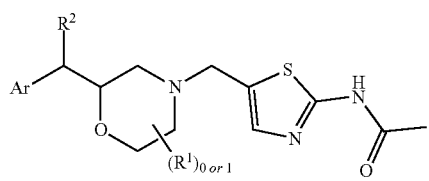

(VA)

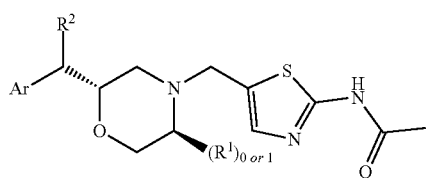

(VA-1)

or a pharmaceutically acceptable salt thereof; wherein $R^d$ is —H, —$CH_3$, —$CH_2CH_3$, or —C(=O)$CH_3$.

12. The compound according to claim 1, wherein Ar is an optionally substituted 5- or 6-membered monocyclic heteroaryl; or wherein Ar is an optionally substituted 6-membered monocyclic heteroaryl comprising one or more nitrogen atoms.

13. The compound according to claim 1 or a pharmaceutically acceptable salt thereof, wherein Ar is an optionally substituted pyridinyl, an optionally substituted pyrimidinyl, or an optionally substituted pyrazinyl.

14. The compound according to claim 1 or a pharmaceutically acceptable salt thereof, wherein Ar is optionally substituted

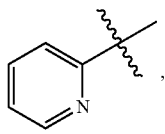, optionally substituted

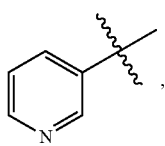, optionally substituted

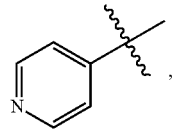, optionally substituted

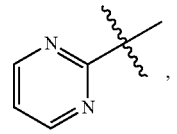 [SMILES: *c1ncccn1], optionally substituted

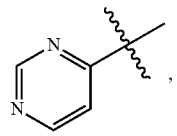, or optionally substituted

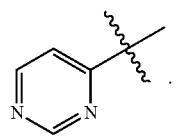.

15. The compound according to claim 1 or a pharmaceutically acceptable salt thereof, wherein Ar is optionally substituted with one or more groups selected from $C_1$-$C_4$ alkyl, $C_1$-$C_4$ haloalkyl, halo, —CN, —$OR^z$, and —$NR^xR^y$.

16. The compound according to claim 1 or a pharmaceutically acceptable salt thereof, wherein Ar is optionally substituted with one or more groups selected from $C_1$-$C_4$ alkyl, $C_1$-$C_4$ haloalkyl, —F, —Cl, —CN, and —$OR^z$; wherein $R^z$ is $C_1$-$C_4$ alkyl optionally substituted with one or more halo groups.

17. The compound according to claim 1 or a pharmaceutically acceptable salt thereof, wherein Ar is optionally substituted with one or more groups selected from —$CH_3$, —$CF_3$, —$CHF_2$, —F, —$OCH_3$, —$OCHF_2$, —$OCH_2CH_3$, —$OCH(CH_3)_2$, and —$OCH_2CF_3$.

18. A pharmaceutical composition comprising the compound according to claim 1 or a pharmaceutically acceptable salt thereof and a pharmaceutically acceptable carrier or diluent.

* * * * *

UNITED STATES PATENT AND TRADEMARK OFFICE
CERTIFICATE OF CORRECTION

PATENT NO. : 12,319,679 B2
APPLICATION NO. : 17/311232
DATED : June 3, 2025
INVENTOR(S) : Nathan Genung et al.

Page 1 of 2

It is certified that error appears in the above-identified patent and that said Letters Patent is hereby corrected as shown below:

In the Claims

At Column 95, Claim number 11, Line numbers 7-25, please replace

"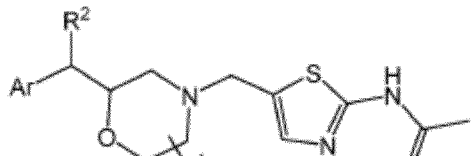

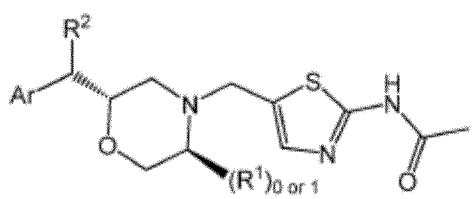" with

Signed and Sealed this
Nineteenth Day of August, 2025

Coke Morgan Stewart
*Acting Director of the United States Patent and Trademark Office*

CERTIFICATE OF CORRECTION (continued)
U.S. Pat. No. 12,319,679 B2

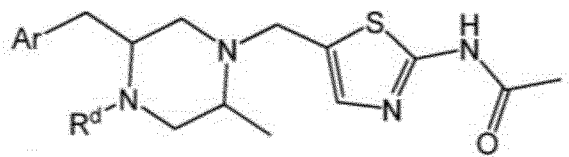

(IVC-1) or

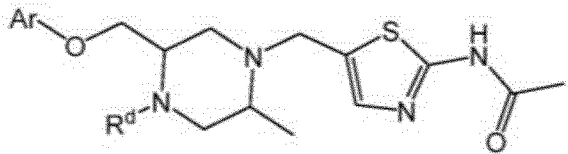

(IVC-2)

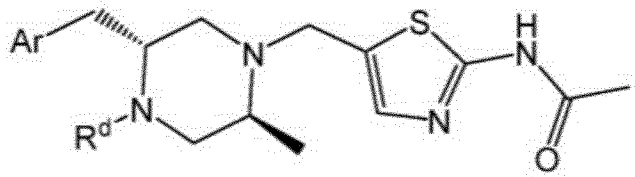

(VC-1)

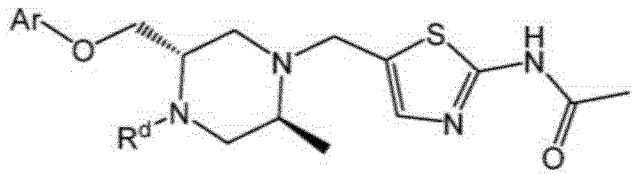

(VC-2)

-- --.